United States Patent
Gozes et al.

(10) Patent No.: US 6,239,107 B1
(45) Date of Patent: May 29, 2001

(54) CONJUGATES OF LIPOPHILIC MOIETIES AND FRAGMENTS OF VASOACTIVE INTESTINAL PEPTIDE (VIP)

(75) Inventors: Illana Gozes, Ramat Hasharon; Matityahu Fridkin, Rehovot, both of (IL)

(73) Assignees: Yeda Research & Development Co., Ltd., Rehovot; Ramot University Authority for Applied Research and Industrial Development Ltd., Tel-Aviv, both of (IL)

( * ) Notice: Subject to any disclaimer, the term of this patent is extended or adjusted under 35 U.S.C. 154(b) by 0 days.

(21) Appl. No.: 09/171,654

(22) PCT Filed: Apr. 18, 1997

(86) PCT No.: PCT/IL97/00129

§ 371 Date: Apr. 29, 1999

§ 102(e) Date: Apr. 29, 1999

(87) PCT Pub. No.: WO97/40070

PCT Pub. Date: Oct. 30, 1997

(30) Foreign Application Priority Data

Apr. 23, 1996 (IL) ......................................................... 118003

(51) Int. Cl.[7] .......................... A61K 38/06; A61K 38/07; A61K 38/08; A61K 38/10; C07K 14/575
(52) U.S. Cl. ................................ 514/14; 514/15; 514/16; 514/17; 514/18; 530/327; 530/328; 530/329; 530/330; 530/331; 530/345

(58) Field of Search ................................. 514/12, 14, 15, 514/16, 17, 18, 21; 530/324, 327, 328, 329, 330, 331, 345

(56) References Cited

U.S. PATENT DOCUMENTS 5,426,099 * 6/1995 Komisaruk et al. .................... 514/13
5,428,015 * 6/1995 Kurono et al. ......................... 514/12
5,972,883 * 10/1999 Gozes et al. ........................... 514/12

FOREIGN PATENT DOCUMENTS 0 225 020   6/1987  (EP).
0 325 044   7/1989  (EP).
0 354 992   2/1990  (EP).
0 540 969   5/1993  (EP).
0 620 008  10/1994  (EP).

OTHER PUBLICATIONS

Veki et al. Peptide Synthesis in Alcohol Solvents by the Mixed . . . Bull. Chem. Soc. Japan vol. 61, No. 10, pp. 3653–3657, Oct. 1988.*

* cited by examiner

Primary Examiner—Jeffrey E. Russel
(74) Attorney, Agent, or Firm—Browdy and Neimark

(57) ABSTRACT

The invention concerns novel conjugates of peptide fragments of vasoactive intestinal peptide (VIP) or analogues thereof having 3–12 amino acid residues, and lipophilic moieties, which may be present at the N- or C-terminus. The invention further concerns pharmaceutical compositions containing these novel conjugates which may be used for treatment of male impotence or for the treatment of neurodegenerative diseases.

24 Claims, 24 Drawing Sheets

CONJUGATES OF LIPOPHILIC MOIETIES AND FRAGMENTS OF VASOACTIVE INTESTINAL PEPTIDE (VIP)

FIELD OF THE INVENTION

The present invention concerns novel conjugates of a lipophilic moiety and a peptide of 3–12 amino acids. The present invention further concerns pharmaceutical compositions comprising as an active ingredient said novel conjugates. The pharmaceutical compositions of the invention are preferably used for the treatment of male impotence or for the treatment of neurodegenerative diseases.

BACKGROUND OF THE INVENTION

Vasoactive intestinal peptide (VIP), a 28 amino acid neuropeptide widely distributed in the mammalian nervous system, has potent neurotrophic actions that influence nerve cell function. In the central nervous system, this role of VIP is translated into developmental effects, display of growth factor activities and maintenance of neuronal survival and function. Neurons, which are capable of releasing VIP, innervate blood vessels throughout the body, as well as the trachea in the lung, and the released VIP serves as a potent vasodilator, inducing smooth muscle relaxation. Radioligand binding assays, pharmacological experiments, molecular cloning and development of superactive novel derivatives have indicated several classes of VIP receptor sites and several potential therapeutical uses.

Two possible therapeutic uses of VIP, modified VIP or lipophilic VIP derivatives were reported in our previous Patents IL 87055, EP 0354992 and U.S. Pat. No. 5,147,855 and published patent applications EP 0540969 and EP 0620008 which are directed to the treatment of male impotence by transdermal administration and to the treatment of neurodegenerative diseases, respectively.

VIP is a hydrophilic peptide of a very short half life in the serum (Said, S. I., Editor, *Vasoactive intestinal peptide* in: Advances in Peptide Hormone Research Series, Raven Press, New York, 1–512 (1982)) having the following sequence:

(SEQ ID NO:1)

```
 1   2   3   4   5   6   7   8   9  10  11  12
His-Ser-Asp-Ala-Val-Phe-Tyr-Asp-Asn-Tyr-Thr-Arg- 13  14  15  16  17  18  19  20  21  22  23  24
Leu-Arg-Lys-Gln-Met-Ala-Val-Lys-Lys-Tyr-Leu-Asn- 25  25  27  28
Ser-Ile-Leu-Asn-NH₂
```

To enhance its biological availability and increase its stability the present inventors have resorted to two chemical modifications reported in said patents and applications. The first was lipophilization, namely, the addition of a fatty acid moiety, designed to augment VIP's ability to penetrate biological membranes without loss of activity; thus, stearoyl-VIP, a molecule combining VIP with a stearic acid moiety at its N-terminal was designed (EP 0354992). The second modification was the replacement of native amino acids with unnatural amino acids, namely, a substitution of methionine (amino acid 17 of VIP) by norleucine, aimed at stabilizing the molecule against oxidation as well as at increasing lipophilicity; thus, stearoyl-Nle-VIP was designed (Gozes et al., *Endocrinology*, 134:2121–2125 (1994); Fauchere et al., *Int. J. Peptide Protein Res.*, 32:269–278 (1988); EP 0540969). Unmodified VIP fragments derived from the 17–24 positions of the VIP sequence are described in EP 0225020 as ulcer inhibitors.

A major obstacle in the use of any substance as a medicament is its distribution in the body. The modified VIP or lipophilic VIP used for transdermal treatment of male impotence reported in the abovementioned EP 0354992 and EP 0540969 have to penetrate through the dermis and reach the erectile tissues in a short a time span as possible.

VIP, modified VIP or lipophilic VIP used to treat neurodegenerative diseases described in EP 0620008 have to pass the blood brain barrier in order to exert their therapeutic effect on brain cells.

It would have been desirable, both for the purpose of treatment of male impotence and for the purpose of administration to the CNS for the treatment of neurodegenerative diseases, to use molecules that, while having the physiological activity of the full VIP peptide, are smaller in size and thus are able to improve the bioavailability of the therapeutic compound at the target tissue. Furthermore, smaller molecules are at times more stable to degradation than larger molecules since, as a rule, they have less sites available to degradation.

SUMMARY OF THE INVENTION

The present invention is based on the surprising finding that short fragments of VIP or modified VIP conjugated to a lipophilic moiety, which are 3–12 amino acids long, are physiologically active in the treatment of impotence and/or neurodegenerative diseases. The advantage of using short physiologically active peptides conjugated to a lipophilic moiety versus the usage of the full VIP molecule is better biodistribution and bioavailability in the body, as well as ease of preparation. Furthermore, the invention concerns short cyclic peptides containing said short fragments of VIP or of modified VIP conjugated to a lipophilic moiety which in addition to the above advantages feature the advantage of being relatively degradation resistant.

The present invention is concerned with a conjugate of a peptide coupled to a lipophilic moiety, wherein the peptide has at least 3 and at most 12 amino acid residues, said conjugate being selected from the formulae:

(i) $R_1\text{-}X_1\text{-}X_1'\text{-}X_1''\text{-}X_2\text{-}NH\text{—}R_2$ (SEQ ID NO:2);

(ii) $R_1\text{-}X_3\text{-}Ser\text{-}X_4\text{-}Leu\text{-}Asn\text{-}NH\text{—}R_2$ (SEQ ID NO:3);

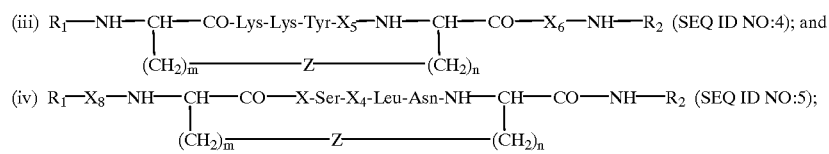

wherein
R$_1$ is H or a lipophilic moiety;
R$_2$ is H, a lipohililc moiety, a lipophilic moiety substituted by X$_3$-Ser-X$_4$-Leu-Asn-NHR$_1$ (SEQ ID NO:79) or a spacer consisting of 1–3 residues of a non-charged amino acid coupled to X$_1$-X$_1$'-X$_1$"-X$_2$NHR$_1$ (SEQ ID NO:80),
with the proviso that at least one of R$_1$ and R$_2$ is a lipohilic moiety;
X$_1$ is a covalent bond, Ala, Val, Ala-Val, Val-Ala, L-Lys, D-Lys, Ala-Lys, Val-Lys, Ala-Val-Lys; Val-Ala-Lys or Orn;
X$_1$ is L-Lys, D-Lys or Orn;
X$_1$" is L-Tyr, D-Tyr, Phe, Trp or the residue of p-amino phenylalanine;
X$_4$ is Ile or Tyr;
X$_5$ is a residue of a hydrophobic aliphatic amino acid;
X$_2$ is X$_5$, X$_5$-Asn, X$_5$-Ser, X$_5$-Ile, X$_5$-Tyr, X$_5$Leu, X$_5$-Nle, X$_5$-D-Ala, X$_5$-Asn-Ser, X$_5$-Asn-Ser-Ile (residue 1–4 of SEQ ID NO:75), X$_5$-Asn-Ser-Tyr (residues 1–4 of SEQ ID NO:76); X$_5$-Asn-Ser-Ile-Leu (residues 1–5 of SEQ ID NO:75), X$_5$-Asn-Ser-Tyr-Leu (residues 1.5 of SEQ ID NO:76), X$_5$-Asn-Ser-Ile-Leu-Asn (SEQ ID NO:75) or X$_5$-Asn-Ser-Tyr-Leu-Asn (SEQ ID NO:76);
X$_3$ is a covalent bond, Asn, X$_5$, X$_5$-Asn, Tyr-X$_5$, Tyr-X$_5$-Asn, Lys-X$_5$, Lys-X$_5$-Asn, Lys-Tyr-X$_5$, Lys-Tyr-X$_5$-Asn (residues 4–7 of SEQ ID NO:77), Lys-Lys-Tyr-X$_5$ ((residues 3–6 of SEQ ID NO:77), Lys-Lys-Tyr-X$_5$-Asn (residues 3–7 of SEQ ID NO:77), Val-Lys-Lys-Tyr-X$_5$ (residues 2–6 SEQ ID NO:78), Val-Ala-Lys-Lys-Tyr-X$_5$-Asn (SEQ ID NO:77), or Ala-Val-Lys-Lys-tyr-X$_5$-Asn (SEQ ID NO:78);
X$_6$ is a covalent bond or Asn, Ser, Ile, Tyr, Leu, Asn-Ser, Asn-Ser-Ile, Asn-Ser-Tyr, Asn-Ser-Ile-Leu (residues 2–5 of SEQ ID NO:75), Asn-Ser-Tyr-Leu (residues 2–5 of SEQ ID NO:76), Asn-Ser-Ile-Leu-Asn (residues 2–6 of SEQ ID NO:75) or Asn-Ser-Tyr-Leu-Asn (residues 2–6 of SEQ ID NO:76);
X$_7$ is a covalent bond or Asn;
X$_8$ is a covalent bond, X$_5$, Tyr, Lys, Tyr-X$_5$, Lys-X$_5$, Lys-Tyr-X$_5$, Lys-Lys-Tyr-X$_5$ (residues 3–6 of SEQ ID NO:77), Val-Lys-Lys-Tyr-X$_5$ (residues 2–6 of SEQ ID NO:78), Ala-Lys-Lys-Tyr-X$_5$ (residues 2–6 of SEQ ID NO:77), or Ala-Val-Lys-Lys-Tyr-X$_5$ (residues 1–6 of SEQ ID NO:78);
Z is —CCNH—, —NHCO—, —S—S—, —S(CH$_2$)$_t$CO—NH— or —NH—CO(CH$_2$)$_t$S—;
m is 1 or 2 when Z is —CONH—, —S—S— or —S(CH$_2$)$_t$CO—NH—, or m is 2, 3 or 4 when Z is —NH—CO— or —NH—CO(CH$_2$)$_t$S—;
n is 1 or 2 when Z is —NH—CO—, —S—S— or —NH—CO(CH$_2$)$_t$S—, or n is 2, 3 or 4 when Z is —CONH— or —S(CH$_2$)$_t$CO—CO—NH—, and
t is 1 or 2,
with the proviso that the conjugate stearoyl-Ala-Val-Lys-Lys-Tyr-Leu-Asn-Ser-Ile-Leu-Asn-NH$_2$ (SEQ ID NO:24) is excluded.

The hyrdophobic aliphatic amino acid represented above by X$_5$ may be a residue of D- or L- amino acid selected from Ala, Ile, Leu, Met, Val, Nva and Nle.

The term "lipophilic moiety of the conjugates of the invention" will refer in the following description and claims to: a saturated or unsaturated hydrocarbyl or carboxylic acyl radical having at least 3 carbon atoms such as propionyl, caproyl, laurly, palmitoyl, stearoyl, oleyl, eicosanoyl, docsanoyl and the respective hydrocarbyl radicals propyl, hexyl, dodecyl, hexadecyl, octadecyl, eicosanyl and docosanyl. Preferably the hydrocarbyl or acyl radical is saturated, and has 3–22 carbon atoms.

The term "spacer" refers to residue of a non-charged natural or non-natural amino acid such as alanine, proline and aminocaproic acid.

Examples of the conjugates of the invention are conjugates of a lipophilic moiety and peptides of the sequence Lys-Lys-Tyr-Leu derived from position 20–23 of the VIP sequence (SEQ ID NO:1) and/or peptides of the sequence Asn-Ser-Ile-Leu-Asn, derived from positions 24–28 of the VIP sequence (SEQ ID NO:1). modified peptides thereof in which amino acid residues have been replaced, added, deleted or chemically modified or combinations of these two sequences such as:
St-Lys-Lys-Tyr-Leu-NH$_2$ (SEQ ID NO:6);
St-Lys-Lys-Tyr-D-Ala-NH$_2$;
St-Ala-Val-Lys-Lys-Tyr-Leu-NH$_2$ (SEQ ID NO:7);
St-Asn-Ser-Ile-Leu-Asn-NH$_2$ (SEQ ID NO:8);
St-Lys-Lys-Tyr-Val-NH$_2$ (SEQ ID NO:9);
St-Ser-Ile-Lau-Asn-NH$_2$;
St-Lys-Lys-Tyr-Leu-Nle-NH$_2$ (SEQ ID NO:10);
St-Asn-Ser-Tyr-Leu-Asn-NH$_2$ (SEQ ID NO:11);
St-Asn-Ser-Ile-Tyr-Asn-NH$_2$ (SEQ ID NO:12);
St-Lys-Lys-Tyr-Leu-Pro-Pro-Asn-Ser-Ile-Leu-Asn-NH$_2$ (SEQ ID NO:13;
Lau-Lys-Lys-Tyr-Leu-NH$_2$ (SEQ ID NO:14);
Cap-Lys-Lys-Tyr-Leu-NH$_2$ (SEQ ID NO:15);
St-Lys-Tyr-Leu-NH$_2$;
St-Lys-Lys-Tyr-Nle-NH$_2$ (SEQ ID NO:16);
St-Val-Lys-Lys-Tyr-Leu-NH$_2$ (SEQ ID NO:17);
St-Leu-Asn-Ser-Ile-Leu-Asu-NH$_2$ (SEQ ID NO:18;
St-Tyr-Leu-Asn-Ser-Ile-Leu-Asn-NH$_2$ (SEQ ID NO:19);
St-Lys-Lys-Tyr-Leu-Asn-NH$_2$ (SEQ ID NO:20);
St-Lys-Lys-Tyr-Leu-Asn-Ser-NH$_2$ (SEQ ID NO:21);
St-Lys-Lys-Tyr-Leu-Asn-Ser-Ile-NH$_2$ (SEQ ID NO:22); and
St-Lys-Lys-Tyr-Leu-Asn-Ser-Ile-Leu-NH$_2$ (SEQ ID NO:23).

In the following, the symbol "St" stands for stearoyl, "Lau" stands for lauroyl and "Cap" stands for caproyl.

By another aspect the present invention concerns pharmaceutical compositions comprising as an active ingredient, active conjugates of the invention together with a pharmaceutically acceptable carrier.

The pharmaceutical composition of the invention comprising a conjugate of the invention or the conjugate St-Ala-Val-Lys-Lys-Tyr-Leu-Asn-Ser-Ile-Leu-Asn-NH$_2$ (SEQ ID NO:24) (hereinafter "Peptide") described in EP 0620008 may be used for the treatment of sexual disfunctions such as male impotence, preferably by transdermal or urinary tract application. Preferred conjugates used for this purpose are:
St-Lys-Lys-Tyr-Leu-NH$_2$ (SEQ ID NO:6);
St-Lys-Lys-Tyr-D-Ala-NH$_2$;
St-Ala-Val-Lys-Lys-Tyr-Leu-NH$_2$ (SEQ ID NO:7);
St-Asn-Ser-Ile-Leu-Asn-NH$_2$;
St-Lys-Lys-Tyr-Val-NH$_2$ (SEQ ID NO:9);
St-Ser-Ile-Lau-Asn-NH$_2$;
St-Asn-Ser-Tyr-Leu-Asn-NH$_2$ (SEQ ID NO:11);
St-Asn-Ser-Ile-Tyr-Asn-NH$_2$;
St-Lys-Lys-Tyr-Leu-Nle-NH$_2$ (SEQ ID NO:10); and
St-Lys-Lys-Tyr-Leu-Pro-Pro-Asn-Ser-Ile-Leu-Asn-NH$_2$ (SEQ ID NO:13).

The pharmaceutical compositions of the invention may also be used for the treatment of neurodegenerative diseases, such as Alzheimer, Down Syndrome, hypoxia, decline in motor or cognitive function due to ischemia, stroke, hereditary diseases of the central and peripheral nervous system, decline in motor or cognitive function due to injury of the central or peripheral nervous system, decline in cognitive functions due to old age and neurological disorders associated with blood circulation and neuronal survival. The term "treatment" should be understood in the context of the present invention as alleviation, improvement or abolishment of the abnormal conditions manifested in those diseases and more particularly to improvement in cognitive functions damaged by those diseases. Preferred conjugates used for this purpose are:

St-Lys-Lys-Tyr-Leu-NH$_2$ (SEQ ID NO:6);
St-Lys-Lys-Tyr-D-Ala-NH$_2$;
St-Ala-Val-Lys-Lys-Tyr-Leu-NH$_2$ (SEQ ID NO:7);
St-Asn-Ser-Ile-Leu-Asn-NH$_2$ (SEQ ID NO:8);
St-Lys-Lys-Tyr-Val-NH$_2$ (SEQ ID NO:9);
St-Ser-Ile-Lau-Asn-NH$_2$;
Lau-Lys-Lys-Tyr-Leu-NH$_2$ (SEQ ID NO:14);
Cap-Lys-Lys-Tyr-Leu-NH$_2$ (SEQ ID NO:15);
St-Lys-Tyr-Leu-NH$_2$;
St-Lys-Tyr-Leu-NH$_2$;
St-Lys-Lys-Tyr-Nle-NH$_2$ (SEQ ID NO:16);
St-Val-Lys-Lys-Tyr-Leu-NH$_2$ (SEQ ID NO:17);
St-Leu-Asn-Ser-Ile-Leu-Asn-NH$_2$ (SEQ ID NO:18);
St-Tyr-Leu-Asn-Ser-Ile-Leu-Asn-NH$_2$ (SEQ ID NO:19);
St-Lys-Lys-Tyr-Leu-Nle-NH$_2$ (SEQ ID NO:10);
St-Lys-Lys-Tyr-Leu-Asn-NH$_2$ (SEQ ID NO:20);
St-Lys-Lys-Tyr-Leu-Asn-Ser-NH$_2$ (SEQ ID NO:21);
St-Lys-Lys-Tyr-Leu-Asn-Ser-Ile-NH$_2$ (SEQ ID NO:22); and
St-Lys-Lys-Tyr-Leu-Asn-Ser-Ile-Leu-NH$_2$ (SEQ ID NO:23).

Optional modes of administration of pharmaceutical compositions of the invention are subcutaneous, intravenous, oral, nasal, ocular, by an intracerebroventricular pump, through the urinary tract or transdermal administration.

Where the pharmaceutical compositions of the invention are used to treat impotence, urinary tract or transdermal administration are preferable. For transdermal application the carrier is preferably selected from amongst those which enhance the tissue penetration of the active ingredient. Examples of suitable carriers are olive oil, glycerine, lubricants, nitroglycerin and Sefso™, and mixtures thereof. Sefsol is a trademark (Nikko Chemicals, Tokyo) for, 1-glyceryl monocaprylate, propylene glycol didecanoate, propylene glycol dicaprylate, glyceryl tricaprylate and sorbitan monocaprylate and they are the preferred carriers in compositions according to the invention. Of these, 1-glyceryl monocaprylate and olive oil are particularly preferred. For urinary tract application a gel is preferably used as a carrier.

The present invention further provides, for the sustained release of a conjugate of the invention, a transdermal dispenser comprising an applicator loaded with said conjugate and adapted for application to the skin.

If desired, the conjugate in the applicator may be formulated into a pharmaceutical composition of the kind specified above.

Treating male impotence by transdermal administration exhibits several advantages over modes of parenteral, such as subcutaneous, administration. For one, it is non-surgical and does not entail tissue destruction. Moreover, it does not cause priapism or the burning pain associated with other modes of administration. Furthermore, the transdermal application is a much more discreet and convenient mode of application as compared to an intracavernosal injection. Transdermal administration enables the use of a continuous slow release device which may enable spontaneous sexual activity without the need for a lengthy preparation, thus sparing an inflicted individual much of the usual embarrassment.

Where the pharmaceutical compositions of the invention are to be used as drugs acting on the central nervous system, it is preferable to administer them through the nose, which enables the penetration of the aerosol composition to the CNS through the olfactory nerve (WO 91/07947), via the ocular route (Chiou, G. C. Y., (1991) *An. Rev. PharmacoL Toxical.*, 31:457–67) or by any other suitable method of administration as described in W. M. Pardridge, *Peptide Drug Delivery*, Raven Press, N.Y. 1991.

The pharmaceutical compositions of the invention may be also directly targeted to the brain by an intracerebroventricular pump.

The present invention further concerns a method of treatment of neurodegenerative diseases or male impotence by administering to a host in need of such treatment a therapeutically effective amount of the conjugate of the invention.

The present invention still further provides use of the conjugate of the invention for the preparation of a pharmaceutical composition.

As will be appreciated by any person versed in the art, the conjugates as defined above in formulae I above include a large number of possible conjugates. Those which fall under the scope of the invention and those defined as "active conjugates" in the pharmraceutical composition of the invention are the conjugates which are active in at least one of the following assays:

(1) conjugates which are able to induce erection in an animal model of impotence (normal and castrated animals);

(2) conjugates which have the activity of protecting electrically blocked neurons from death;

(3) conjugates which are able to protect untreated neurons in culture from naturally occurring death;

(4) conjugates which are able to protect cultured neurons from death caused by a 25–35 fragment of β-amyloid peptide;

(5) conjugates which are able to avoid deterioration of learning and memory acquisition of either old animals or animals treated with a dementia causing agent as tested in an acceptable learning of memory acquisition assay, as well as conjugates which are able to improve recollection of a previously acquired task in animals treated with a dementia causing agent, for example, as described in example.

(6) conjugates which are able to avoid or ameliorate decline of motor and cognitive functions in an animal model of ischemia and/or models of stroke;

(7) conjugates which are able to protect neurons from damage caused due to lack of oxygen;

(8) conjugates which are able to improve motor and cognitive functions in models for hereditary neurodegenerative diseases of the central and peripheral nervous system such as models of mice with a knock out of ApoE (*Cell*, 71:343 (1992)); transgenic models of amyloid over-expression (*Nature*, 373:523 (1995)); models for ALS which are mutant super oxide dismutase expression (*Science*, 264, 1772 (1994)) and a model for Down Syndrome which is trisomy of chromosome 16; and (9) conjugates which are able to improve motor and cognitive functions in models of injury of the central and peripheral nervous system such as lesions of the nucleus basalis in rats (*PNAS*, 85:9481 (1988)); scopolamine-induced acetylcholine release in ventral hippocampus (*PNAS*, 90:11287 (1993)); NMDA induced convulsions (*Brain Res.* 448:115 (1988)).

In the following, the invention will be further illustrated with reference to some non-limiting drawings and examples.

DETAILED DESCRIPTION OF THE INVENTION

A. Synthesis of Linear Peptides

Figure 1:
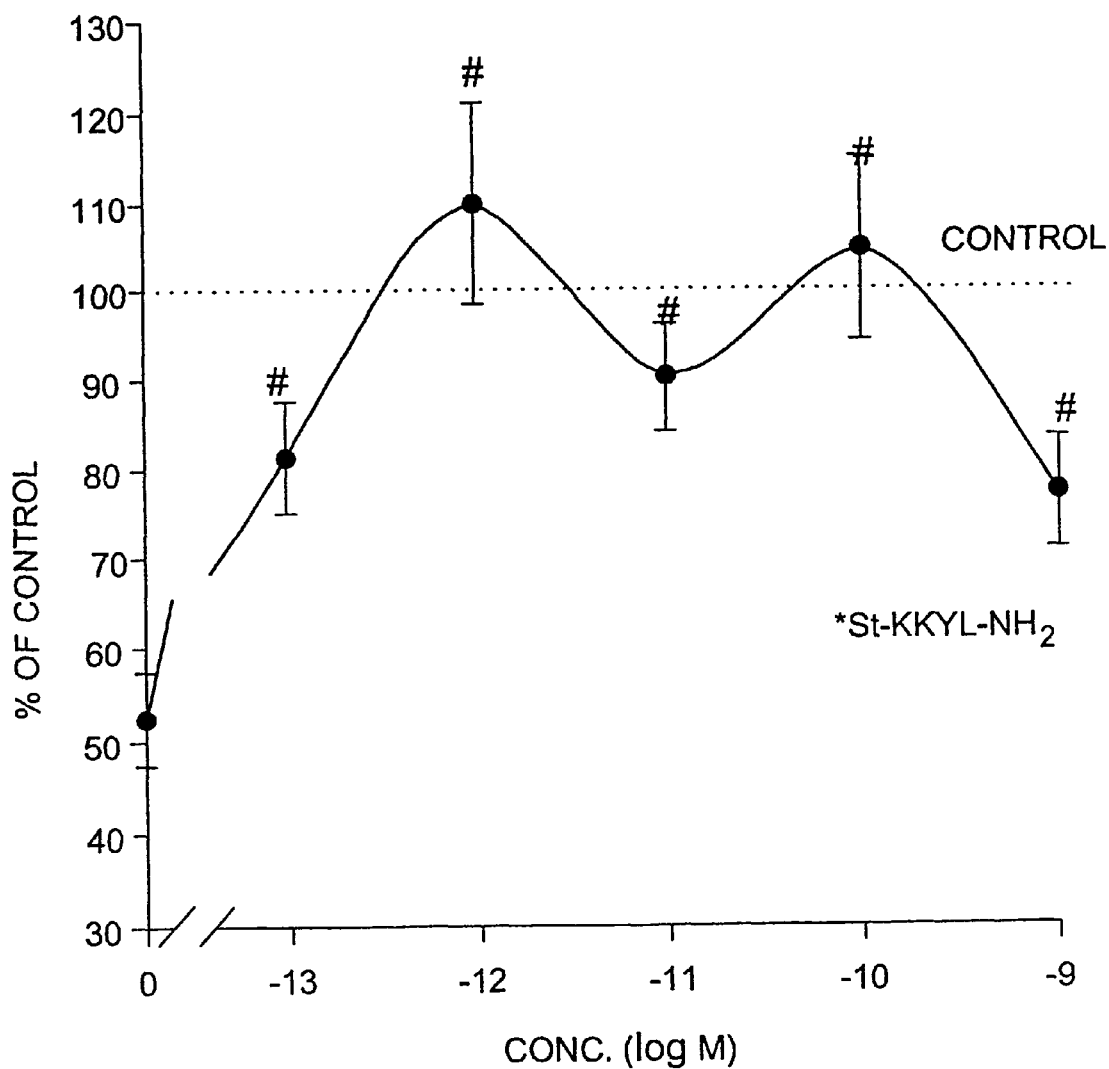
FIG. 1 shows the effect of varying concentrations of St-Lys-Lys-Tyr-Leu-NH$_2$ (SEQ ID NO:6) on the survival of neurons treated with β-amyloid peptide.

To obtain a large battery of small peptides an automatic peptide synthesizer was utilized. Syntheses of the peptides of the invention were achieved by automatic procedure employing an ABIMED AMS 422 synthesizer (ABIMED, Langenfeld, Germany) using the commercially available protocols via the Fmoc strategy. All protected amino acid derivatives were as recommended by the company. Thus, the following side-chain protection was utilized: Lys, N-epsilon-t-butyloxycarbonyl (Boc), Tyr, Thr, Ser, O-t-butyl; Arg; 2,2,5,7,8-pentamethylchroman-6-sulfonyl (PMC); Trp, $N^{int}$-Boc; Cys, S-trityl, Asn, beta-trityl, PyBOP, i.e. benzotriazol-1-yl-oxy-tris-pyrrolidino-phosphonium hexafluorophosphate, was used as a coupling agent. Peptide chains were assembled on a 4-([2",4"-dimethoxyphenyl] Fmoc aminoethyl) phenoxy resin (Rink amide Resin, Nova, Switzerland).

Final cleavage of the peptide chain from the resin along with the side chain deprotection was achieved as follows: cleavage mixture: 90% TFA, 5% water, 5% triethylsilane. The resin, 100 mg, loaded with peptide was incubated for 30 min with a 3 ml cleavage mixture inside the reaction column used for solid phase synthesis. After 30 min, the reaction was separated from the cleaved resin and cleavage continued for an additional 3 hrs. The cleaved peptide was precipitated with ice cold tert-butylmethyl ether and centrifuged (4° C., 2000 rpm). To ensure optimal precipitation, petroleum ether (b.p. 40–60° C., 1:1 v/v) was occasionally added. The solution was decanted and the pellet was dissolved in water and frozen for lipophilization to yield a white powder. Purification of the crude peptides was performed by semi-preparative HPLC on an RP-8 column (Merck 7 $\mu$M; 250× 10 mm) employing linear gradient established between 35% acetonitrile in water containing 0.1% TFA, and 0.1% TFA in 75% acetonitrile in water at a flow rate of 10 m/min. Elution was monitored at 220 nm. Yields were 30–45%. Purity of the products was ascertained by analytical HPLC on an RP-18 column (Merck; 250×4 mm) and amino acid analysis following exhaustive acid hydrolysis gave the expected values of each constituent amino acid.

Examples of the conjugates comprising linear peptides that were synthesized by this method are those listed on pages 5–9 hereinbefore and the following conjugates are:

|  | SEQ. ID. NO: |  | SEQ. ID. NO: |
| --- | --- | --- | --- |
| 1. CapKKYLZZ* | 26 | 29. StYLNSILN* | 19 |
| 2. LauKKYLZ* | 27 | 30. StKKYLNle* | 10 |
| 3. KKYLZ* | 28 | 31. StKKYLO* | 49 |
| 4. KKYLZZ* | 29 | 32. StKKYLL* | 50 |
| 5. KKYLB* | 30 | 33. StKBYL* | 51 |
| 6. KKYLZZZ* | 31 | 34. StBKYL* | 52 |
| 7. LauNSILNZ* | 32 | 35. StBBYL* | 53 |
| 8. NSILNZ* | 33 | 36. StKKFL* | 54 |
| 9. NSILNZZ* | 34 | 37. StKKOL* |  |
| 10. CapNSILNZZ* | 35 | 38. StKKYZ* | 55 |
| 11. NSILNZZZ* | 36 | 39. StKKWL* | 56 |
| 12. NSILNB* | 37 | 40. StKKXL* | 57 |
| 13. KKYLZNSILN* | 38 | 41. StKOrnYl* | 58 |
| 14. KKYLZZNSILN* | 39 | 42. StOrnKYL* | 59 |
| 15. KKYLZZZNSILN* | 40 | 43. StOrnOrnYL* | 60 |
| 16. KKYLBNSILN* | 41 | 44. OIKKYL* | 61 |
| 17. StKKYLXXXNSILN* | 42 | 45. PropylKKYL* | 62 |
| 18. StKKLYAAANSILN* | 43 | 46. StKKYLAAKKYL* | 63 |
| 19. StKKYLPNSILN* | 44 | 47. StKKYLPPKKYL* | 64 |
| 20. StKKYLPPNSILN* | 13 | 48. StKKYLAcaKKYL* | 65 |
| 21. StKYLNSILN* | 45 | 49. StKKYLAm.Lauryl KKYL* | 66 |
| 22. StKKYLNSILN* | 46 | 50. StKKYLNle* | 10 |
| 23. StKKYLN* | 20 | 51. StKKYLdA* |  |
| 24. StKKYLNS* | 21 | 52. StKKYLL* | 67 |
| 25. StKKYLNSI* | 22 | 53. CapKKYL* | 15 |
| 26. StKKYLNSIL* | 23 | 54. LauKKYL* | 14 |
| 27. LauKKYLNSILN* | 47 | 55. CapNSILN* | 68 |
| 28. StKYLN* | 48 | 56. LauNSILN* | 69 | wherein Cap=Caproic acid, Lau=Lauric acid, St=Stearic acid; Z=Aminocaproic acid, B=Aminolauric acid, X=d, lAla, O=D-Ala; B=dK, O=dY, Z=dL, X=p=aminoPhe, *=amid, Ol=Oleic acid B. Synthesis of Cyclic Peptides I. Cyclic peptides containing intramolecular amide bonds, i.e. Z=—CONH— or —NHCO— of the formulae III and IV as defined above may be prepared through conventional solid phase synthesis. Thus, peptide chains may be assembled on the solid support while incorporating suitable amino and carboxyl side-chain protected amino acid derivatives at the positions selected for cyclization. Following completion of peptide chain assembly, the protecting groups can be selectively removed from the corresponding amino and carboxyl functions, leaving other protecting groups and the peptide-support bond intact. Cyclization can then be accomplished using known peptide coupling agents. Finally, the cyclic peptide may be cleaved from the support along with deprotection of side chain moieties using known procedures, and purification of the desired cyclic peptide can be achieved by chromatographic techniques.

II. Cyclic peptides containing an intramolecular disulfide bond, i.e. Z=S—S of the formulae III and IV as defined above may be prepared through conventional solid phase synthesis while incorporating suitable S-protected cysteine or homocysteine residues at the positions selected for cyclization. Following completion of the chain assembly, two possible routes for cyclization can be performed: 1. Selective removal of S-protecting groups with a consequent on-support oxidation of free corresponding two SH-functions, to form S'—S bonds. This may be followed by conventional removal of the product from the support and appropriate chromatographic purification. 2. Removal of the peptide from the support along with complete side-chain deprotection, followed by oxidation of free SH-functions in highly dilute aqueous solution. Both routes lead to the same final desired product.

III. Cyclic peptides containing intramolecular S-alkyl bonds, i.e. Z=—S(CH$_2$)$_t$CO—NH or —NH—CO(CH$_2$)$_t$S— of the formulae III and IV as defined above may be prepared through conventional solid phase synthesis. Thus, an amino acid residue with a suitable amino-protected side chain, and a suitable S-protected cysteine or homocysteine residue may be incorporated during peptide chain assembly at positions selected for cyclization. The blocked side-chain amino function is selectively deprotected followed by bromoacylation. The peptide can then be detached from the support, along with side-chain deprotection, under acidic conditions. Under neutral or slightly basic conditions, the corresponding free SH and bromoacylated moieties may then selectively interact at high dilution to afford the desired cyclic peptide.

EXAMPLE B1

Synthesis of Stearoyl-Lys-Lys-Lys-Tyr-Leu-Asp-NH2 (SEQ ID NO:70)

[General formula (iii) above wherein $X_5$=Leu; $X_6$=covalent bond; Z=—NH—CO—; m=4, n=1]

Synthesis of the peptide is performed manually on a p-amethylbenzhydrylamine (MBHA) resin available from Nova, Switzerland. All solvents, methylene chloride ($CH_2Cl_2$), N-methylpyrrolidone (NMP) and dimethyl sulfoxide (DMSO) are analytical products of Merck, Germany. Trifluoroacetic acid (TFA), diisopropylethylamine (DIEA) and N,N'-dicyclohexylcarbodiimide (DCC) are purchased from Aldrich, U.S.A. 1-Hydroxybenzotriazole (HOBT) is obtained from Nova, Switzerland. All protected amino acid derivatives (Boc-AA) are of the L-configuration and are obtained from Bachem, Switzerland. Nα-amino acid functions are protected throughout the synthesis by the t-butyloxycarbonyl (t-Boc) group. Side chain functions are protected as follows: Asp with 9-fluorenylmethyl (Fm), Lys with 2-chloro-benzyloxycarbonyl, and at position 1 of the peptide chain with 9-fluorenylmethoxycarbonyl (Fmoc) and Tyr with 2,6-dichlorobenzyl.

The synthesis is initiated by coupling Boc-Asp (OFm) (0.82 g, 2 mmol) to the methylbenzhydryl amine resin (1 g) using DCC (0.42 g, 2 mmol) and HOBT (0.272 g, 2 mmol) as reagents. Loading (0.39 mmol/g) is determined by amino acid analysis. Unreacted residual amino groups on the polymer are capped by reacting with acetic anhydride and triethylamine (20 ml and 0.5 ml, correspondingly) in $CH_2Cl_2$ (10 ml). The peptide chain assembly is started with the Boc-Asp(OFm)-MBHA resin, following the protocol outlined in Table 1.

TABLE 1

Protocol for manual solid phase synthesis.

| Step | Reagent/Solvents | Time (min.) |
|---|---|---|
| 1 | TFA in $CH_2Cl_2$ (30% v/v) | 3 |
| 2 | ThA in $CH_2Cl_2$ (50% v/v) | 20 |
| 3 | $CH_2Cl_2$ | 5 × 2 |
| 4 | 3% DIEA in $CH_2Cl_2$ (v/v) | 5 |
| 5 | 3% DIEA in NMP (v/v) | 2 |
| 6 | NMP | 5 × 2 |
| 7 | Ninhydrin test | |
| 8 | 1.6 mmol Boc A.A. + 1.6 ml 1N HOBT + 1.6 ml 1N DCC all in NMP; preactivation - 30 min; filter and add solution to polymer (1 g) DMSO (final vol. 20% v/v) | 45<br>20 |
| 9 | DIEA (6 mmol in NMP) | 10 |
| 10 | NMP | 5 |
| 11 | $CH_2Cl_2$ | 3 × 2 |
| 12 | Ninhydrin test | |
| 13 | 10% $Ac_2O$ + 3% DIEA in $CH_2Cl_2$ | 5 |
| 14 | 10% $Ac_2O$ in $CH_2Cl_2$ | 10 |
| 15 | $CH_2Cl_2$ | 3 × 2 |

Solvents for all washings and reactions are measured to volumes of 10 ml/g resin. All couplings are performed using HOBT active esters of Boc-amino acid derivatives, prepared by DCC prior to each coupling step. A molar ratio of 4:1 of Boc-amino acid 1-hydroxybenzotriazole ester (Boc-AA-OBT) and α-amino group of a growing peptide chain, respectively, is employed for couplings. Coupling reactions are monitored by boiling a few mg (~3) of polymer in a solution of ninhydrin in pyridine-water for 2 min. Coupling of Boc-amino acids is repeated twice to ensure complete reaction. In the second coupling, half of the amount of Boc-AA OBT is used. As a rule, after completion of each coupling step, residual amino groups are capped by treating the resin with acetic anhydride (10%) and diisopropylethylamine (3%) in methylene chloride, followed by treatment with 10% acetic acid in methylene chloride.

Following completion of the peptide chain assembly, the t-Boc protecting group of Lys-1 is removed, as usual, by 50% TFA in $CH_2Cl_2$ and the newly free α-amino group is coupled to stearic acid (0.37 g, 2 mmol) using DCC (0.42 g, 2 mmol) and HOBT (0.27 g, 2 mmol) as reagents (Protocol). The reaction proceeds for 120 min and is repeated twice. The OFm and Fmoc side-chain protecting group of $Asp^6$ and $Lys^1$, respectively, are removed using 50% piperidine in DMF for 1 hr. Following extensive washings with DMF (3×10 ml), dichloromethane (3×10 ml), 10% DIEA in $CH_2Cl_2$ (3×10 ml), DMF (3×10 ml) and $CH_2Cl_2$ (3×10 ml), the resin is suspended in 7 ml DMF and mixed with five-fold excess (2 mmol) of (benzotriazolyloxy)tris(dimethyl) aminophosphonium hexafluorophosphate (BOP) reagent in the presence of seven-fold excess (2.8 mmol) of DIEA for 8 hr. Cyclization is repeated following the exact procedure. A negative ninhydrin test indicates completion of cyclization. The fully assembled cyclic peptide-resin is washed with $CH_2Cl_2$ according to protocol, then dried under vacuum overnight, over $P_2O_5$. Deblocking of protecting groups and cleavage of the peptide from resin is achieved by the anhydrous HF technique. Thus, the peptide-resin (1 g) is treated in a Teflon™ HF apparatus (Multiple Peptide System) with 9 ml HF in the presence of a mixture of 1.5 ml of p-thiocresol and p-cresol (1:1 v/v) for 1 hr at 0° C. The HF is removed by vacuum and the resin is extracted with peroxide-free ether (4×25 ml), filtered, dried and extracted with 50% acetic acid in water (3×25 ml). Lyophilization of aqueous filtrate yielded the crude powder of stearoyl-Lys-Lys-Lys-Tyr-Leu-Asp-NH2 (SEQ ID NO:70)

The crude product was dissolved in 50% aqueous acetic acid and passed through a Sephadex G-25 column (75×2 cm) employing 0.1 N acetic acid as an eluent. Elution was monitored spectrophotometrically at 274 nm. Lyophilization of the aqueous solution yielded the peptide free of aromatic additives added as scavengers at the HF-cleavage step. Yield was 50–70%.

Purification by high performance liquid chromatography (HPLC) is then carried out on the Sephadex-fractionated products. This can be performed, however, on the crude peptide. Purifications were achieved on a Merck RP-8 column (7 μM, 250×10 mm). The peptide is applied in 10% acetonitrile in water and eluted with a linear gradient established between 0.1% TEA in water and 0.1% TFA in 75% acetonitrile in water at a flow rate of 10 ml/min. Fractions are collected and cuts made after inspection by analytical HPLC. Derived fractions are pooled and lyophilized. Yield of the pure peptide is 30–35%.

Purity of the product is ascertained by analytical HPLC (Merck RP-8, 250×4 mm column) and amino acid analysis, following exhaustive acid hydrolysis (6 N HCl), which gives the expected values of each constituent amino acid.

Other related cyclic derivatives of formulae (iii) and (iv) above wherein Z is —NH—CO— or —CO—NH— are prepared by exactly the same process while employing the corresponding amino acid derivatives.

Alternatively, the cyclic derivatives may be prepared by the processes described above and then the stearoyl or other suitable lipophilic moiety is introduced into the molecule at the N terminal.

EXAMPLE B2

Synthesis of Stearoyl-Cys-Lys-Lys-Tyr-Leu-Cys-NH$_2$ (SEQ ID NO:71)
|_____|

[General formula (iii) above wherein X$_5$=Leu, X$_6$ is a covalent bond, Z=—S—S—; n=1, m=1]

Synthesis of the peptide is performed manually on a p-methylbenzhydrylamine (MBHA) resin (1 g) as outlined in the previous example. Cysteine residues, 1 and 6, are introduced into the peptide chain employing Boc-Cys(S-4-MeBzl)—OH as a building block. Following completion of the chain assembly and addition of N-terminal stearoyl moiety, the peptide-resin is treated with anhydrous HF as described above. The white powder of crude peptide obtained after lyophilization is dissolved in 0.1% acetic acid (~0.5 mg/ml) and the solution is de-aerated by bubbling through oxygen-free nitrogen for 2 hr. The pH of the solution is adjusted with concentrated aqueous NH$_4$OH to ~8.5 and a solution (~1 N) of K$_3$Fe(CN)$_6$ (2.5 equiv.) in water is slowly added dropwise. After complete addition of the oxidant reagent, the reaction mixture is allowed to stir for ~1 hr at room temperature. The solution is then concentrated by rotary evaporation and the crude cyclic product is fractionated on Sephadex G-25, as described above. Purification is then achieved by HPL-C on a Merck RP-8 column (see previous example). Yield of the pure product is 35–40%. Other cyclic peptides containing S—S internal bridges are prepared following the above procedure while employing Boc-Cys(S-4-MeBzl)-OH and Boc-Homocys(S-4-MeBzl)-OH as building blocks, which are introduced at sites selected for cyclization.

EXAMPLE B3

Synthesis of Stearoyl-Cys-Lys-Lys-Tyr-Leu-Lys-NH$_2$ (SEQ ID NO:72)
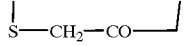

[General formula (iii) above wherein X$_5$=Leu; X$_6$=covalent bond: Z=—S—(CH$_2$)$_t$—CO—NH—; m=1; n=4; t=1]

Synthesis of the peptide is performed manually on a p-methylbenzhydrylamine (MBHA) resin (1 g) as outlined in the previous example. A cysteine residue 1 is introduced into the peptide chain employing Boc-Cys(S-4-MeBzl)-OH, while Lys-6 is introduced as Boc-Lys(ε-Fmoc)-OH. Following completion of the chain assembly and addition of N-terminal stearoyl moiety, the ε-Fmoc protecting group of Lys-6 is removed by treatment with 20% piperidine in DMF for 30 min. Extensive washings of the resin are then performed with DMF (3×10 ml), CH$_2$Cl$_2$ (3×10 ml), 10% DIEA in CH$_2$Cl$_2$ (3×10 ml), DMF (3×10 ml) and CH$_2$Cl$_2$ (3×10 ml). The resin is suspended in 10 ml of DMF and mixed with five-fold excess (2 mmol) of bromoacetic acid anhydride for 6 hr. The resin is washed with DMF (3×10 ml) and the reaction repeated. Negative ninhydrin test indicates completion of the acylation reaction. The resin is then washed with DMF (3×10 ml), and CHCl$_2$ (3×10 ml), dried in vacuo and treated with anhydrous HF using anisole (10%) as the only scavenger. A crude bromoacetylated product is obtained using the same manipulations described in previous examples. The white powder (~0.5 mg/ml) is then dissolved in 0.1% acetic acid and the pH is adjusted to ~7.0 by 1 N NaOH. After reacting for 4 hr at room temperature, the solution, devoid of free SH-functions as indicated by Ellman's Reagent (Aldrich), is concentrated by rotary evaporation. The crude product is then purified by being passed through a Sephadex G-25 column, followed by preparative HPLC, as described in Example A. Yield of the pure product is 25–30%. Other cyclic peptides containing internal —S—(CH$_2$)$_t$—CO—NH— or —NH—CO—(CH$_2$)$_t$—S— bridges are prepared following the above procedure while employing, at the site selected for cyclization and elsewhere, the corresponding amino acid derivatives.

C. The Neurodegenerative Treatment Aspen of the Invention

EXAMPLE C1

Biological Test—Effect of Conjugates of the Invention on the Survival of β-Amyloid Peptide Treated Neurons Method β-Amyloid peptide is known to be involved in Alzheimer's disease and is a toxic substance to neurons grown in culture (Pike et al., *J. of Nezarosci.*, 13(4), 1676–1687 (1993); Yankner et al., *Science*, 250:279–282 (1990); Gozes et. al., *Proc. Natl. Acad. Sci. USA*, 93:927–432 (1996)).

Rat cerebral cortical cell cultures were prepared by a slight modification of the techniques described by Forsythe and Westbrook (*J. Physiol. Lord.* 365:515, (1988)), in which cerebral cortex was used instead of hippocampus and newborn rats were utilized instead of E16 mice. Cerebral cortical cells (1.5–15×10$^5$ cells/35 mm dish) were plated on confluent cerebral cortical astrocyte feeder cultures as described (Gozes et al., *J. Pharmacol Erp. Therap.*, 257:959–966 (1991)). The culture medium was DMEM-(Dulbeco Modified Eagle Medium) containing 5% horse serum and N3 [media supplement containing a hormone cocktail, according to (Romijn et al., *Brain Res.*, 254:(4),583–589 (1981))]. After eight days growth in vitro, the cultures were given a complete change of medium and then were treated with the β-amyloid peptide (amino acids 25–35) for 5 days.

The β-amyloid peptide fragment was dissolved in water to a finalconcentration of 2.5 mM. Experiments were performed with increasing, doses of the conjugates of the invention (1 mg initially mixed with 10 μl DMSO and then with a further 10 μl of DMSO to achieve complete solubilization and diluted in PBS to obtain a stock solution of 10$^{-3}$ M) that were added together with 25 μM β-amyloid peptide (amino acids 25–35) to dissociated cerebral cortical cells, nine days after plating of neurons. Ten μl of conjugate solution was added to 1 ml culture medium. The duration of treatment was 5 days with no change of media. After 14 days in culture, cells were fixated for immunocytochemistry and stained with antibodies against NSE (neuron specific enolase, a neuronal marker). Neuronal cell counts were executed on 60 fields. with a total area of 25 mm$^2$. Neurons were counted without knowledge of type of treatment as before. Each value is the mean±SEM of 3 dishes.

The results are shown in FIG. 1 and Table 2. FIG. 1 shows the summation of five independent experiments, with the control containing 164, 225, 130, 319, 172 neurons. As can be seen in FIG. 1, St-Lys-Lys-Tyr-Leu-NH$_2$ is a very active conjugate exhibiting activities at 10$^{-13}$–10$^{-9}$ M with a peak activity at 10$^{-12}$–10$^{-10}$ M. The cell count of cells treated with both this conjugate and β-amyloid peptide was higher than the counts of untreated control cells indicating that this conjugate was able to protect cells also against naturally occurring death.

TABLE 2

Peptide Activity in the neuronal survival assay, protection against β-amyloid toxicity:

| | Peptide | SEQ. ID NOS | Active concentration (M) | Neuronal survival (%) | % survival after β-amyloid | Concentration tested |
|---|---|---|---|---|---|---|
| 1 | St-Lys-Lys-Tyr-Leu-NH$_2$ | 6 | $10^{-13}$–$10^{-9}$ | 80–110 | 52 | $10^{-13}$–$10^{-9}$ |
| 2 | St-Lys-Lys-Tyr-Val-NH$_2$ | 9 | $10^{-13}$ | 72 | 38 | $10^{-13}$–$10^{-9}$ |
| 3 | St-Lys-Lys-Tyr-D-Ala-NH$_2$ | | $10^{-15}$–$10^{-12}$ | 67–117 | 44 | $10^{-15}$–$10^{-11}$ |
| 4 | St-Lys-Lys-Tyr-Nle-NH$_2$ | 16 | $10^{-14}$–$10^{-12}$ | 76–84 | 44 | $10^{-15}$ $10^{-11}$ |
| 5 | Lau-Lys-Lys-Tyr-Leu-NH$_2$ | 14 | $10^{-11}$–$10^{-10}$ | 83–84 | 63 | $10^{-13}$–$10^{-9}$ |
| 6 | Cap-Lys-Lys-Tyr-Leu-NH$_2$ | 15 | $10^{-11}$ | 73 | 63 | $10^{-13}$–$10^{-8}$ |
| 7 | St-Lys-Tyr-Leu-NH$_2$ | | $10^{-11}$ | 96 | 53 | $10^{-13}$–$10^{-9}$ |
| 8 | St-Val-Lys-Lys-Tyr-Leu-NH$_2$ | 17 | $10^{-12}$–$10^{-8}$ | 70–92 | 53 | $10^{-13}$–$10^{-8}$ |
| 9 | St-Lys-Lys-Tyr-Leu-Nle-NH$_2$ | 10 | $10^{-13}$–$10^{-10}$ | 95–100 | 36 | $10^{-13}$–$10^{-9}$ |
| 10 | St-Lys-Lys-Tyr-Leu-Asn-NH$_2$ | 20 | $10^{-13}$–$10^{-10}$ | 52–73 | 34–57 | $10^{-13}$–$10^{-9}$ |
| 11 | St-Lys-Lys-Tyr-Leu-Asn-Ser-NH$_2$ | 21 | $10^{-13}$ | 83 | 52 | $10^{-13}$–$10^{-9}$ |
| 12 | St-Lys-Lys-Tyr-Leu-Asn-Ser-Ile-NH$_2$ | 22 | $10^{-9}$ | 123 | 57 | $10^{-13}$–$10^{-9}$ |
| 13 | St-Lys-Lys-Tyr-Leu-Asn-Ser-Ile-Leu-NH$_2$ | 23 | $10^{-9}$ | 97 | 57 | $10^{-13}$–$10^{-9}$ |
| 14 | St-Asn-Ser-Ile-Leu-Asn-NH$_2$ | 8 | $10^{-11}$ $10^{-10}$ | 68–103 | 40 | $10^{-13}$–$10^{-9}$ |
| 15 | St-Ser-Ile-Leu-Asn-NH$_2$ | 25 | $10^{-12}$–$10^{-9}$ | 84–58 | 40 | $10^{-13}$–$10^{-9}$ |
| 16 | St-Leu-Asn-Ser-Ile-Leu-Asn-NH$_2$ | 73 | $10^{-13}$–$10^{-11}$ | 100–114 | 58 | $10^{-13}$–$10^{-9}$ |
| 17 | St-Tyr-Leu-Asn-Ser-Ile-Leu-Asn-NH$_2$ | 19 | $10^{-13}$–$10^{-11}$ | 88–110 | 58 | $10^{-13}$–$10^{-9}$ |

As can be seen in Table 2, several modifications of the St-Lys-Lys-Tyr-Leu-NH$_2$ (SEQ ID NO:6) conjugate (1) showed similar activity in protection of neurons from death caused by β-amyloid as compared to control. In some cases (where neuronal survival exceed 100% as compared to control) the conjugates were able to protect also against naturally occurring death. Notably substitution of Leu of conjugate 1 by Val (3), D-Ala (3), Nle (4), addition of amino acid residues at the N-terminal (8) or C-terminal (9,10,11, 12,13), deletion of amino acid residues from the N-terminal (7) or replacement of the lipophilic moiety Stearoyl by Lauroyl (Lau), (5) or Caproyl (Cap,6) resulted in conjugates with activity similar to St-Lys-Lys-Tyr-Leu-NH$_2$ (SEQ ID NO:6).

EXAMPLE C2

Effects of a Conjugate of the Invention on Learning and Memory in Animal Models of Alzheimer (Morris Water Maze)

In vivo Model for Cholinergic Inhibition. 18 Male rats (Wistar, 250–300 g) were injected intracerebroventricularly (i.c.v.) at a rate of 0.21 µl/min., using plastic tubing (PE-20) attached to 25G needle; controls received an injection of saline 2 µl/side, experimental animals received injections of the cholinergic blocker (ethylcholine aziridium) AF64A (3 nmol/2 µl/side).

Drug treatment was initiated 7–10 days after AF64A injection. Animals were divided into two equal groups. Test group received daily nasal administration of St-Lys-Lys-Tyr-Leu-NH$_2$ (SEQ ID NO:6) dissolved in 10% Sefsol™ and 40% isopropanol at a concentration of 10 µg/40 µl (20 µl administered through each nostril). Control animals received intranasal administration of the vehicle. The rats were partially anesthetized by diethylether prior to nasal administration. Following seven days of drug administration, behavioral assays were conducted for an additional 10 days. Drugs were applied by nasal administration 1 hour prior to testing. All animals were chronically treated (every two days) with 50,000 units of durabiotic antibiotics to avoid infection.

Learning test procedure was carried out according to the Morris Water Maze procedure (Morris et al., *Nature,* 297:681–683, 1982; Morris et al., *Nature,* 319:774–776, 1986).

1. Administration of St-Lys-Lys-Tyr-Leu-NH$_2$ (SEQ ID NO:6)

Rats were placed in a circular pool, 1.26 m in diameter, 0.2 m deep, equipped with a clear plexiglas column, with a 13.3 cm platform reaching just below the surface of the water (22–24° C). Drugs were applied daily by nasal administration 1 hour prior to testing. The latency of reaching the platform was recorded for each rat (in seconds) and the changes over days of training were graphed, which reflect learning and memory.

Figure 2:
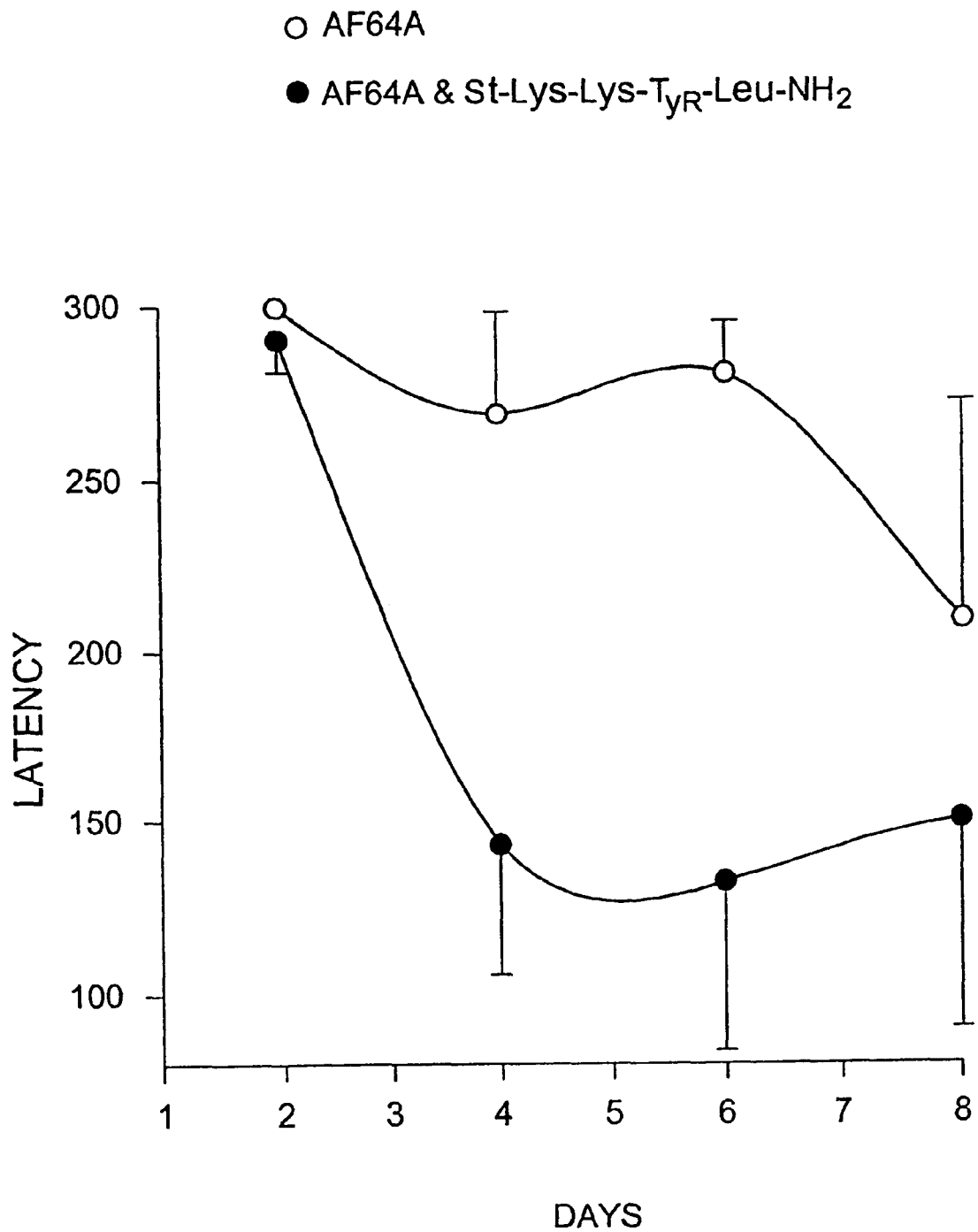
FIG. 2 shows the effect of the cholinergic blocker AF64A (○) and of AF64A together with St-Lys-Lys-Tyr-Leu-NH$_2$ SEQ ID NO:6) (●) on learning and memory in an animal model of Alzheimer.

As can be seen in FIG. 2, control animals injected with AF64A (○) showed a smaller improvement in the latency of reaching the platforms compared with animals injected with AF64A and nasally administered with St-Lys-Lys-Tyr-Leu-NH$_2$ (SEQ ID NO:6) (●). These results indicate that the conjugate of the invention is able to improve learning and memory in an animal model of Alzheimer.

II. Administration of St-Lys-Lys-Tyr-D-Ala-NH$_2$

Figure 3:
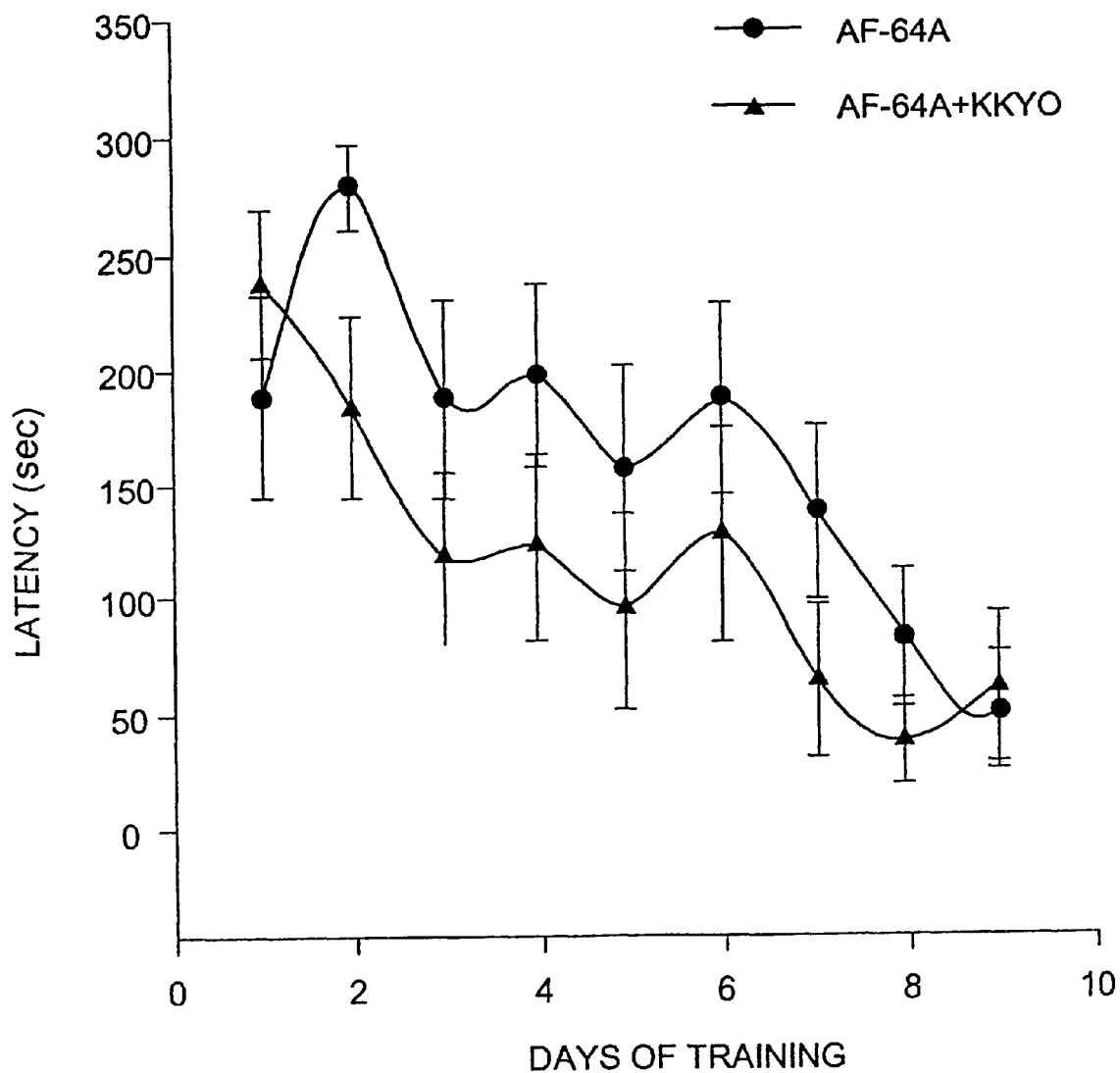
FIG. 3 shows the effect of the cholinergic blocker AF64A (e) and of AF64A together with St-Lys-Lys-Tyr-D-Ala-NH$_2$ (▲) on learning and memory in an animal model of Alzheimer.
Figure 4:
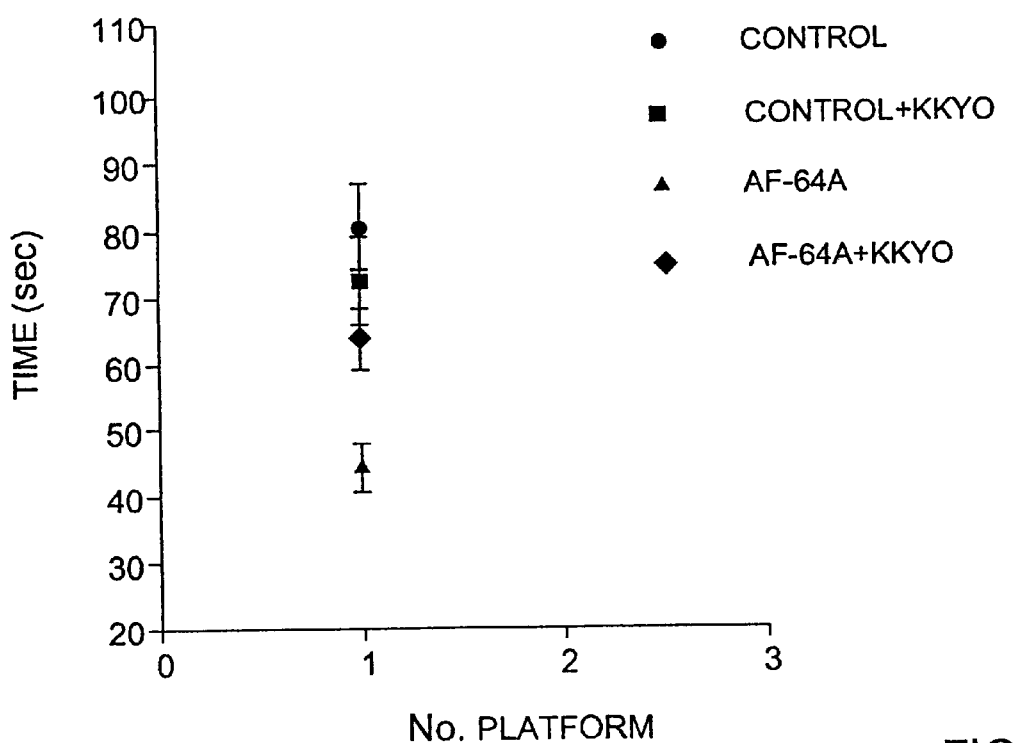
FIG. 4 shows the effect of administration of saline control (○); saline together with St-Lys-Lys-Tyr-D-Ala-NH$_2$ (■); the cholinergic blocker AF64A (▲) and AF64A together with St-Lys-Lys-Tyr-D-Ala-NH$_2$ (♦) on memory retention in an animal model of Alzheimer.
Figure 5:
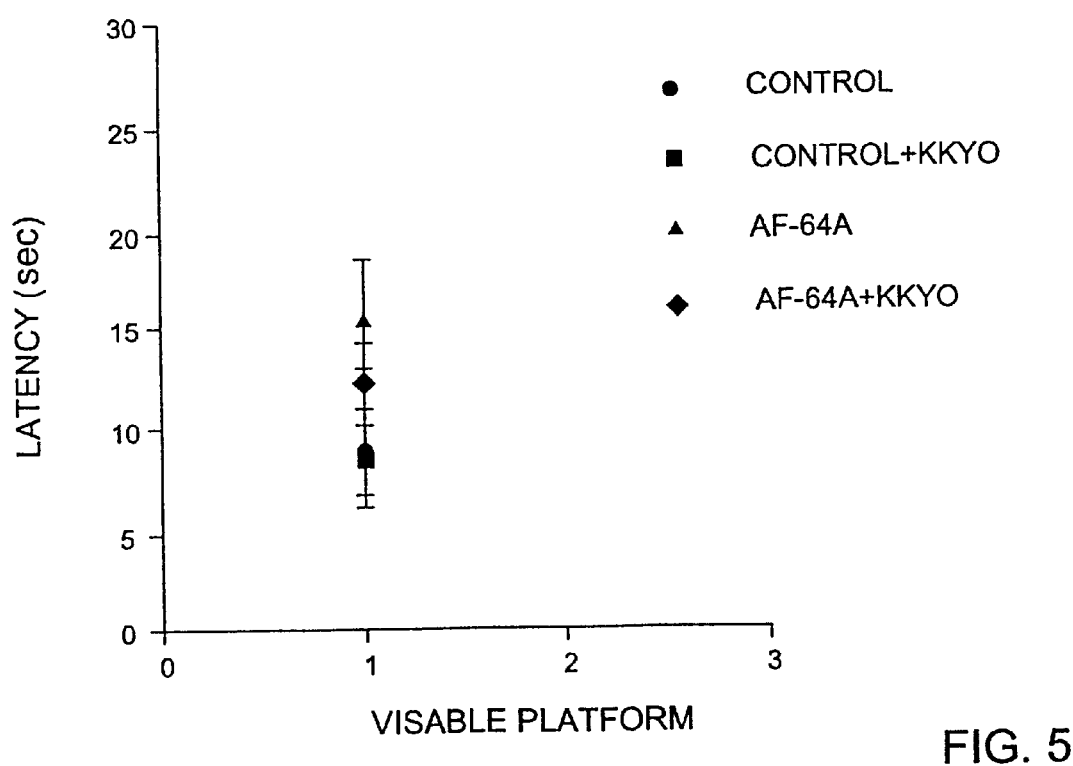
FIG. 5 shows motor function of animals treated with saline (●); saline and St-Lys-Lys-Tyr-D-Ala-H$_2$ (■); the cholinergic blocker AF64A (▲) and animals treated with AF64A together with St-Lys-Lys-Tyr-D-Ala-NH$_2$ (♦)

FIG. 3 depicts the effects of St-Lys-Lys-Tyr-D-Ala-NH$_2$ (indicated KKYO in the figure) on learning and memory in the Alzheimer's in vivo test (AF64A-cholinotoxicity test) as described above. The results obtained were similar to those described above with control animals which were treated only with AF64A (●) showed smaller improvement in the latency of reaching the platforms compared with animals nasally administered also with St-Lys-Lys-Tyr-D-Ala-NH$_2$ (▲). An additional probe test was also performed (Gozes et al., *Proc. Nat. Acad. Sci. USA* 93:427–432, 1996), in this test: after the animals know where the platform is in the water pool, the platform is removed and the time the animals spend in the area occupied before by the platform is recorded, this time periods represents memory retention of a previously studied test. As observed in FIG. 4, St-Lys-Lys-Tyr-D-Ala-NH$_2$ treated animals exhibit better memory retention than the AF64A treated animals that did not receive the peptide. Following this test the platform is placed back in the water pool, but this time it is visible to the swimming rat and the time required to reach it is measured. In this case the parameter measured is possible motor deficits. As can be seen in FIG. 5, there are no differences between the groups, thus overall, the test measured learning and memory and not motor changes.

Figure 6:
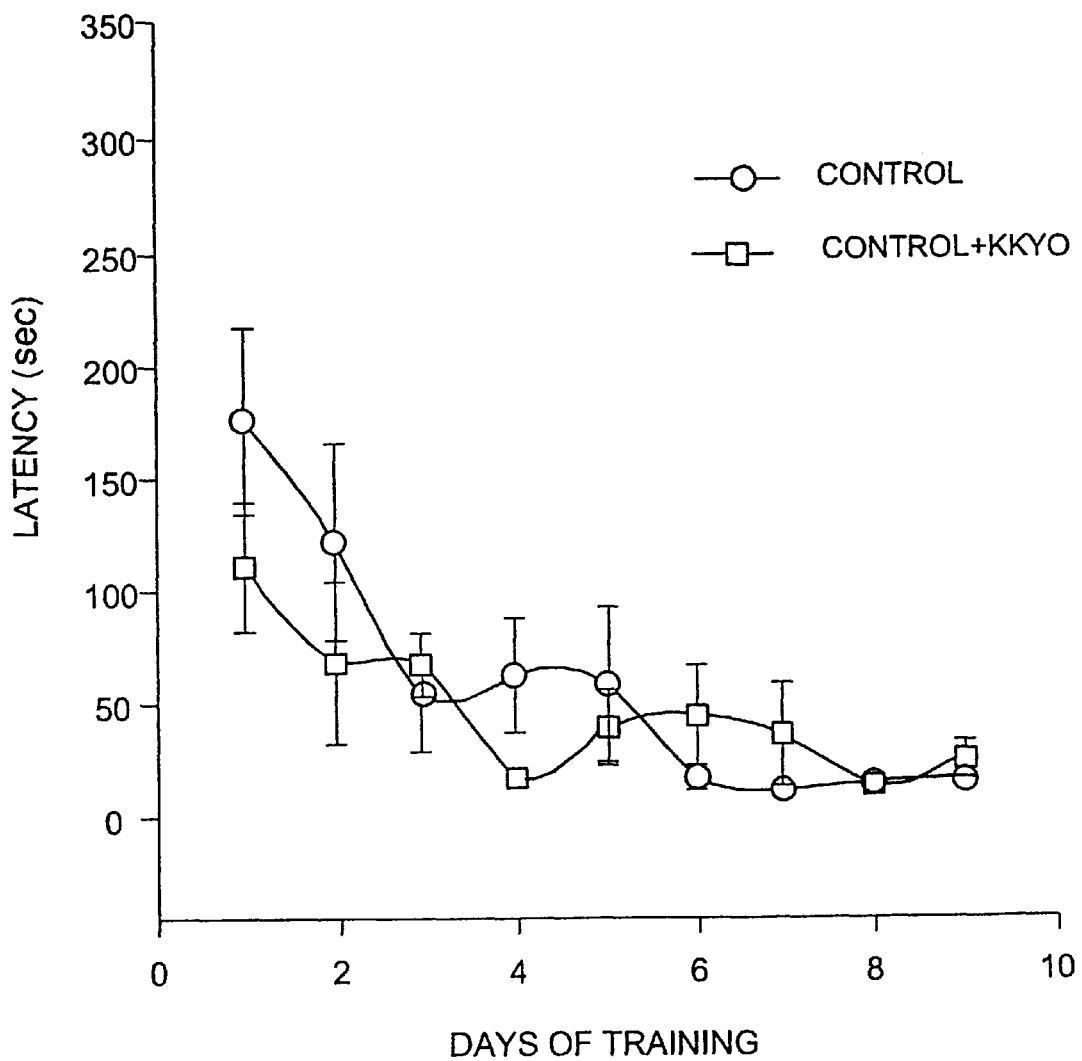
FIG. 6 shows the effect of administration of saline (○) and the conjugate St-Lys-Lys-Tyr-D-Ala (□) on learning and memory in normal control animals administered with the vehicle.

EXAMPLE C3
Effects of a Conjugate of the Invention on Learning and Memory of Normal Animals The experiment described in Example C2 was repeated but the animals were injected with saline instead of with AF64A and thus were normal animals, not featuring Alzheimer-like cognitive damages. The animals were divided into two groups, one administered intranasally only with the vehicle (Sefsol+isopropanol as described above) and one receiving intranasal administration of St-Lys-Lys-Tyr-D-Ala-NH$_2$. As can be seen in FIG. 6, an apparent somewhat faster learning was observed in the peptide treated group indicating a possible improvement of cognitive function also in undamaged, normal animals.

Figure 7:
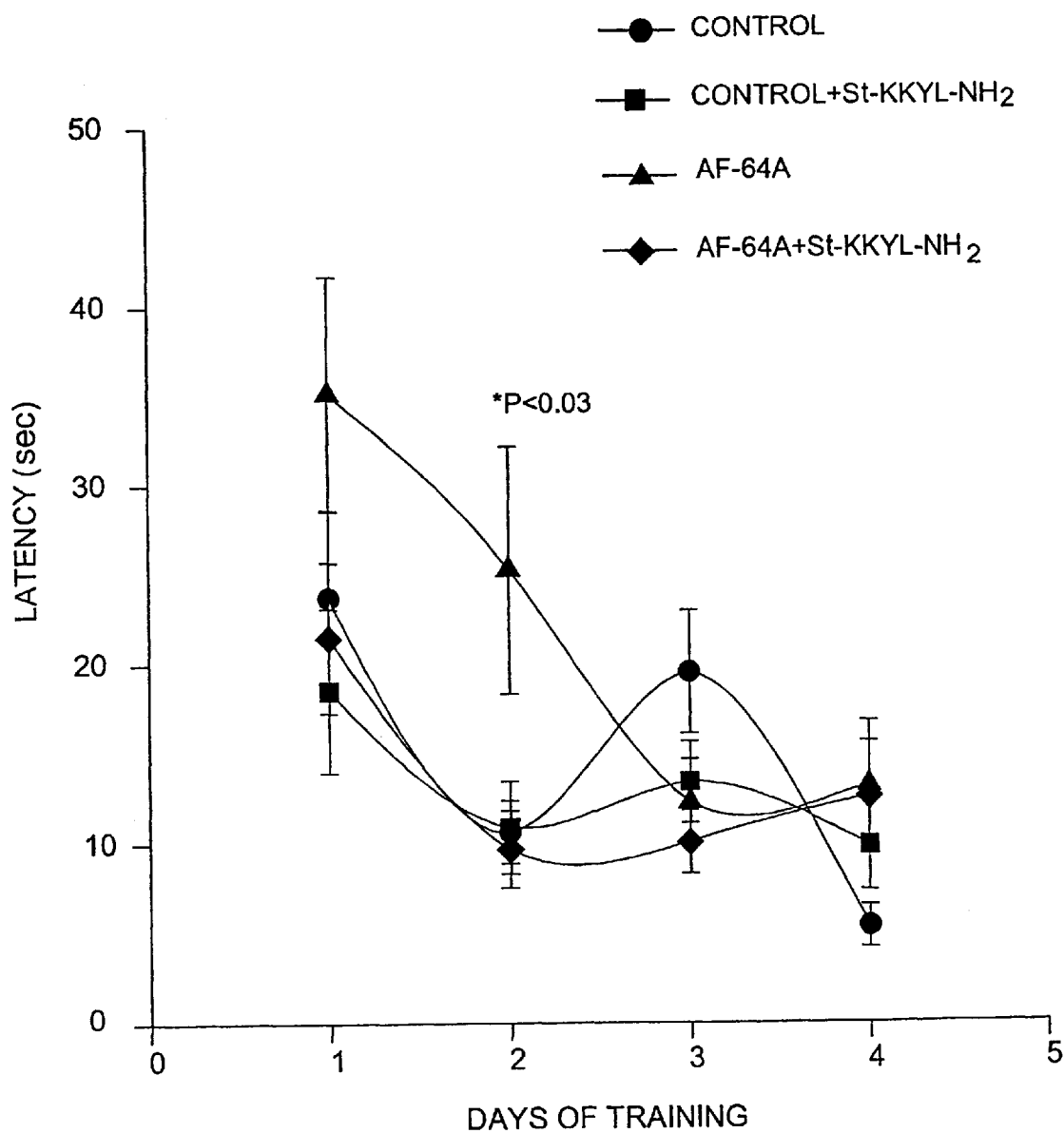
FIG. 7 shows the effect of administration of saline (●); saline and St-Lys-Lys-Tyr-Leu-NH$_2$ (SEQ ID NO:6) (■); the cholinergic blocker AF64A (▲) and AF64A together with St-Lys-Lys-Tyr-Leu-NH$_2$ (SEQ ID NO:6) (♦) on memory retention of a previously learned task in an animal model of Alzheimer (first swim)

EXAMPLE C4
Effects of a Conjugate of the Invention on a Model for Memory Retention A new model was developed in order to assess the capability of animals to retain the memory of a previously learned test. Animals (N=5–10) were first taught to find a submerged platform in a water maze as described above. For assessment of memory retention, the animals were subjected to daily swim (a test a day) in order to learn to find the hidden platform. After a week, the animals which showed the highest score in the study test, were chosen for the experiment. AF64A or saline were injected into the third ventricle of the brain and following a week of recuperation, the animals were treated by intranasal administration of the peptide St-Lys-Lys-Tyr-Leu-NH$_2$ (SEQ ID NO:6) as described above. Following a week of peptide treatment, the animals were tested again in the water maze and the experiment of retention of the learned task (i.e. finding the platform) was repeated as follows: the animal was placed on a platform for 1 min. And then placed in the water for swimming to the platform and the time required to reach the platform was measured. The results of the first swim are summarized in FIG. 7. As can be seen in the figure, it is evident that animals treated with the peptide are protected from memory loss, and are capable of retaining the memory of the task studied previous to the injection with AF64A since they behave in a similar manner to control.

Figure 8:
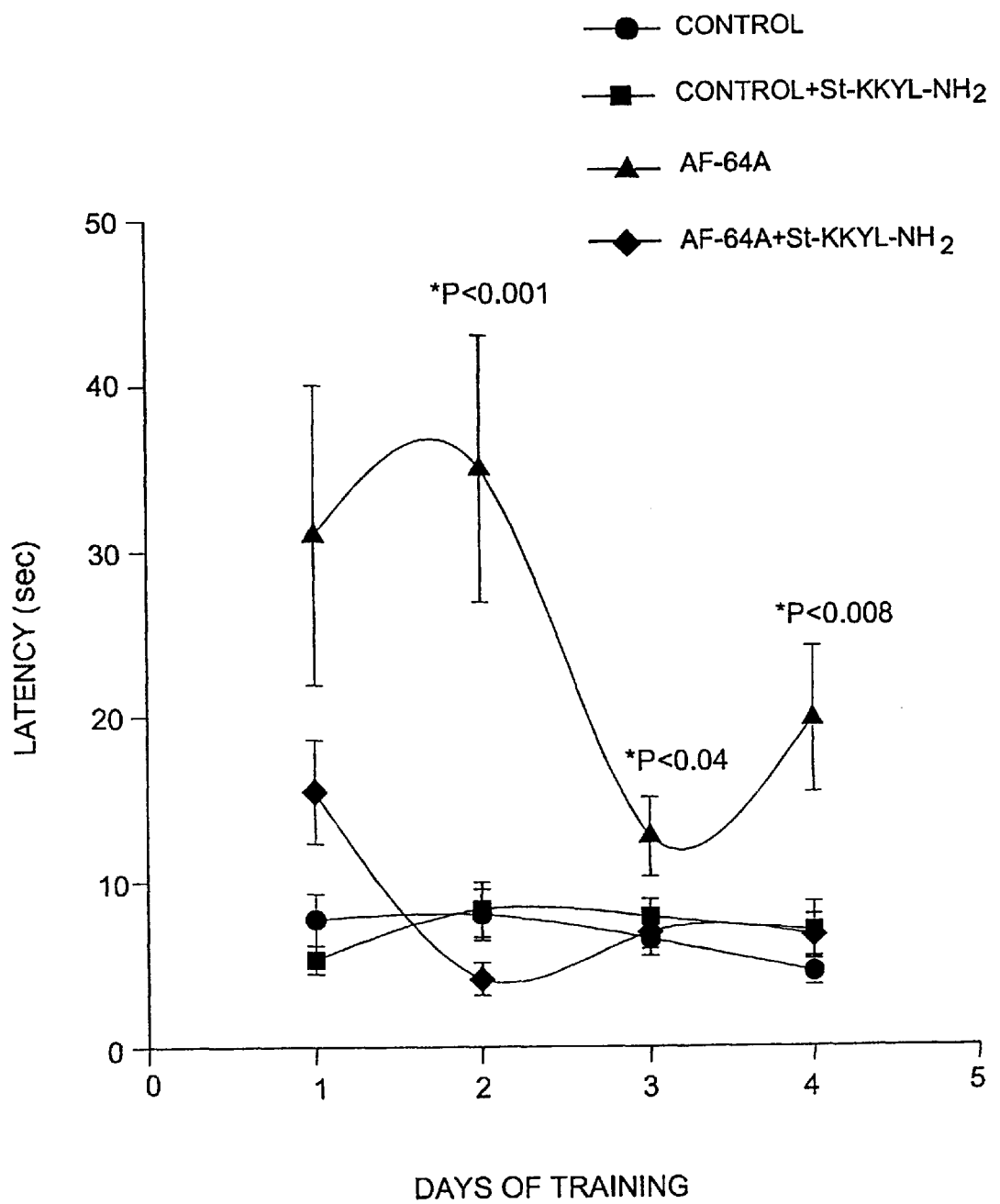
FIG. 8 shows the same experiment as described in connection with FIG. 7 for the second swim including administration of saline and St-Lys-Lys-Tyr-Leu-NH$_2$ (SEQ ID NO:6); and of AF64A together with St-Lys-Try-Leu-NH$_2$ (SEQ ID NO:6)

After 1 min. on the platform, the animal is placed back in the water for an additional swim and search of the hidden platform. FIG. 8 shows the result for the second swim. As can be seen, FIG. 8 also shows an improvement in learning and memory in animals treated with the peptide. This model, is the first demonstration of the activity of the peptide and facilitating memory retention.

Figure 9:
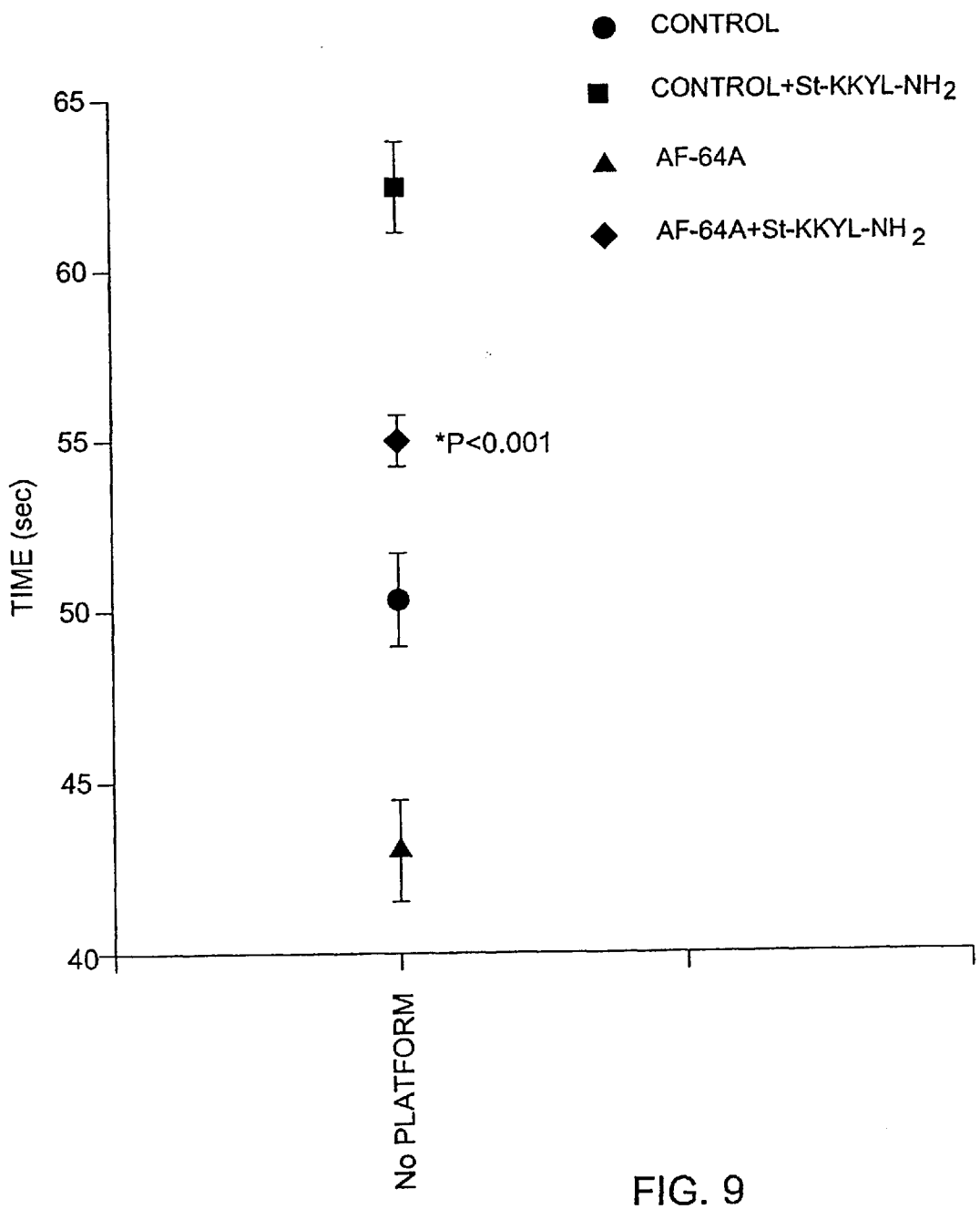
FIG. 9 shows the same experiment as described in connection with FIG. 7 measuring the time spent by the animals in the area where the platform used to be.

Finally, the platform is removed and the time spent by the animals at the area where the platform is featured in FIG. 9. The results summarized above, clearly demonstrate that St-Lys-Lys-Tyr-Leu-NH$_2$ (SEQ ID NO:6) is involved in learning, in working memory, and in memory retention.

EXAMPLE C5
Effect of Conjugates of the Invention on a Model for Mental Retardation A Model for Mental Retardation: Apolipoprotein E-deficient Mice It has recently been discovered that mice deficient in apolipoprotein E (ApoE) (Plump et al., *Cell*, 71:343–363 (1992)) are retarded in their acquisition of developmental milestones. The ApoE deficient mice were tested for the development of behavioral milestones and were found to be significantly retarded in their acquisition of forelimb placing behavior (postnatal day 11–13) as compared to control animals (postnatal day 2–5). A two day delay in the acquisition of cliff aversion behavior also was observed in these mice.

8 newborn normal mice were injected (s.c. 1.2 μg 120 μu) with St-Lys-Lys-Tyr-Leu-NH$_2$ or with saline. 8 ApoE deficient newborn mice were treated similarly.

Figure 10:
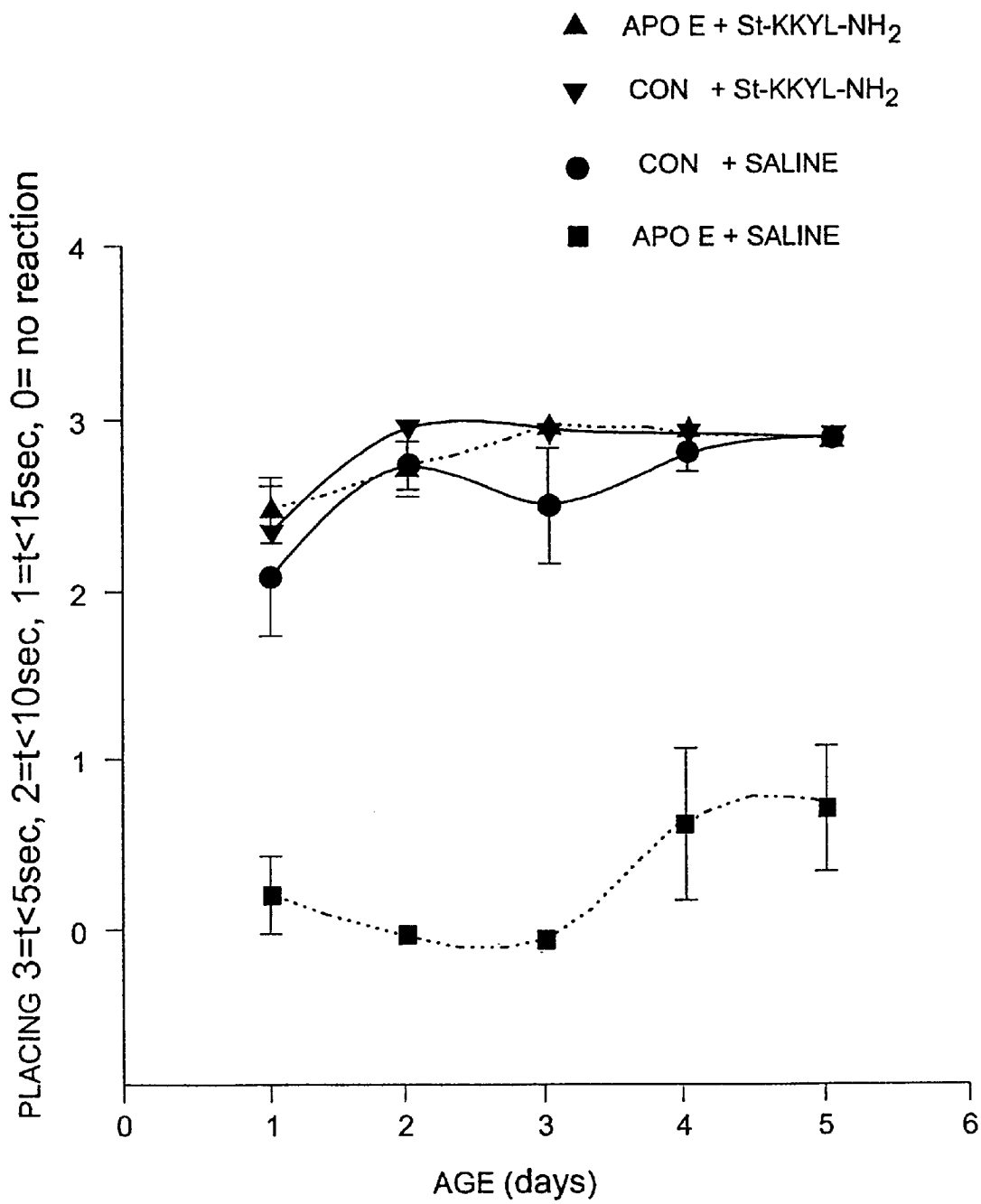
FIG. 10 shows the effect of St-Lys-Lys-Tyr-Leu-NH$_2$ (St-KKYL-NH$_2$ (SEQ ID NO:6) and saline on forelimb placing behavior acquisition in normal newborn mice (St-Lys-Lys-Tyr-Leu-NH$_2$ (SEQ ID NO:6) (▲); saline (○)), and on ApoE deficient newborn mice (APO E); (St-Lys-Lys-Tyr-Leu-NH$_2$ (SEQ ID NO:6) (▲); saline (●)).
Figure 11:
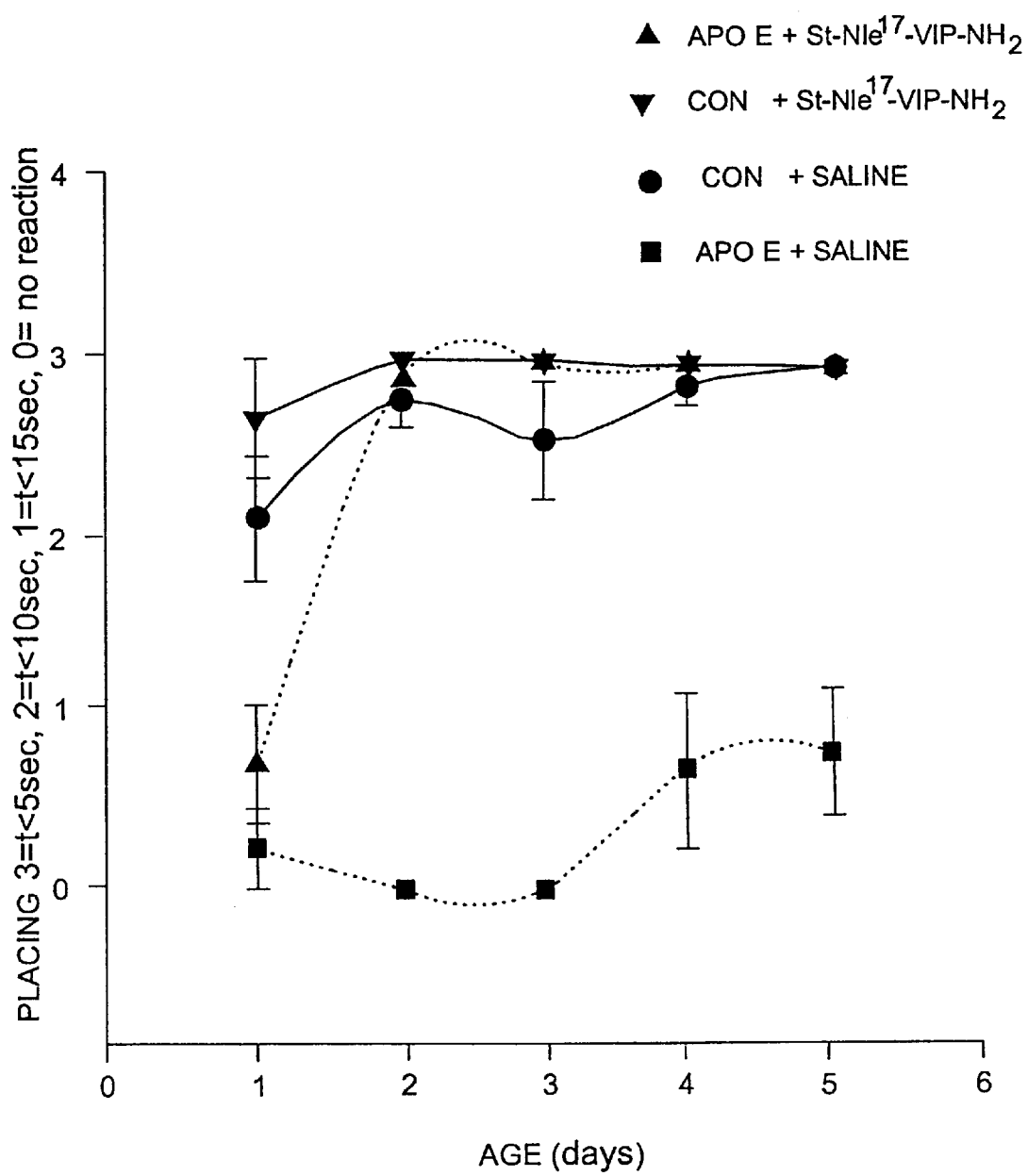
FIG. 11 shows for comparison the effect of St-Nle$^{17}$-VIP-NH$_2$ and saline on forelimb placing behavior acquisition in normal newborn mice (St-Nle$^{17}$-VIP-NH$_2$ (▼); saline (●), and on ApoE deficient newborn mice (St-Nle$^{17}$-VIP-NH$_2$ (▲); saline (♦))

The results of forelimb placing behavior acquisition are shown in FIGS. 10 and 11. As can be seen ApoE deficient mice treated with St-Lys-Lys-Tyr-Leu-NH$_2$ (SEQ ID NO:6) or with the known St-Nle$^{17}$-VIP-NH$_2$ (shown for comparison only) St-Nle$^{17}$-VIP improved their placing acquisition essentially to the level of control as compared with untreated ApoE deficient mice.

Figure 12:
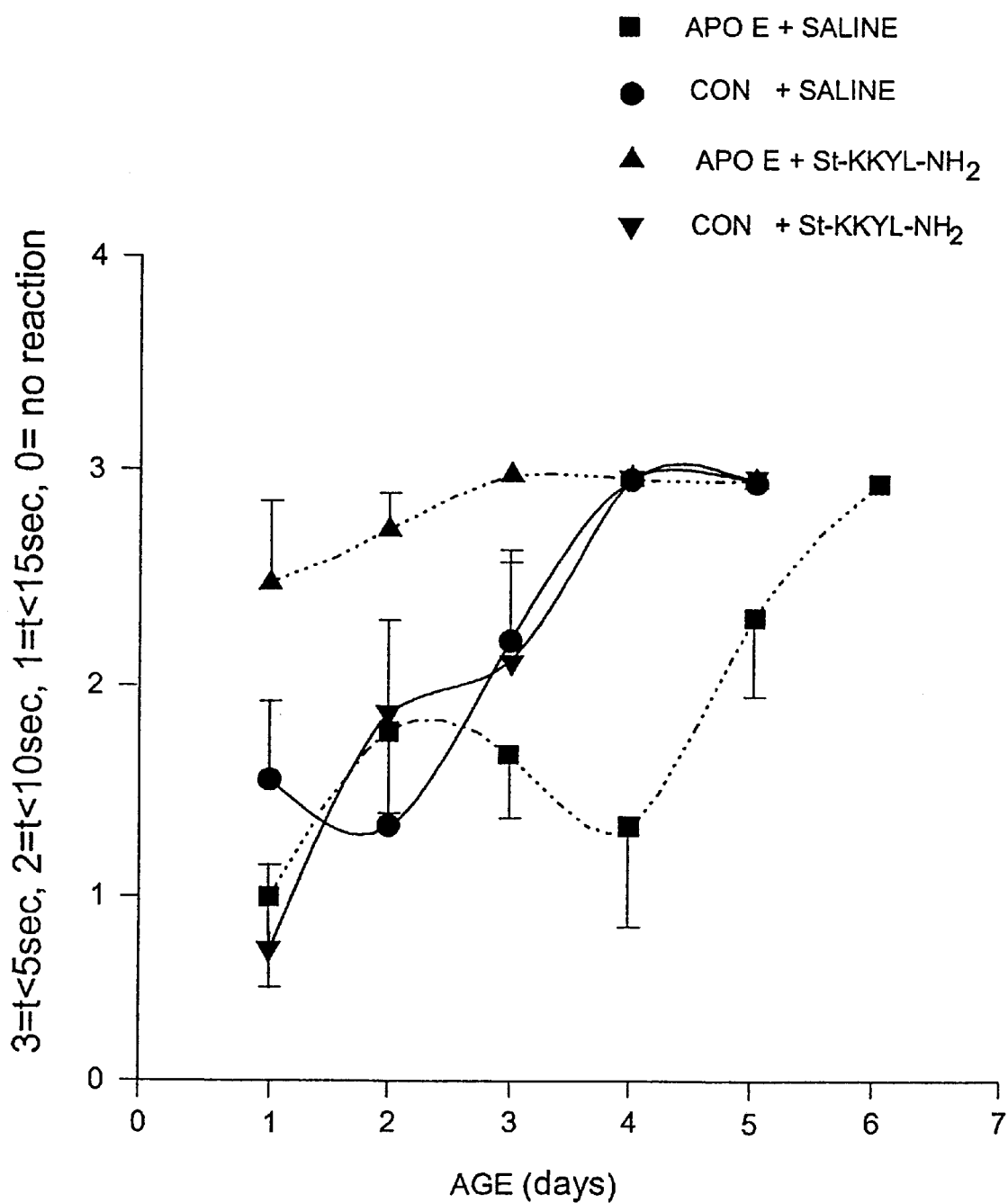
FIG. 12 shows the effect of St-Lys-Lys-Tyr-Leu-NH$_2$ (SEQ ID NO:6) (St-KKYL-NH$_2$) and saline on cliff avoidance acquisition in normal newborn mice (St-Lys-Lys-Tyr-Leu-NH$_2$ (SEQ ID NO:6), (▼); saline. (●)); and ApoE deficient mice (St-Lys-Lys-Tyr-Leu-NH$_2$ (SEQ ID NO:6) (▲); saline (♦))
Figure 13:
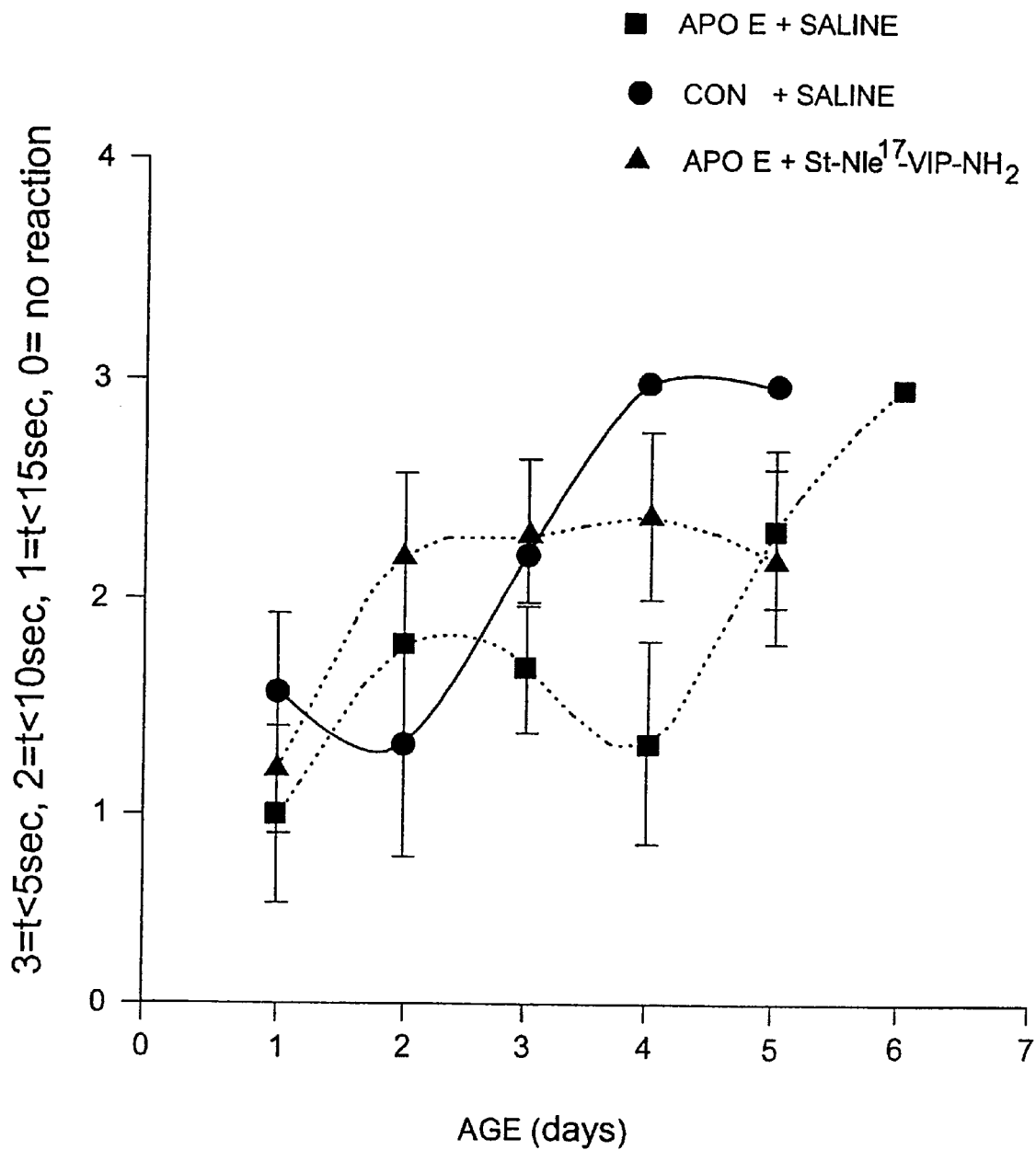
FIG. 13 shows for comparison the effect of St-Nle$^{17}$-VIP-NH$_2$ on cliff avoidance acquisition in normal newborn mice and ApoE deficient mice.

FIGS. 12 and 13 show cliff avoidance acquisition in animals treated as above. As can be seen, ApoE deficient mice treated with St-Lys-Lys-Tyr-Leu-NH$_2$ (SEQ ID NO:6) or St-Nle-V1P -NH$_2$ (shown for comparison only) showed even better cliff avoidance acquisition than normal controls or similar cliff avoidance behavior to control.

EXAMPLE C6
Effect of a Conjugate of the Invention on the Cholinergic Activity in Apolipoprotein E Deficient Mice Apo-E deficient mice were assayed for their cholinergic activity as described by Fonnum, F. A., *J Neurochem.*, 24:413–415, 1975. Briefly, brains from 21 days normal (control) and ApoE-deficient mice were assessed by measuring their Chat activity. Choline acetyl transferase (Chat) activity was determined as described before (see text), by measurements of the rate of synthesis of (14Cqacctylcholine from choline and [14C]acetylCoA. Non-specific background was measured in the absence of choline. Each brain (300–400 mg) was homogenized in a teflon homogenizer, with 10 volumes of 50 mM phosphate buffer (pH=7.4) containing 300 mM NaCl, 30 mM EDTA and 0.5% triton. The homogenates were centrifuged at 12000 g for 15 min., and 10 141 of the supernatant (in triplicates) were mixed with 10 μl of a solution containing: 14 μM 14C-acetyl-CoA (56 mCi/mmol NEN), 20 mM Acetylcholine, 1.6 mM choline chloride, 0.25 mM eserine, and phosphate buffer. The reaction was carried out at 37° C. for 15 min. stopped by adding 50 μl of 15 mg/ml tetraphenylboron prepared in 3-heptanone and mixed in a vortex for 30 sec. Twenty μl of the organic phase were collected after 2 min. microfuging, then were mixed with scintillation liquid and radioactivity was measured in a beta-counter.

Experiments were conducted on 21-day-old animals chronically injected with peptides or with saline. Injection is performed subcutaneously, peptides are dissolved (100 μg/30 μl) in DMSO and diluted with saline to obtain the desired concentrations. Day 1–4: 4 μg peptide/20 μl saline; day 5–10: 8 μg/40 μl saline; day 11–14: 16 μg/80 μl saline.

Figure 14:
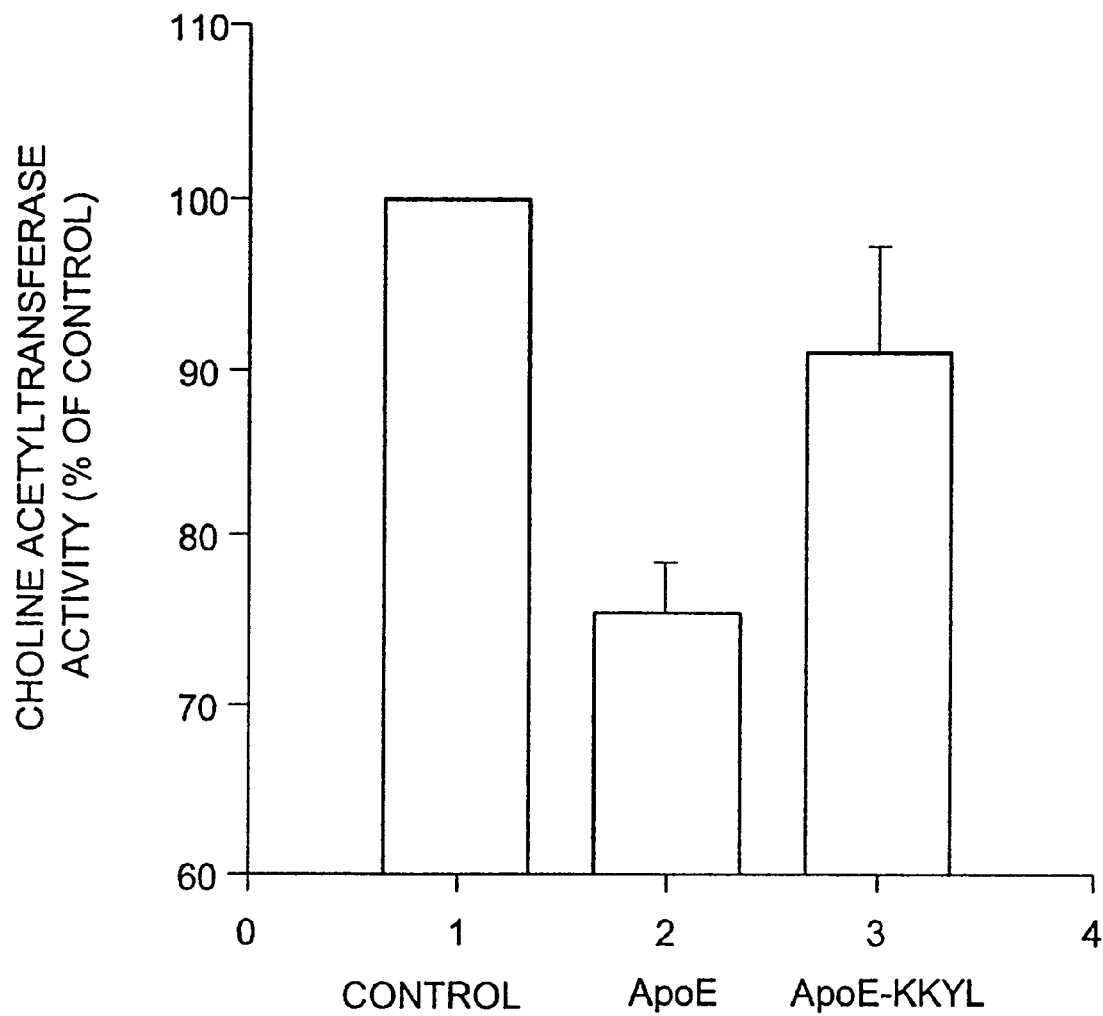
FIG. 14 shows the Choline Acetyl transfcrasc activity of control, and Apo-E deficient mice treated with St-Lys-Lys-Tyr-Leu-NH$_2$ (SEQ ID NO:6)

The results of cholinergic activity show a reduction in Apo-E deficient mice. The cholinergic activity of mice administered with St-Lys-Lys-Tyr-Leu (SEQ ID NO:6), are shown in FIG. 14. The figure demonstrates ApoE mice treated with St-Lys-Lys-Tyr-Leu-NH$_2$ (SEQ ID NO:6) which show an increase in choline acetyl transferase activity as compared to the control levels.

FIG. 14 indicate that St-Lys-Lys-Tyr-Leu-NH$_2$ (SEQ ID NO:6) increases cholinergic activity in the apolipoprotcin E deficient mice (100% activity indicates 669–758 pmole/mg, protein/min. in all the determinations of choline acetyl transferase activity).

EXAMPLE C7
Biodistribution of St-Lys-Lys-Tyr-Leu-NH$_2$ (SEQ ID NO:6)

St-Lys-Lys-Tyr-Leu-NH$_2$ (SEQ ID NO:6) was radioiodinated by using the chloramine T methods as described in Gozes et al., *Endocrinology*, 134:2121–2125 (1994) and about 7.8×10$^6$ cpm/2 μl 5% Sefsol™, 20% isopropanol/rat were applied intranasally to 250–300 g rats. Animals were sacrificed 30 minutes following drug administration and the frontal cortex was removed, weighed and counted for radioactivity in a gamma counter. Radioactive tissue samples (containing 1400 cpm/gram sample) were thereafter homogenized and subjected to centrifugation (5,400 g for 25 min.). Supernatants were then subjected to HPLC analysis against St-Lys-Lys-Tyr-Leu-NH$_2$ (SEQ ID NO:6) as a marker (eluting using an acetonitrile gradient at fraction 25). Samples were monitored for radioactivity in a gamma counter.

Figure 15:
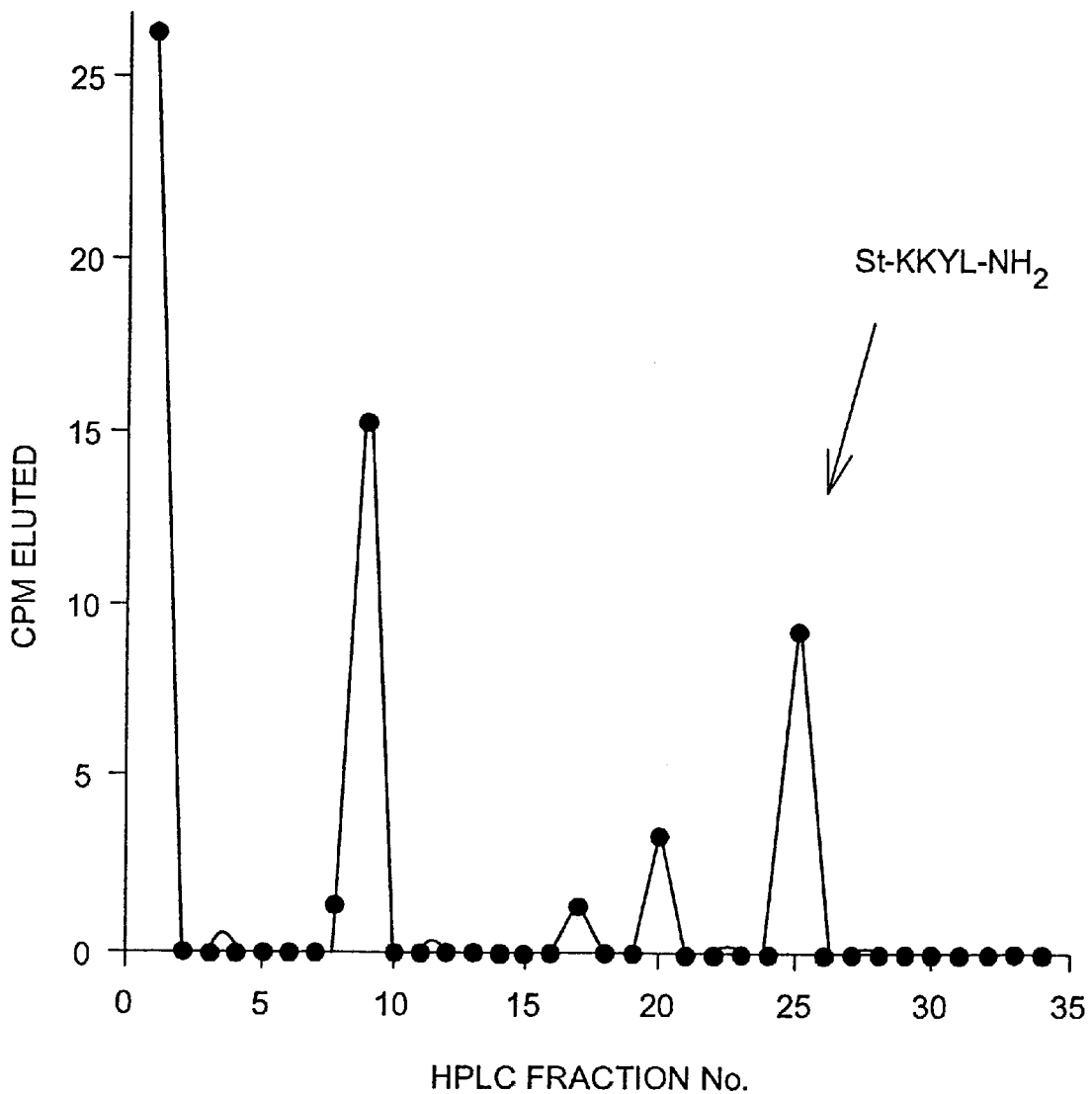
FIG. 15 shows the HPLC analysis of brain extracts of rats intranasally administered with $^{125}$I-St-Lys-Lys-Tyr-Leu-NH$_2$ (SEQ ID NO:6)

As can be seen in FIG. 15, intact St-Lys-Lys-Tyr-Leu-NH$_2$ (SEQ ID NO:6) could be observed in the brain thirty minutes after application, indicating that the conjugates of the invention, when administered intranasally are able to reach the brain.

D. The Impotence Prevention Aspect of the Invention
Biological Tests for Penile Reflexes The biological tests involved measurements of penile reflexes in castrated rats following transdermal application of the conjugates of the invention. In a first type of biological experiment the effects of compositions with various carriers on penile reflexes were measured and it was found that Sefsol™ was the most effective carrier.

(a) Methods
Animal Model for Impotence

Rats with reduced sexual potential due to castration were employed. Male rats (250–300 g, about three months old) were kept in a 12-hours light, 12-hours dark cycle. Experiments were always conducted within the dark period, 2–6 hours after the onset of darkness. Male rats were castrated and given partial testosterone replacement (4 µg/100 g body weight) in the form of daily injection during 14–21 consecutive days (the duration of the experiment). Experiments were conducted one week following surgery.

Direct Evaluation of Penile Reflexes (Erections)

A procedure was utilized that employed the technique that measures sexual reflexes in the penis, which enables direct evaluation of penile erection following transdermal administration of the drug. Successful reproduction depends, in large part, upon the precise execution of temporally organized, functionally related behavioral units. In these experiments, we concentrated on the final stages of the erection process (reddening of the penis accompanied by its distension and extension leading to complete erection) and monitored the latency time to the first E2 and first cup (Okumura, M., et al., Chem. Pharm. Bull. 37, 1375 (1989)).

For testing, each animal was restrained in a supine position with the anterior portion of its body enclosed in a loosely fitting cylinder (7 cm diam.). After a belt was secured around the torso, the glans penis was extruded from its sheath and gently held perpendicular to the abdomen by a thin wooden applicator positioned at the posterior of the penis. The legs of the male were held by the observer and this position was maintained throughout the test period. The duration of the session was 45 minutes. The latencies and numbers of E2 and cups were recorded and plotted.

An E2 is defined as a complete erection which can be followed by cup in which the penile tip is turned into a cup-like structure, whereby the glands flare out such that the penis is wider in its distal portion than its base. This final stage requires E2 and is probably a pre-requisite for ejaculation. Using all the parameters one can obtain a reliable measure of the sexual activity of the tested rat.

Duration of ES2 was determined by monitoring animals for a period of 45 minutes and calculating total time of erection whether by measuring the length of a single erection episode or by adding together several non-continuous erection episodes. The minimal duration of a single erection episode was calculated as half a minute.

EXAMPLE D1
Effect of the Conjugates of the Invention in a Rat Model of Impotence Conjugates were dissolved in dimethylsulfoxide (DMSO) at a concentration of $10^{-3}$M and 10 µl were utilized per application. Rats used were castrated-treated by partial testosterone replacement (Gozes et al., J. Clin. Inves., 90:810–814 (1992)). In short, male rats (90–100 days old) were castrated and immediately injected daily with 4 µg/100 g BW testosterone, s.c. for 21 consecutive days, the duration of the experiment. Experiments were initiated one week after surgery. Penile reflexes were measured as described above.

Figure 16:
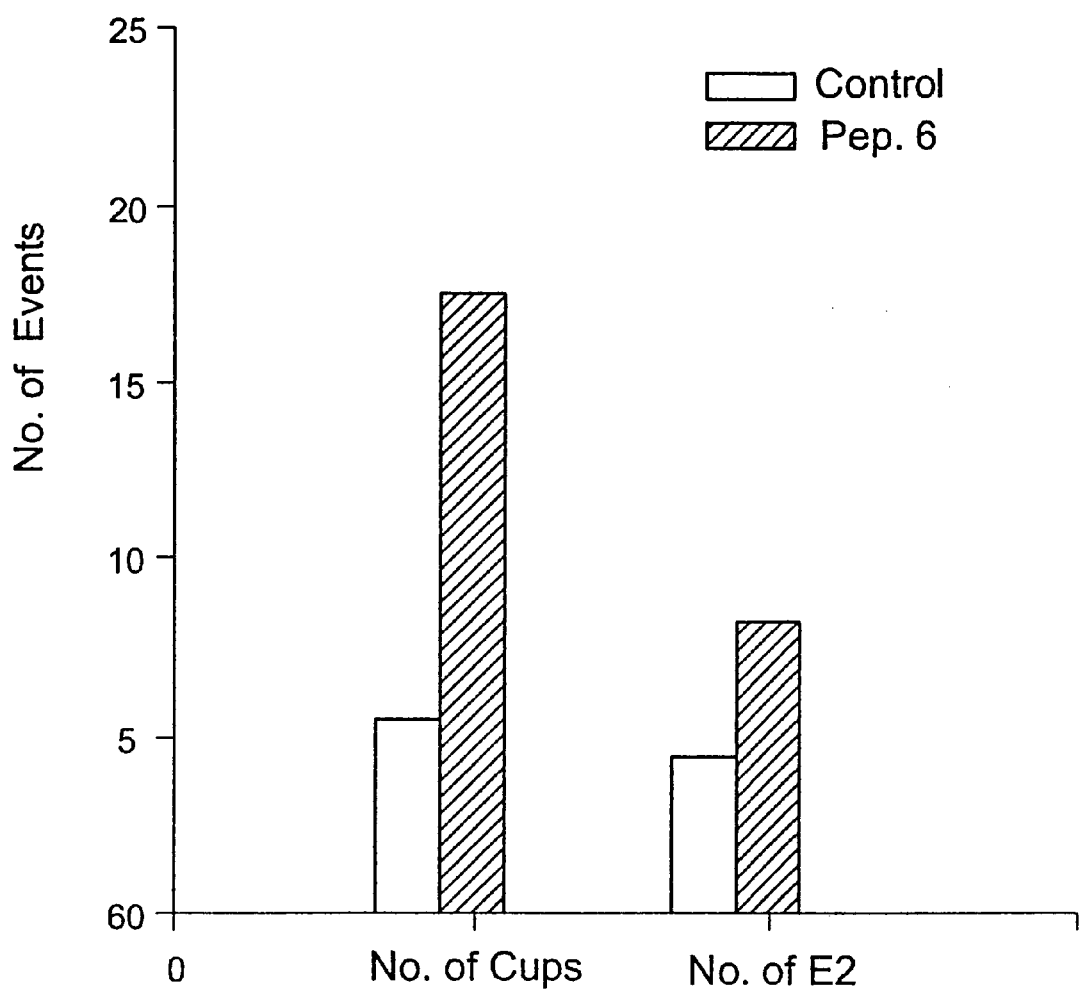
FIG. 16 shows the effect of St-Ala-Val-Lys- Lys-Tyr-Leu-Asn-Ser-Ile-Leu-Asn-NH$_2$ (SEQ ID NO:24) (peptide 6) in DMSO on the number of E2 and cups.
Figure 17:
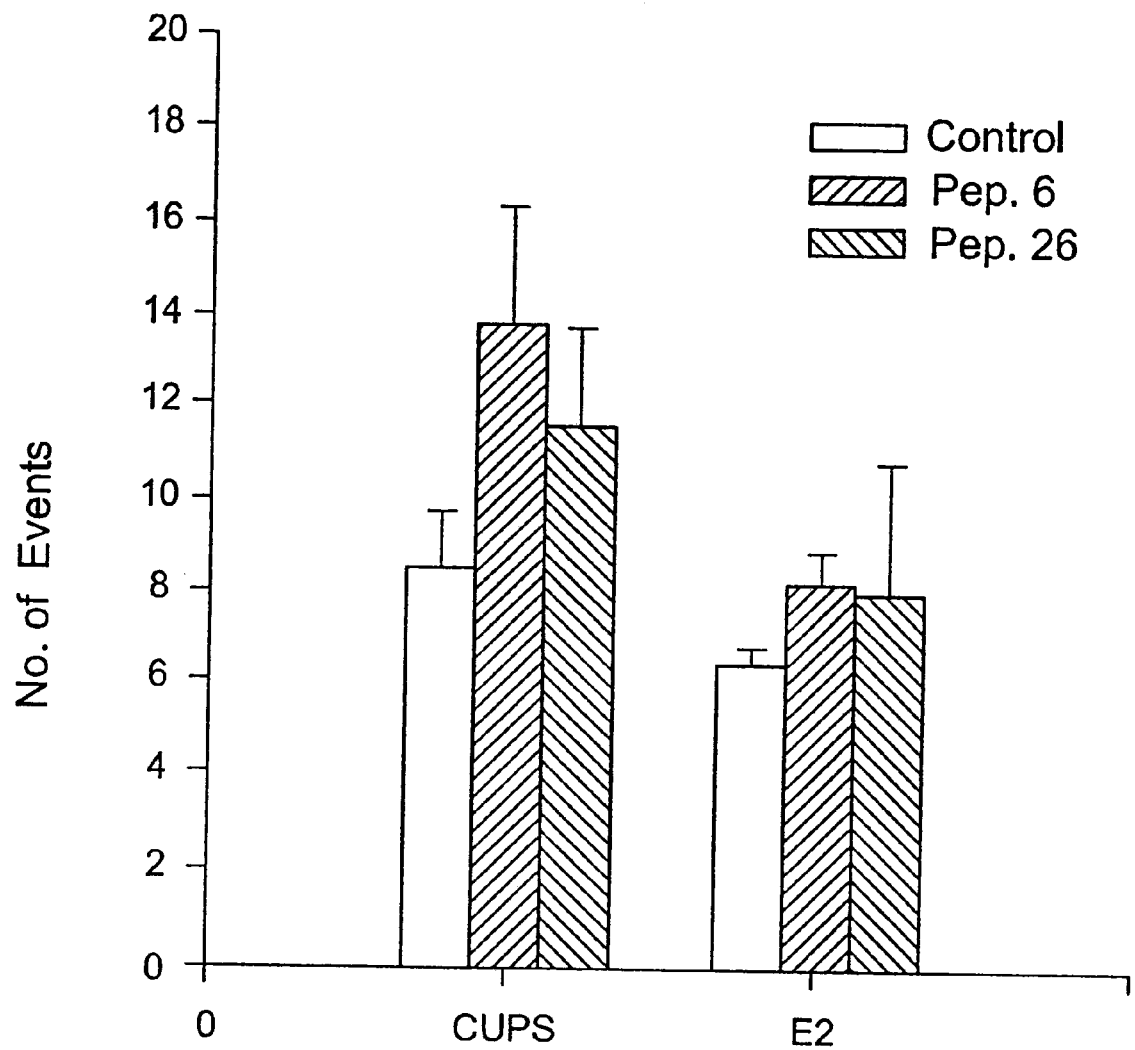
FIG. 17 shows the effect of St-Ala-Val-Lys-Lys-Tyr-Leu-Asn-Ser-Ile-Leu-Asn-NH$_2$ (SEQ ID NO:24) (peptide 6) and of St-Ala-Val-Lys-Lys-Tyr-Leu-NH$_2$ (SEQ ID NO:7) (peptide 26) in DMSO on the number of cups and on the number of E2.
Figure 18:
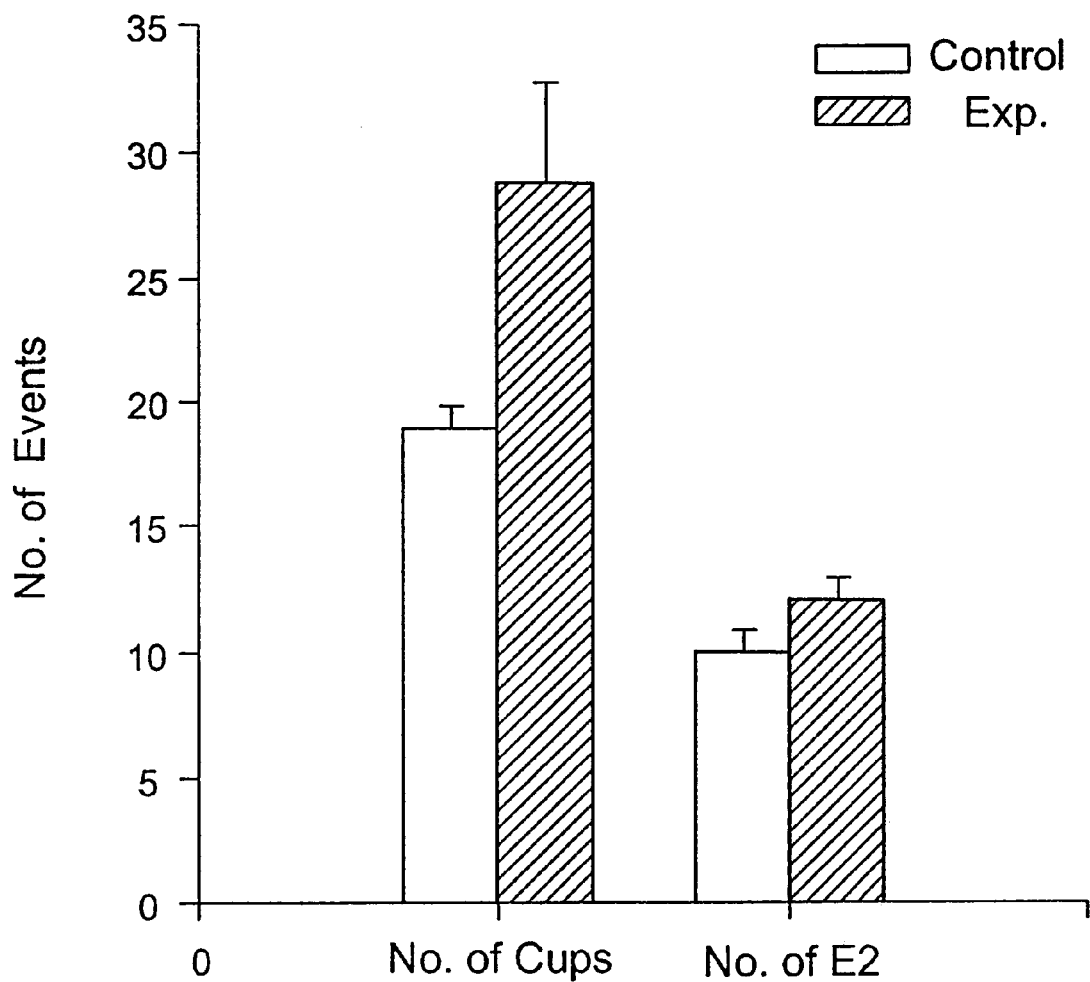
FIG. 18 shows the effect of St-Lys-Lys-Tyr-Leu-NH$_2$ (SEQ ID NO:6) in 5% Sefsol™/20% isopropanol on the number of cups and on the number of E2 (C=vehicle control; E=experimental peptide)
Figure 19:
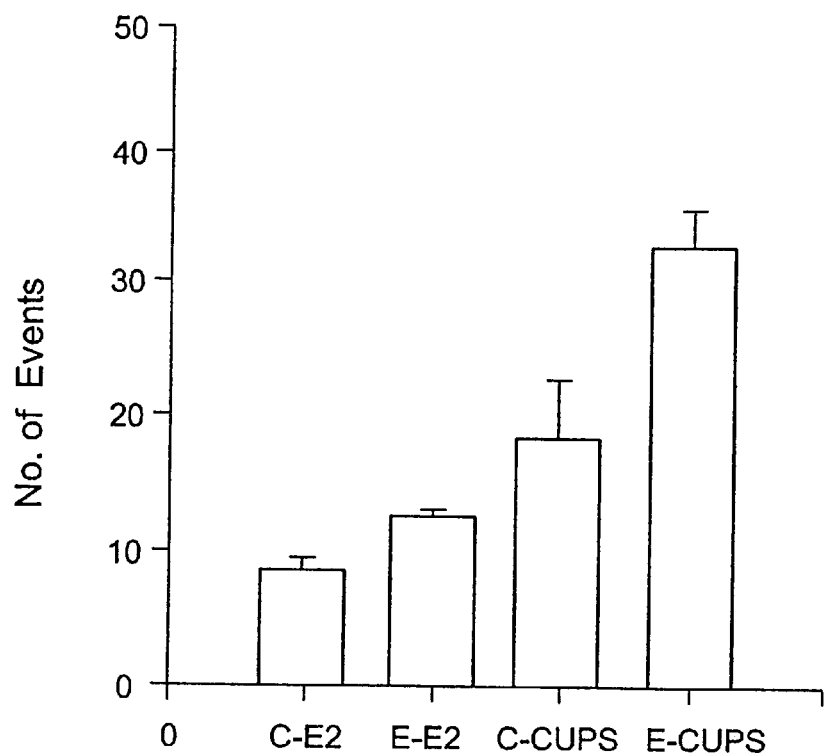
FIG. 19 shows the effect of St-Ser-Ile-Leu-Asn-NH$_2$ (SEQ ID NO:25) in Sefsol™/isopropanol on the number of cups and on the number of E2 (C=vehicle control; E=experimental peptide)
Figure 20:
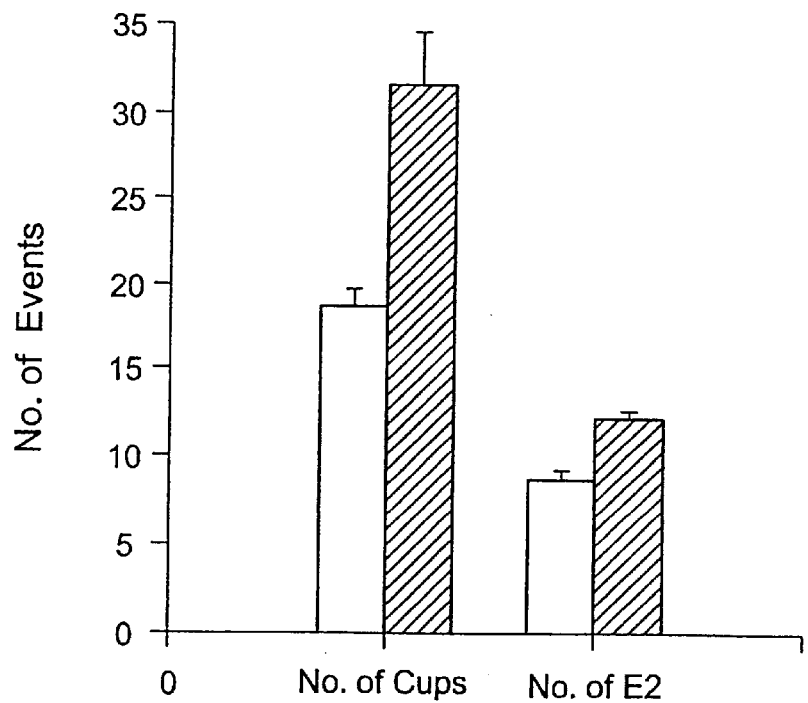
FIG. 20 shows the effect of St-Asn-Ser-Ile-Leu-Asn-NH$_2$ (SEQ ID NO:8) in Sefsol™/isopropanol on the number of cups and on the number of E2 (C=vehicle control; E=experimental peptide)
Figure 21:
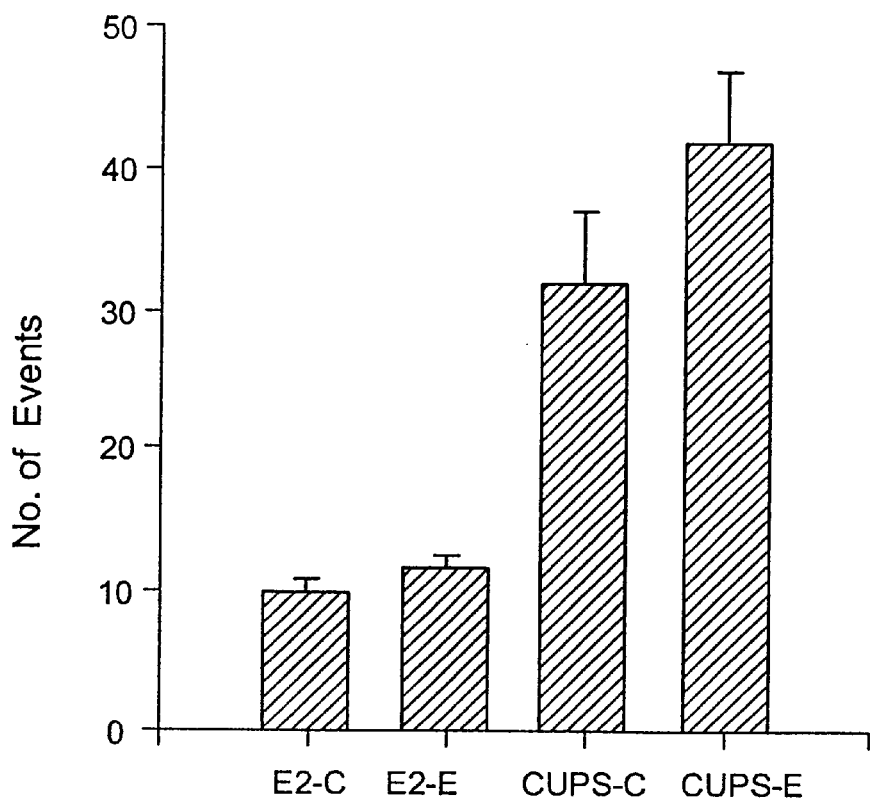
FIG. 21 shows the effect of St-Asn-Ser-Ile-Tyr-Asn-NH$_2$ (SEQ ID NO:22) in Sefsol™/isopropanol on the number of cups and on the number of E2 (C=vehicle control; E experimental peptide)
Figure 22:
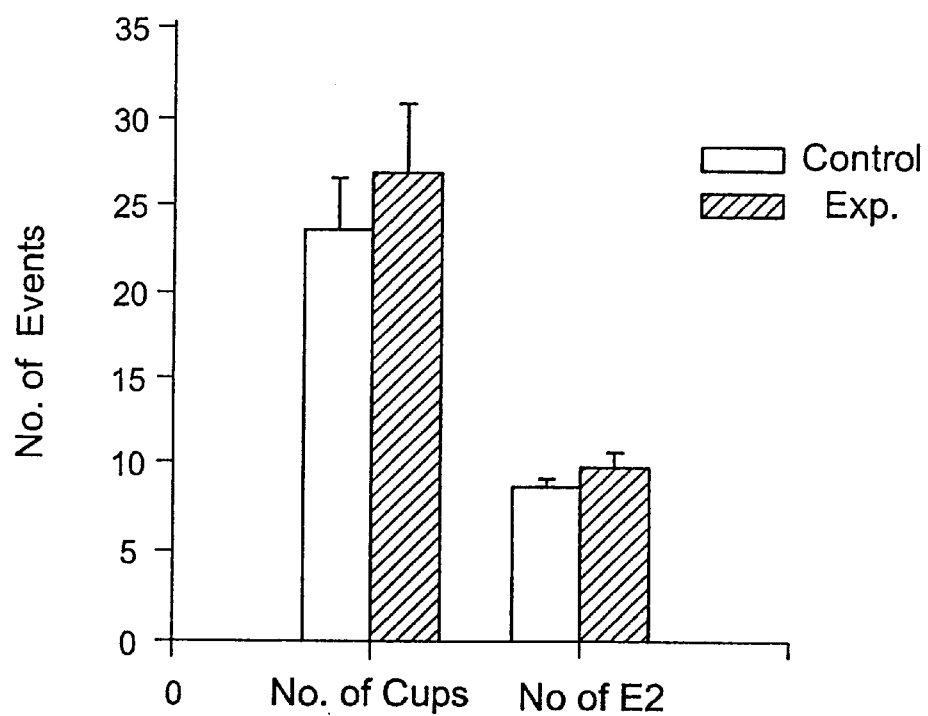
FIG. 22 shows the effect of St-Asn-Ser-Tyr-Leu-Asn-NH$_2$ (SEQ ID NO:11) in Sefsol™/isopropanol on the number of cups and on the number of E2.
Figure 23:
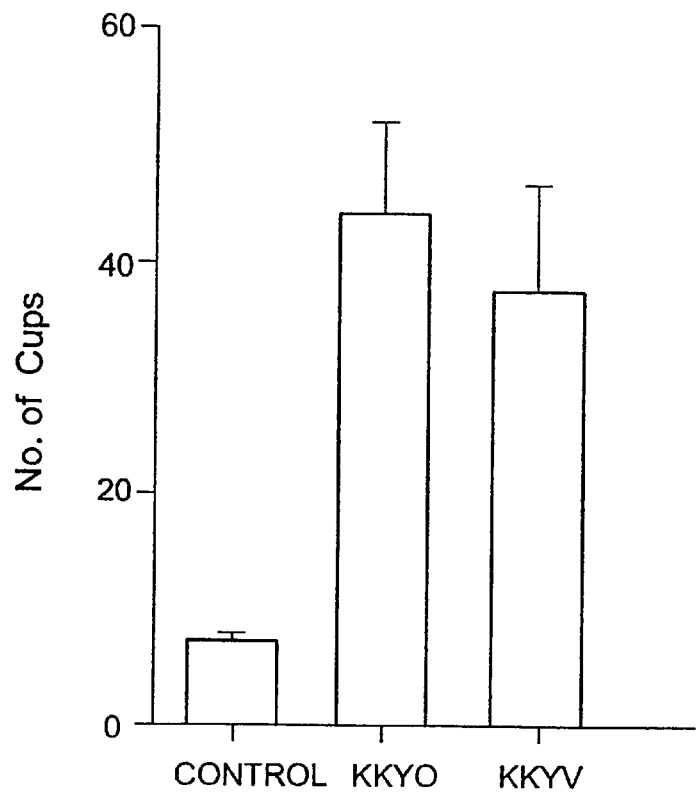
FIG. 23 shows the effect of St-Lys-Lys-Tyr-D-Ala-NH$_2$ (KKYO) and St-Lys-Lys-Tyr-Val-NH$_2$ (KKYV) (SEQ ID NO:9) on the number of cups.
Figure 24:
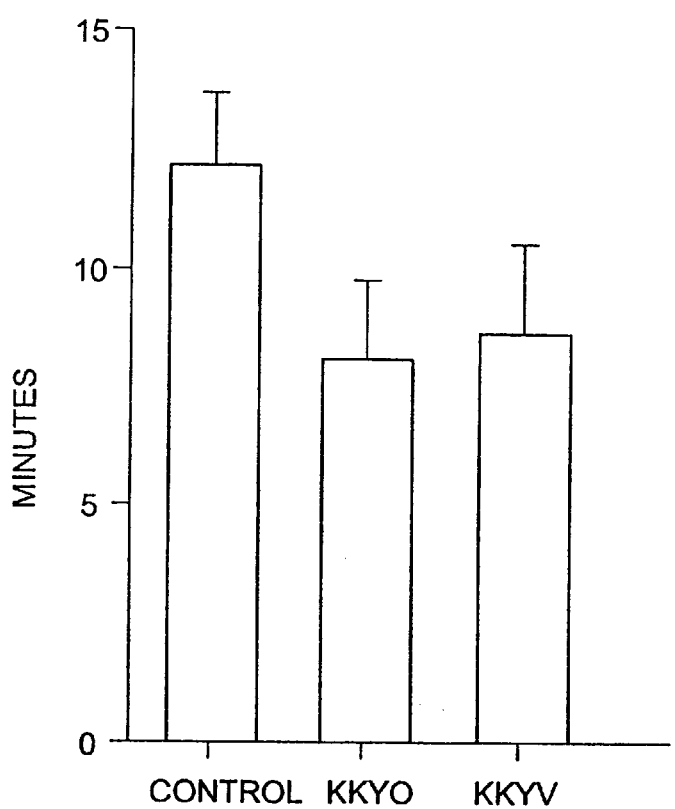
FIG. 24 shows the effect of St-Lys-Lys-Tyr-D-Ala-NH$_2$ (KKYO) and St-Lys-Lys-Tyr-Val-NH$_2$ (KKYV) (SEQ ID NO:9) on the latency to the first cup.
Figure 25:
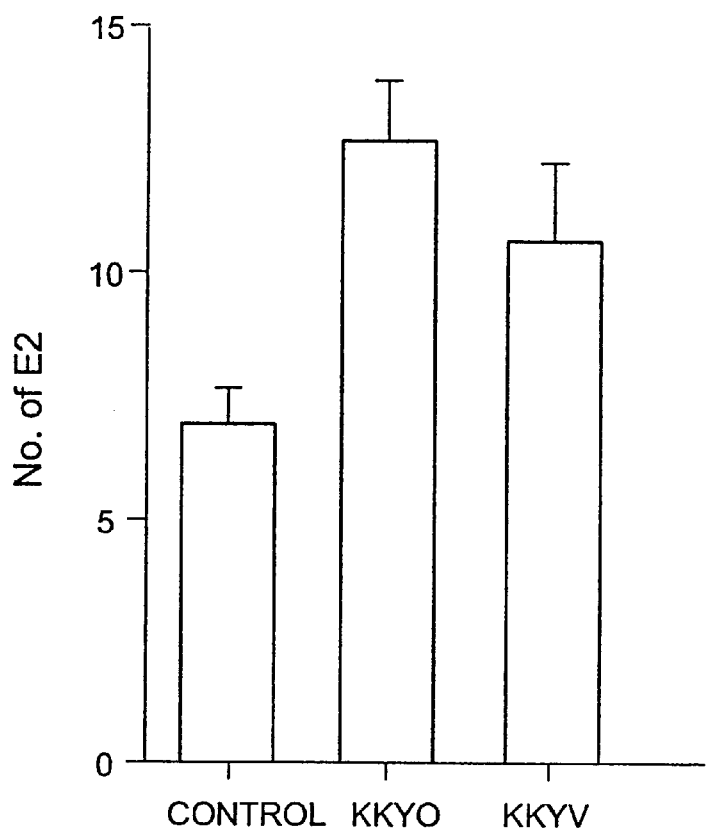
FIG. 25 shows the effect of St-Lys-Lys-Tyr-D-Ala-NH$_2$ (KKYO) and St-Lys-Lys-Tyr-Val-NH$_2$ (KKYV) (SEQ ID NO:9) on the number of E2.
Figure 26:
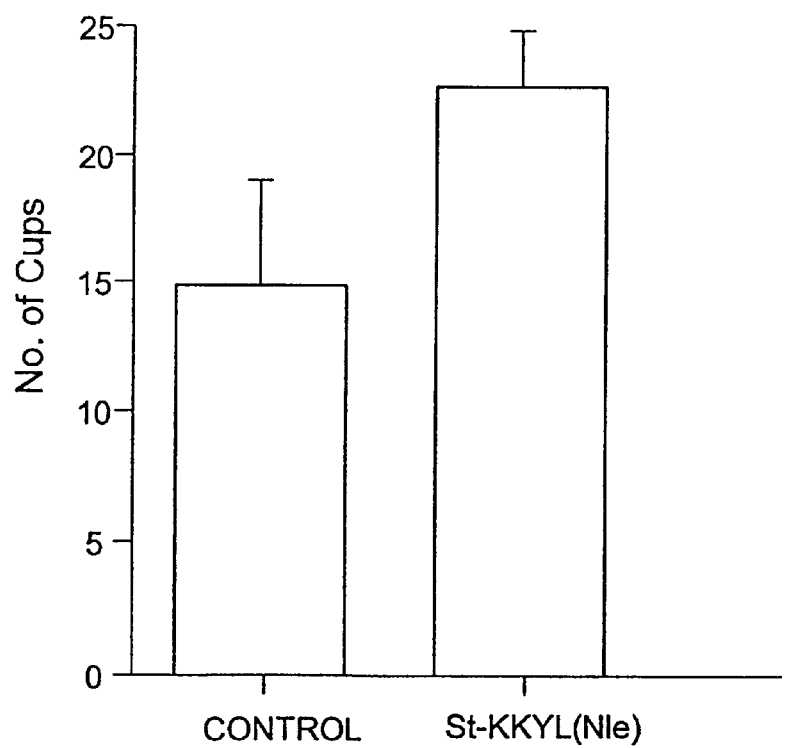
FIG. 26 shows the effect of St-Lys-Lys-Tyr-Leu-Nle-NH$_2$ (SEQ ID NO:10) on the number of cups.
Figure 27:
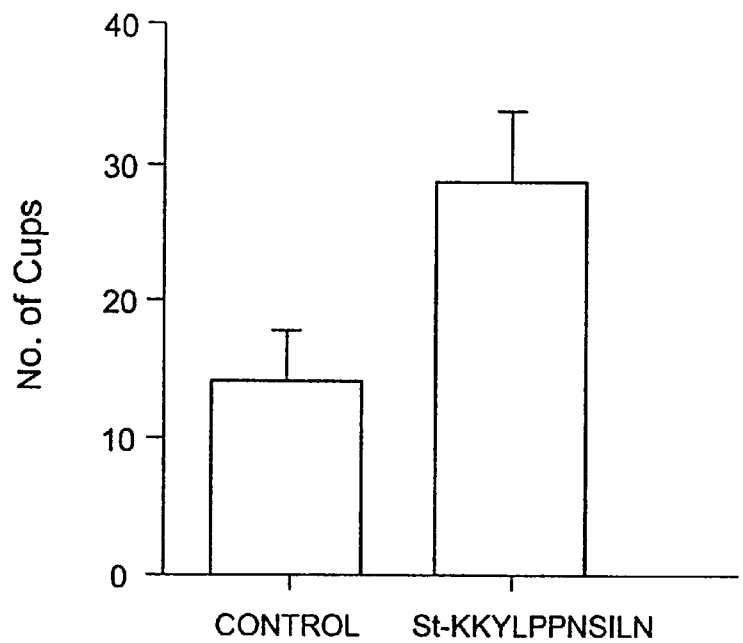
FIG. 27 shows the effect of St-Lys-Lys-Tyr-Leu-Pro-Pro-Asn-Ser-Ile-Leu-Asn-NH$_2$ (SEQ ID NO:13) on the number of cups.

FIG. 16 shows that peptide 6 (St-Ala-Val-Lys-Lys-Tyr-Leu-Asn-Ser-Ile-Leu-Asn-NH$_2$ (SEQ ID NO:24) was able to significantly improve both number of cups and the number of E2 as compared to control. FIG. 17 depicts peptide 6 in comparison to peptide 26. Experiments were repeated for the other conjugates of the invention substantially as described above, but peptides were dissolved in 5% Sefsol™ and 20% isopropanol to a final concentration of 7 µg/10 µl per animal. The conjugates tested were: St-Lys-Lys-Tyr-Leu-NH$_2$ (SEQ ID NO:6); St-Ser-Ile-Leu-Asn-NH$_2$ (SEQ ID NO:25); St-Asn-Ser-Ile-Tyr-Leu-Asn-NH$_2$ (SEQ ID NO:74); St-Lys-Lys-Tyr-D-Ala-NH$_2$; St-Lys-Lys-Tyr-Val-NH$_2$ (SEQ ID NO:9); St-Lys-Lys-Tyr-Leu-Nle-NH$_2$ (SEQ ID NO:10); St-Lys-Lys-Tyr-Leu-Pro-Pro-Asn-Ser-Ile-Leu-Asn-NH$_2$ (SEQ ID NO:73).

The results are shown in FIGS. 18–27 and indicate that all tested conjugates were able to improve all tested impotence parameters which were determined (No. of cups, No. of E2 and reduction of latency to the first cup) as compared to control.

EXAMPLE D2
Biodistribution Following Topical Administration of St-Lys-Lys-Tyr-Leu-NH$_2$ (SEQ ID NO:6)

St-Lys-Lys-Tyr-Leu-NH$_2$ (SEQ ID NO:6) was radioiodinated as before and about 2.2×10$^6$ cpm/2 µl 5% Sefsol™, 20% isopropanol/rat were applied topically on the sex organ of 250–300 g rats. Animals were sacrificed at indicated times and tissues were weighed and counted for radioactivity in a gamma counter.

Figure 28:
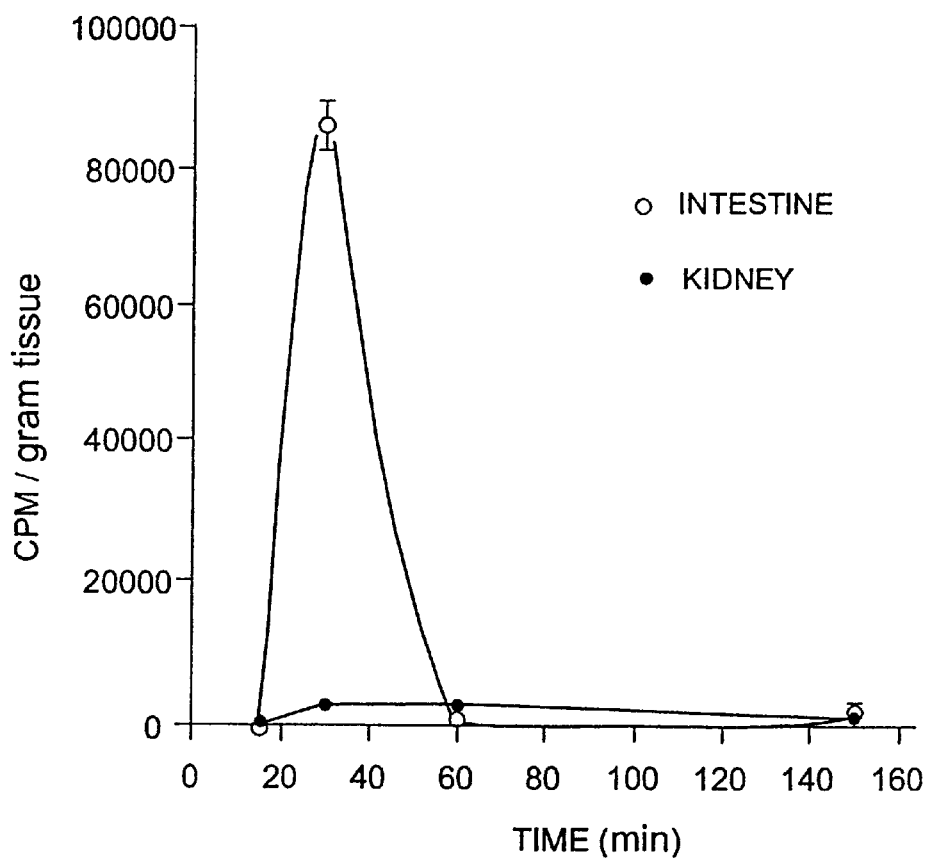
FIG. 28 shows biodistribution following topical administration of $^{125}$I-St-Lys-Lys-Tyr-Leu-NH$_2$ (SEQ ID NO:6)

The results are shown in FIG. 28. These results indicate that conjugates which were administered transdermally were able to penetrate the inner tissue of the animal.

EXAMPLE D3
HPLC Analysis of Intestinal Extract

Experiment was performed as indicated in Example D2. Animals were sacrificed 30 minutes following drug administration and the intestine was removed weighed and counted for radioactivity in a gamma counter. Radioactive tissue samples were thereafter homogenized and subjected to centrifugation (5,400 g for 25 min.). Supernatants were then subjected to HPLC analysis against radiolodinated St-Lys-Lys-Tyr-Leu-NH$_2$ (SEQ ID NO:6) as a marker (eluting using an acetonitrile gradient at fraction 25). Samples were monitored for radioactivity in a gamma counter.

Figure 29:
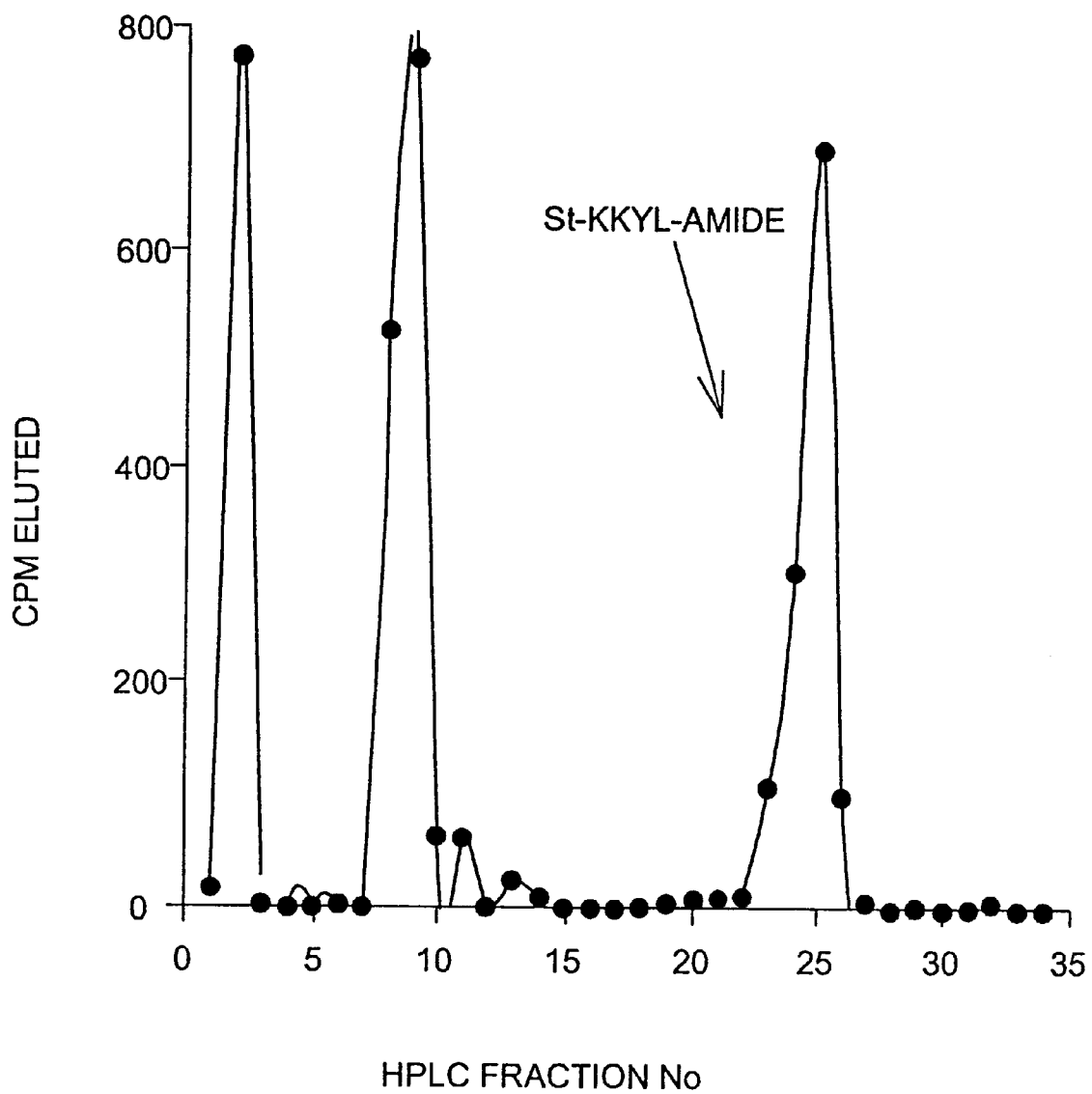
FIG. 29 shows the HPLC analysis of intestinal extract of animals topically administered with $^{125}$I-St-Lys-Lys-Tyr-Leu-NH$_2$ (St-KKYL-NH$_2$) (SEQ ID NO:6)

The results are shown in FIG. 29. As can be seen from the results in FIGS. 26 and 27 of the applied 2.2×10$^6$ cpm/g more than 80,000 cpm/g were located in the intestine 30 mins. following application. By comparison, using the same amounts of radiolabeled St-Nle$^{17}$-VIP only 3700 cpm/g were obtained in the intestine (Gozes et al., *Endocrinology*, 134:2121–2125 (1994)) showing that the short conjugate of the invention has a much better penetration than the full 28 amino acid conjugate.

EXAMPLE D4
Effect of the Conjugates of the Invention in a Rabbit Model of Impotence New Zealand white rabbits (from Yokneam, Israel) were anesthetized with Rompun and Ketavet. Additionally, pentobarbital 10 mg/kg, i.v. was administered into an ear vein. Anesthesia was maintained by bolus injections of pentobarbital (5–10 mg/kg). The animals were placed in a supine position on an operating table, in a temperature-regulated environment. The area around the penis was shaved and a 20 gauge needle was inserted into the left or right corpus cavernosum and the catheter connected to a pressure transducer for a continuous recording of the intracavarnosal (i.c.) pressure. The transducer amplifier used was Model PM-1000 (CWE incorporated); System 1000 power supply (CWE incorporated); Software: DI 200 PGH/PGL (DATA Q Instrument Inc.). When injection was required, a second catheter was placed into the other side of the corpus cavernosum for the administration of the drugs, both catheters were filled with blood. The catheter for blood pressure recording was flushed with 0.5 ml 2% heparin. Increases in the i.c. blood pressure are expressed on the graphs as mm Hg.

Figure 30:
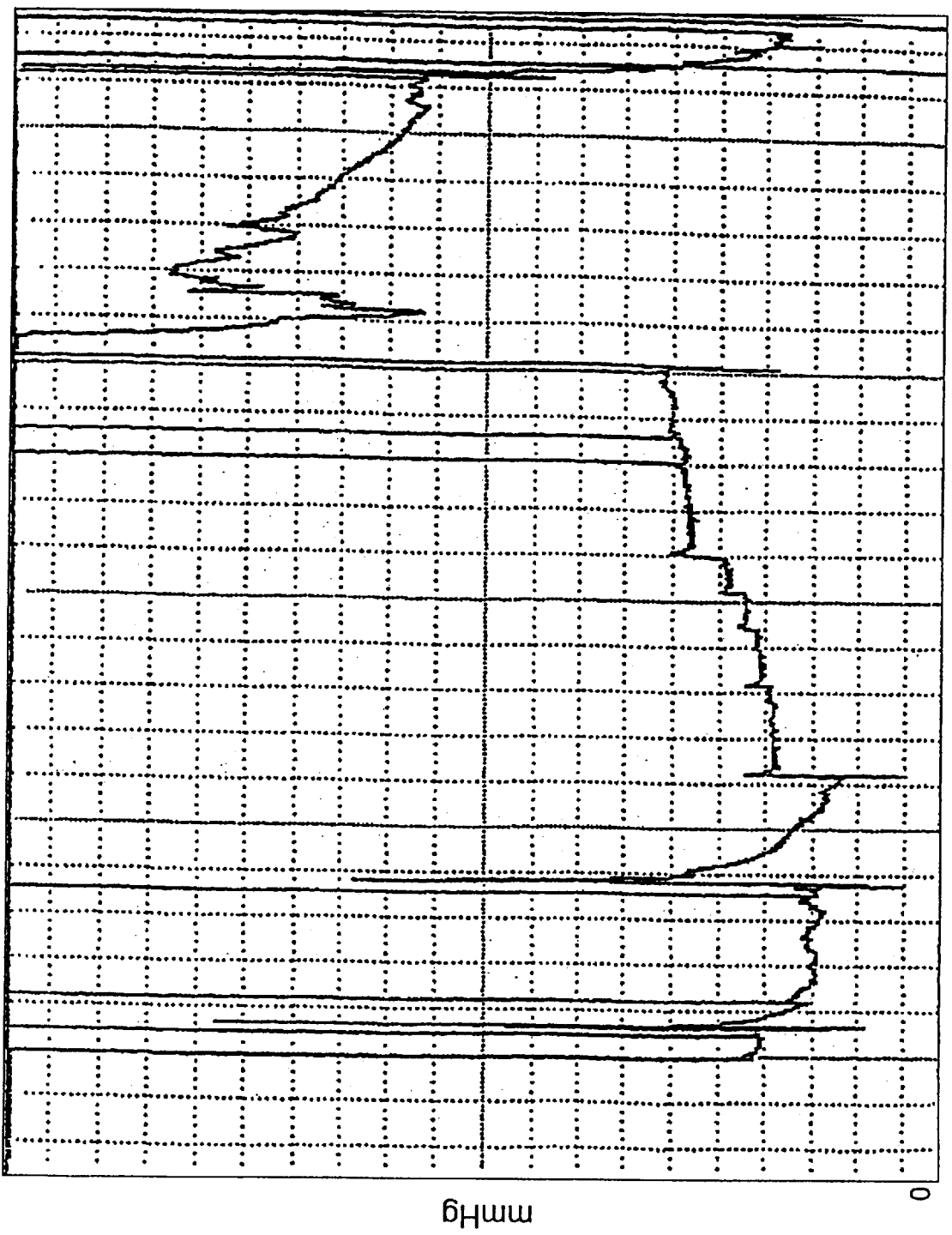
FIG. 30 shows the effect of injection into the corpus cavernosum to vehicle, 0.1 μg of St-Lys-Lys-Tyr-Leu-NH$_2$ (SEQ ID NO:6), and 10 μg St-Lys-Lys-Tyr-Leu-NH$_2$ (SEQ ID NO:6) on penile blood pressure.

FIG. 30 shows preliminary results of change of pressure obtained with injections of St-Lys-Lys-Tyr-Leu-$NH_2$ (SEQ ID NO:6), in the corpus cavernosum. Here 10 μg showed increased activity, with penile blood pressure increasing to 75 mmHg (from 15–20 mmHg) indicating that this conjugate can effect penile erection also by direct injection.

E. Pharmaceutical Compositions for Transdermal Applications

An example of ointment composition for transdermal application of lipophilic conjugated peptides in accordance with the present invention with Sefsol 318™ as a carrier comprises: 1 mg peptide per 714 μl 10% Sefsol 318™ (glyceryl monocaprylate) and 714 , μl 40% isopropanol (final concentrations: 5% Sefsol, 20% isopropanol and about 0.7 mg/ml peptide).

What is claimed is:

1. A conjugate of a peptide coupled to a lipophilic moiety, wherein the peptide has at least 3 and at most 12 amino acid residues, said conjugate being selected from the formulae:

(i) $R_1$-$X_1$-$X_1'$-$X_1''$-$X_2$-NH—$R_2$ (SEQ ID NO:2);

(ii) $R_1$-$X_3$-Ser-$X_4$-Leu-Asn-NH—$R_2$ (SEQ ID NO:3);

(iii) 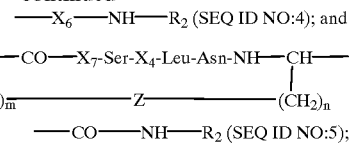 -Lys-Lys-Tyr-$X_5$— 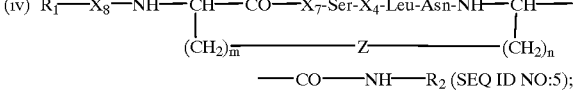 —$X_6$—NH—$R_2$ (SEQ ID NO:4); and (iv) $R_1$—$X_8$—NH—CH—CO—$X_7$-Ser-$X_4$-Leu-Asn-NH—CH—
         |                                            |
      (CH$_2$)$_{\overline{m}}$ ——————— Z ——————— (CH$_2$)$_n$
      —CO—NH—$R_2$ (SEQ ID NO:5);

wherein $R_1$ is H or a lipophilic moiety;

R$_2$ is H, a lipophilic moiety, a lipophilic moiety substituted by X$_3$-Ser-X$_4$-Leu-Asn-NHR$_1$ (SEQ ID NO:79) or a spacer consisting of 1–3 residues of a non-charged amino acid coupled to X$_1$-X$_1$'-X$_1$"-X$_2$-NHR$_1$ (SEQ ID NO:80), with the proviso that at least one of R$_1$ and R$_2$ is a lipophilic moiety;

X$_1$ is a covalent bond, Ala, Val, Ala-Val, Val-Ala, L-Lys, D-Lys, Ala-Lys, Val-Lys, Ala-Val-Lys; Val-Ala-Lys or Orn;

X$_1$' is L-Lys, D-Lys or Orn;

X$_1$" is L-Tyr, D-Tyr, Phe, Trp or the residue of p-amino phenylalanine;

X$_4$ is Ile or Tyr;

X$_5$ is a residue of a hydrophobic aliphatic amino acid;

X$_2$ is X$_5$, X$_5$-Asn, X$_5$-Ser, X$_5$-Ile, X$_5$-Tyr, X$_5$-Leu, X$_5$-Nle, X$_5$-D-Ala, X$_5$-Asn-Ser, X$_5$-Asn Ser-Ile (residues 1–4 of SEQ ID NO:75), X$_5$-Asn-Ser-Tyr (residues 1–4 of SEQ ID NO:76), X$_5$-Asn-Ser-Ile-Leu (residues 1–5 of SEQ ID NO:75), X$_5$-Asn-Ser-Tyr-Leu (residues 1–5 of SEQ ID NO:76), X$_5$-Asn-Ser-Tyr-Leu (residues 1–5 of SEQ ID NO:76), X$_5$-Asn-Ser-Ile-Leu-Asn (SEQ ID NO:75) or X$_5$-Asn-Ser-Tyr-Leu-Asn (SEQ ID NO:76);

X$_3$ is a covalent bond, Asn, X$_5$, X$_5$-Asn, Tyr-X$_5$, Tyr-X$_5$-Asn, Lys-X$_5$, Lys-X$_5$-Asn, Lys-Tyr-X$_5$, Lys-Tyr-X$_5$-Asn (residues 4–7 of SEQ ID NO:77), Lys-Lys-Tyr-X$_5$ (residues 3–6 of SEQ ID NO:77), Lys-Lys-Tyr-X$_5$-Asn (residues 3–7 of SEQ ID NO:77), Val-Lys-Lys-Tyr-X$_5$ (residues 2–6 of SEQ ID NO:78), Val-Ala-Lys-Lys-Tyr-X$_5$-Asn (SEQ ID NO:77), or Ala-Val-Lys-Lys-Tyr-X$_5$-Asn (SEQ ID NO:78);

X$_6$ is a covalent bond or Asn, Ser, Ile, Tyr, Leu, Asn-Ser, Asn-Ser-Ile, Asn-Ser-Tyr, Asn-Ser-Ile-Leu (residues 2–5 of SEQ ID NO:75), Asn-Ser-Tyr-Leu (residues 2–5 of SEQ ID NO:76), Asn-Ser-Ile-Leu-Asn (residues 2–6 of SEQ ID NO:75) or Asn-Ser-Tyr-Leu-Asn (residues 2–6 of SEQ ID NO:76);

X$_7$ is a covalent bond or Asn;

X$_8$ is a covalent bond, X$_5$, Tyr, Lys, Tyr-X$_5$, Lys-X$_5$, Lys-Tyr-X$_5$, Lys-Lys-Tyr-X$_5$ (residues 3–6 of SEQ ID NO:77), Val-Lys-Lys-Tyr-X$_5$ (residues 2–6 of SEQ ID NO:78), Ala-Lys-Lys-Tyr-X$_5$ (residues 2–6 of SEQ ID NO:77), or Ala-Val-Lys-Lys-Tyr-X$_5$ (residues 1–6 of SEQ ID NO:78);

Z is —CONH—, NHCO—, —S—S—, —S(CH$_2$)$_t$CO—NH— or —NH—CO(CH$_2$)$_t$S—;

m is 1 or 2 when Z is —CONH—, —S—S— or —S(CH$_2$)$_t$CO—NH—, or m is 2, 3 or 4 when Z is —NH—CO— or —NH—CO(CH$_2$)$_t$S—;

n is 1 or 2 when Z is —NH—CO—, —S—S— or —NH—CO(CH$_2$)$_t$S—, or n is 2, 3 or 4 when Z is —CONH— or —S(CH$_2$)$_t$CO—NH—, and t is 1 or 2, with the proviso that the conjugate stearoyl-Ala-Val-Lys-Lys-Tyr-Leu-Asn-Ser-Ile-Leu-Asn-NH$_2$ (SEQ ID NO:24) is excluded.

2. A conjugate according to claim 1, wherein X$_5$ is a residue of an D- or L-amino acid selected from Ala, Ile, Leu, Met, Val, Nva and Nle.

3. A conjugate according to claim 1, wherein the lipophilic moiety R$_1$ is a saturated or unsaturated hydrocarbyl or carboxylic acyl radical having at least 5 carbon atoms.

4. A conjugate according to claim 3, wherein R$_1$ is selected from: stearoyl (ST), caproyl (Cap) and lauroyl (Lau).

5. A conjugat according to claim 4, selected from the group consisting of:
St-Lys-Lys-Tyr-Leu-NH$_2$ (SEQ ID NO:6);
St-Lys-Lys-Tyr-D-Ala-NH$_2$;
St-Ala-Val-Lys-Lyl-Tyr-Leu-NH$_2$ (SEQ ID NO:7);
St-Asn-Ser-Ile-Leu-Asn-NH$_2$ (SEQ ID NO:8);
St-Lys-Lys-Tyr-Leu-Nle-NH$_2$ (SEQ ID NO:10);
St-Lys-Lys-Tyr-Val-NH$_2$ (SEQ ID NO:9); and
St-Ser-Ile-Leu-Asn-NH$_2$ (SEQ ID NO:25).

6. A conjugate according to claim 4, selected from the group consisting of:
St-Asn-Ser-Tyr-Leu-Asn-NH$_2$ (SEQ ID NO:11);
St-Asn-Ser-Ile-Tyr-Asn-NH$_2$ (SEQ ID NO:12); and
St-Lys-Lys-Tyr-Leu-Pro-Pro-Asn-Ser-Ile-Leu-Asn-NH$_2$ (SEQ ID NO:13).

7. A conjugat according to claim 4, selected from the group consisting of:
Lau-Lys-Lys-Tyr-Leu-NH$_2$ (SEQ ID NO:14);
Cap-Lys-Lys-Tyr-Leu-NH$_2$ (SEQ ID NO:15);
St-Lys-Tyr-Leu-NH$_2$;
St-Lys-Lys-Tyr-Nle-NH$_2$ (SEQ ID NO:16);
St-Val-Lys-Lys-Tyr-Leu-NH$_2$ (SEQ ID NO:17);
St-Leu-Asn-Ser-Ile-Leu-Asn-NH$_2$ (SEQ ID NO:18);
St-Tyr-Leu-Asn-Ser-Ile-Leu-Asn-NH$_2$ (SEQ ID NO:19);
St-Lys-Lys-Tyr-Leu-Asn-NH$_2$ (SEQ ID NO:20);
St-Lys-Lys-Tyr-Leu-Asn-Ser-NH$_2$ (SEQ ID NO:21);
St-Lys-Lys-Tyr-Leu-Asn-Ser-Ile-NH$_2$ (SEQ ID NO:22); and
St-Lys-Lys-Tyr-Leu-Asn-Ser-Ile-Leu-NH$_2$ (SEQ ID NO:23).

8. A pharmaceutical composition comprising as an active ingredient a conjugate according to claim 1, together with a pharmaceutically acceptable carrier.

9. A pharmaceutical composition for the treatment of neurodegenerative diseases comprising as an active ingredient a conjugate selected from the group consisting of a conjugate according to claims 5 or 7.

10. A pharmaceutical composition according to claim 9, wherein the neurodegenerative disease is selected form the group consisting of: Alzheimer's disease, Down Syndrome, decline in motor or cognitive function due to ischemia, stroke, hereditary disease of the central and peripheral nervous system, decline in motor or cognitive function due to injury of the central or peripheral nervous system and neuronal disorder associated with blood circulation and neuronal survival.

11. A pharmaceutical composition according to claim 9, suitable for nasal administration.

12. A pharmaceutical composition according to claim 11, in the form of a nasal spray.

13. A pharmaceutical composition for the treatment of sexual disfunctions, comprising as an active ingredient a conjugate selected from thy group consisting of a conjugate according to claim 6, St-Lys-Lys-Tyr-D-Ala-NH$_2$, St-Lys-Lys-Tyr-Leu-Nle-NH$_2$ (SEQ ID NO: 10), and St-Lys-Lys-Tyr-Val-NH$_2$ (SEQ ID NO:9) together with a pharmaceutically acceptable carrier.

14. A pharmaceutical composition according to claim 10, for the treatment of male impotence.

15. A pharmaceutical composition according to claim 13, adapted for transdermal application.

16. A pharmaceutical composition according to claim 15, wherein the pharmaceutically acceptable carrier is 1-glyceryl monocaprylate.

17. A method for treating sexual disfunction, comprising administering a conjugate selected from the group consisting of a conjugate according to claim 5, a conjugate according to claim 6, and conjugate St-Ala-Val-Lys-Lys-Tyr-Leu-Asn-Ser-Ile-Leu-Asn-NH$_2$ (SEQ ID NO:24) to a patient in need thereof.

18. The method of claim 17, wherein the sexual disfunction is male impotence.

19. The method of claim 17, wherein the conjugate is formulated for transdermal administration.

20. The method of claim 17, wherein the conjugate is St-Ala-Val-Lys-Lys-Tyr-Leu-Asn-Ser-Ile-Leu-Asn-NH$_2$ (SEQ ID NO:24) and is combined with 1-glyceryl monocaprylate as a carrier.

21. A method for treating a neurodegenerative disease, comprising administering a conjugate selected from the group consisting of a conjugate according to claim 6, St-Lys-Lys-Tyr-D-Ala-NH$_2$, St-Lys-Lys-Tyr-Leu-Nle-NH$_2$ (SEQ ID NO:10), and St-Lys-Lys-Tyr-Val-NH$_2$ (SEQ ID NO:11) to a patient in need thereof.

22. The method of claim 21, wherein the neurodegenerative disease is selected from the group consisting of Alzheimer's disease, Down Syndrome, decline in motor or cognitive function due to ischemia, stroke, hereditary disease of the central and peripheral nervous system, decline in motor or cognitive function due to injury of the central or peripheral nervous system, and neuronal disorder associated with blood circulation and neuronal survival.

23. The method of claim 21, wherein the conjugate is administered nasally.

24. The method of claim 21, wherein the conjugate is formulated for administration in the form of a nasal spray.

* * * * *

SEQUENCE LISTING

```
<160> NUMBER OF SEQ ID NOS: 80

<210> SEQ ID NO: 1
<211> LENGTH: 28
<212> TYPE: PRT
<213> ORGANISM: HOMO SAPIENS

<400> SEQUENCE: 1

His Ser Asp Ala Val Phe Tyr Asp Asn Tyr Thr Arg Leu Arg Lys Gln
  1               5                  10                  15

Met Ala Val Lys Lys Tyr Leu Asn Ser Ile Leu Asn
             20                  25

<210> SEQ ID NO: 2
<211> LENGTH: 25
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: Any one or all of residues 1, 2 and 3 may be
      present or absent; residue 1 is Ala, Val, or
      absent; residue 2 is Ala, Val, or absent; residue
      3 is Ala, Val, Lys, D-Lys, Orn or absent; one of
      residues 1, 2, 3 or 4 is the N-terminal residue,
      and may be modified with a lipophilic moiety;
      residue 4 is Lys, D-Lys, or Orn;
      residue 5 is Tyr, D-Tyr, Phe, Trp, or p-amino Phe;
      residue 6 is a hydrophobic amino acid residue;
      any one or all of residues 7-11 may be present or
      absent; residue 7 is Asn, Ser, Ile, Tyr, Leu, Nle,
      D-Ala, or absent; residue 8 is Ser or absent;
      residue 9 is Ile, Tyr, or absent; residue 10 is Leu
      or absent; residue 11 is Asn or absent;
      any one or all of residues 12-25 may be present or
      absent;
      residue 12 is a Ser, Asn, a hdrophobic aliphatic
      amino acid residue, Tyr, Lys, Val, Ala, a non-charged
      amino acid residue, or absent;
      residue 13 is Ile, Tyr, Asn, a hydrophobic aliphatic
      amino acid residue, Lys, D-Lys, Orn, Ala, Val, a non-
      charged amino acid residue, or absent;
      residue 14 is Leu, Asn, a hydrophobic aliphatic amino
      acid residue, Tyr, Lys, a non-charged amino acid residue,
      Ala, Val, D-Lys, Orn, D-Tyr, Phe, Trp, p-amino Phe, or
```

-continued

```
        absent;
        residue 15 is Asn, a hydrophobic aliphatic amino acid
        residue, Tyr, Lys, D-Lys, Orn, D-Tyr, Phe, Trp, p-amino
        Phe, Ala, Val, or absent;
        residue 16 is Asn, a hydrophobic aliphatic amino acid
        residue, Tyr, Lys, Val, Ala, D-Tyr, Phe, Trp, p-amino
        Phe, Nle, Leu, Ile, Ser, D-Ala, D-Lys, Orn, or absent;
        residue 17 is a hydrophobic aliphatic amino acid residue,
        Lys, D-Lys, Orn, Asn, Ser, Ile, Leu, Tyr, Nle, D-Ala,
        D-Tyr, Phe, Trp, p-amino Phe, or absent;
        residue 18 is Asn, Lys, D-Lys, Orn, Tyr, D-Tyr, Phe, Trp,
        p-amino Phe, Ser, Ile, Leu, Nle, D-Ala, a hydrophobic
        aliphatic amino acid residue, or absent;
        residue 19 is Ser, Tyr, D-Tyr, Phe, Trp, p-amino Phe, a
        hydrophobic aliphatic amino acid residue, Ile, Leu, Asn,
        Nle, D-Ala, or absent;
        residue 20 is Ile, Tyr, Ser, Asn, Leu, a hydrophobic
        aliphatic amino acid residue, Nle, D-Ala, or absent;
        residue 21 is Leu, Ile, Tyr, Asn, Ser, Nle, D-Ala, or
        absent;
        residue 22 is Asn, Ile, Tyr, Ser, Leu, or absent;
        residue 23 is Asn, Leu, Ile, Tyr, or absent;
        residue 24 is Asn, Leu, or absent;
        residue 25 is Asn or absent;
        the C-terminal residue is amidated or modified with a
        lipophilic moiety.

<400> SEQUENCE: 2

Xaa Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Xaa Xaa Xaa Xaa
            20                  25

<210> SEQ ID NO: 3
<211> LENGTH: 25
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: Any one or all of residues 1-7 may be present
        or absent;
        residue 1 is Val, Ala, or absent;
        residue 2 is Val, Ala, or absent;
        residue 3 is Lys, Val, or absent;
        residue 4 is Lys or absent;
        residue 5 is Tyr, Lys, or absent;
        residue 6 is a hydrophobic aliphatic amino acid residue,
        Tyr, Lys, or absent;
        residue 7 is Asn, a hydrophobic aliphatic amino acid
        residue, or absent;
        residue 9 is Ile or Tyr;
        any one or all of residues 12-25 may be present or
        absent;
        residue 12 is a Ser, Asn, a hdrophobic aliphatic
        amino acid residue, Tyr, Lys, Val, Ala, a non-charged
        amino acid residue, or absent;
        residue 13 is Ile, Tyr, Asn, a hydrophobic aliphatic
        amino acid residue, Lys, D-Lys, Orn, Ala, Val, a non-
        charged amino acid residue, or absent;
        residue 14 is Leu, Asn, a hydrophobic aliphatic amino
        acid residue, Tyr, Lys, a non-charged amino acid residue,
        Ala, Val, D-Lys, Orn, D-Tyr, Phe, Trp, p-amino Phe, or
        absent;
        residue 15 is Asn, a hydrophobic aliphatic amino acid
        residue, Tyr, Lys, D-Lys, Orn, D-Tyr, Phe, Trp, p-amino
        Phe, Ala, Val, or absent;
        residue 16 is Asn, a hydrophobic aliphatic amino acid
        residue, Tyr, Lys, Val, Ala, D-Tyr, Phe, Trp, p-amino
        Phe, Nle, Leu, Ile, Ser, D-Ala, D-Lys, Orn, or absent;
        residue 17 is a hydrophobic aliphatic amino acid residue,
        Lys, D-Lys, Orn, Asn, Ser, Ile, Leu, Tyr, Nle, D-Ala,
        D-Tyr, Phe, Trp, p-amino Phe, or absent;
        residue 18 is Asn, Lys, D-Lys, Orn, Tyr, D-Tyr, Phe, Trp,
        p-amino Phe, Ser, Ile, Leu, Nle, D-Ala, a hydrophobic
        aliphatic amino acid residue, or absent;
``` residue 19 is Ser, Tyr, D-Tyr, Phe, Trp, p-amino Phe, a
hydrophobic aliphatic amino acid residue, Ile, Leu, Asn,
Nle, D-Ala, or absent;
residue 20 is Ile, Tyr, Ser, Asn, Leu, a hydrophobic
aliphatic amino acid residue, Nle, D-Ala, or absent;
residue 21 is Leu, Ile, Tyr, Asn, Ser, Nle, D-Ala, or
absent;
residue 22 is Asn, Ile, Tyr, Ser, Leu, or absent;
residue 23 is Asn, Leu, Ile, Tyr, or absent;
residue 24 is Asn, Leu, or absent;
residue 25 is Asn or absent;
the C-terminal residue is amidated or modified with a
lipophilic moiety.

<400> SEQUENCE: 3

Xaa Xaa Xaa Xaa Xaa Xaa Xaa Ser Xaa Leu Asn Xaa Xaa Xaa Xaa Xaa
 1               5                  10                  15

Xaa Xaa Xaa Xaa Xaa Xaa Xaa Xaa Xaa
            20                  25

<210> SEQ ID NO: 4
<211> LENGTH: 25
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: Residue 1 is Asp, Glu, Cys, Orn, Lys, or an
amino acid with a side chain of -(CH2)2NH3, and residue 1
may be modified with a lipophilic moiety;
residues 1 and 6 are linked by a -CO-NH-, -NH-CO-,
-S-S-, -S(CH2)tCO-NH-, or -NH-CO(CH2)tS- bond;
residue 5 is a hydrophobic aliphatic amino acid
residue;
residue 6 is Asp, Glu, Cys, Orn, Lys, or an amino acid
with a side chain of -(CH2)2NH3;
any one or all of residues 7-11 may be present or absent;
residue 7 is Asn, Ser, Ile, Tyr, Leu, or absent;
residue 8 is Ser or absent;
residue 9 is Ile, Tyr, or absent;
residue 10 is Leu or absent;
residue 11 is Asn or absent;
any one or all of residues 12-25 may be present or
absent;
residue 12 is a Ser, Asn, a hdrophobic aliphatic
amino acid residue, Tyr, Lys, Val, Ala, a non-charged
amino acid residue, or absent;
residue 13 is Ile, Tyr, Asn, a hydrophobic aliphatic
amino acid residue, Lys, D-Lys, Orn, Ala, Val, a non-
charged amino acid residue, or absent;
residue 14 is Leu, Asn, a hydrophobic aliphatic amino
acid residue, Tyr, Lys, a non-charged amino acid residue,
Ala, Val, D-Lys, Orn, D-Tyr, Phe, Trp, p-amino Phe, or
absent;
residue 15 is Asn, a hydrophobic aliphatic amino acid
residue, Tyr, Lys, D-Lys, Orn, D-Tyr, Phe, Trp, p-amino
Phe, Ala, Val, or absent;
residue 16 is Asn, a hydrophobic aliphatic amino acid
residue, Tyr, Lys, Val, Ala, D-Tyr, Phe, Trp, p-amino
Phe, Nle, Leu, Ile, Ser, D-Ala, D-Lys, Orn, or absent;
residue 17 is a hydrophobic aliphatic amino acid residue,
Lys, D-Lys, Orn, Asn, Ser, Ile, Leu, Tyr, Nle, D-Ala,
D-Tyr, Phe, Trp, p-amino Phe, or absent;
residue 18 is Asn, Lys, D-Lys, Orn, Tyr, D-Tyr, Phe, Trp,
p-amino Phe, Ser, Ile, Leu, Nle, D-Ala, a hydrophobic
aliphatic amino acid residue, or absent;
residue 19 is Ser, Tyr, D-Tyr, Phe, Trp, p-amino Phe, a
hydrophobic aliphatic amino acid residue, Ile, Leu, Asn,
Nle, D-Ala, or absent;
residue 20 is Ile, Tyr, Ser, Asn, Leu, a hydrophobic
aliphatic amino acid residue, Nle, D-Ala, or absent;
residue 21 is Leu, Ile, Tyr, Asn, Ser, Nle, D-Ala, or
absent;
residue 22 is Asn, Ile, Tyr, Ser, Leu, or absent;
residue 23 is Asn, Leu, Ile, Tyr, or absent;
residue 24 is Asn, Leu, or absent;

```
      residue 25 is Asn or absent;
      the C-terminal residue is amidated or modified with a
      lipophilic moiety.

<400> SEQUENCE: 4

Xaa Lys Lys Tyr Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa
                20                  25

<210> SEQ ID NO: 5
<211> LENGTH: 25
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: Any one or all of residues 1-6 may be present
      or absent; one of residues 1-6 is the N-terminal residue
      and may be modified with a lipophilic moiety;
      residue 1 is Ala or absent;
      residue 2 is Val, Ala, or absent;
      residue 3 is Lys or absent;
      residue 4 is Lys or absent;
      residue 5 is Tyr, Lys, or absent;
      residue 6 is a hydrophobic aliphatic amino acid residue,
      Tyr, Lys, or absent;
      residue 7 is Asp, Glu, Cys, Orn, Lys, or an amino acid
      with a side chain of -(CH2)2NH3; residues 7 and 13 are
      linked by a -CO-NH-, -NH-CO-, -S-S-, -S(CH2)tCO-NH-,
      or -NH-CO(CH2)tS- bond;
      residue 8 is Asn or absent;
      residue 10 is Ile or Tyr;
      residue 13 is Asp, Glu, Cys, Orn, Lys, or an amino acid
      with a side chain of -(CH2)2NH3;
      any one or all of residues 14-27 may be present or
      absent;
      residue 14 is a Ser, Asn, a hdrophobic aliphatic
      amino acid residue, Tyr, Lys, Val, Ala, a non-charged
      amino acid residue, or absent;
      residue 15 is Ile, Tyr, Asn, a hydrophobic aliphatic
      amino acid residue, Lys, D-Lys, Orn, Ala, Val, a non-
      charged amino acid residue, or absent;
      residue 16 is Leu, Asn, a hydrophobic aliphatic amino
      acid residue, Tyr, Lys, a non-charged amino acid residue,
      Ala, Val, D-Lys, Orn, D-Tyr, Phe, Trp, p-amino Phe, or
      absent;
      residue 17 is Asn, a hydrophobic aliphatic amino acid
      residue, Tyr, Lys, D-Lys, Orn, D-Tyr, Phe, Trp, p-amino
      Phe, Ala, Val, or absent;
      residue 18 is Asn, a hydrophobic aliphatic amino acid
      residue, Tyr, Lys, Val, Ala, D-Tyr, Phe, Trp, p-amino
      Phe, Nle, Leu, Ile, Ser, D-Ala, D-Lys, Orn, or absent;
      residue 19 is a hydrophobic aliphatic amino acid residue,
      Lys, D-Lys, Orn, Asn, Ser, Ile, Leu, Tyr, Nle, D-Ala,
      D-Tyr, Phe, Trp, p-amino Phe, or absent;
      residue 20 is Asn, Lys, D-Lys, Orn, Tyr, D-Tyr, Phe, Trp,
      p-amino Phe, Ser, Ile, Leu, Nle, D-Ala, a hydrophobic
      aliphatic amino acid residue, or absent;
      residue 21 is Ser, Tyr, D-Tyr, Phe, Trp, p-amino Phe, a
      hydrophobic aliphatic amino acid residue, Ile, Leu, Asn,
      Nle, D-Ala, or absent;
      residue 22 is Ile, Tyr, Ser, Asn, Leu, a hydrophobic
      aliphatic amino acid residue, Nle, D-Ala, or absent;
      residue 23 is Leu, Ile, Tyr, Asn, Ser, Nle, D-Ala, or
      absent;
      residue 24 is Asn, Ile, Tyr, Ser, Leu, or absent;
      residue 25 is Asn, Leu, Ile, Tyr, or absent;
      residue 26 is Asn, Leu, or absent;
      residue 27 is Asn or absent;
      the C-terminal residue is amidated or modified with a
      lipophilic moiety.

<400> SEQUENCE: 5

Xaa Xaa Xaa Xaa Xaa Xaa Xaa Xaa Ser Xaa Leu Asn Xaa Xaa Xaa Xaa
```

```
                1               5                  10                 15
Xaa Xaa Xaa Xaa Xaa Xaa Xaa Xaa Xaa
                        20                  25
```

<210> SEQ ID NO: 6
<211> LENGTH: 4
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated.

<400> SEQUENCE: 6

```
Lys Lys Tyr Leu
 1
```

<210> SEQ ID NO: 7
<211> LENGTH: 6
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated.

<400> SEQUENCE: 7

```
Ala Val Lys Lys Tyr Leu
 1               5
```

<210> SEQ ID NO: 8
<211> LENGTH: 5
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated.

<400> SEQUENCE: 8

```
Asn Ser Ile Leu Asn
 1               5
```

<210> SEQ ID NO: 9
<211> LENGTH: 4
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated.

<400> SEQUENCE: 9

```
Lys Lys Tyr Val
 1
```

<210> SEQ ID NO: 10
<211> LENGTH: 5
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated;

```
      residue 5 is Nle.

<400> SEQUENCE: 10

Lys Lys Tyr Leu Xaa
 1               5

<210> SEQ ID NO: 11
<211> LENGTH: 5
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated.

<400> SEQUENCE: 11

Asn Ser Tyr Leu Asn
 1               5

<210> SEQ ID NO: 12
<211> LENGTH: 5
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated.

<400> SEQUENCE: 12

Asn Ser Ile Tyr Asn
 1               5

<210> SEQ ID NO: 13
<211> LENGTH: 11
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated.

<400> SEQUENCE: 13

Lys Lys Tyr Leu Pro Pro Asn Ser Ile Leu Asn
 1               5                  10

<210> SEQ ID NO: 14
<211> LENGTH: 4
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a lauroyl
      moiety; the C-terminal residue is amidated.

<400> SEQUENCE: 14

Lys Lys Tyr Leu
 1

<210> SEQ ID NO: 15
<211> LENGTH: 4
<212> TYPE: PRT
<213> ORGANISM: Unknown
<220> FEATURE:
<223> OTHER INFORMATION: Description of Unknown Organism:Artificial
<220> FEATURE:
```

<223> OTHER INFORMATION: The N-terminus is modified with a caproyl
      moiety; the C-terminal residue is amidated.

<400> SEQUENCE: 15

Lys Lys Tyr Leu
 1

<210> SEQ ID NO: 16
<211> LENGTH: 4
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated;
      residue 4 is Nle.

<400> SEQUENCE: 16

Lys Lys Tyr Xaa
 1

<210> SEQ ID NO: 17
<211> LENGTH: 5
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated.

<400> SEQUENCE: 17

Val Lys Lys Tyr Leu
 1               5

<210> SEQ ID NO: 18
<211> LENGTH: 6
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated.

<400> SEQUENCE: 18

Leu Asn Ser Ile Leu Asn
 1               5

<210> SEQ ID NO: 19
<211> LENGTH: 7
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated.

<400> SEQUENCE: 19

Tyr Leu Asn Ser Ile Leu Asn
 1               5

<210> SEQ ID NO: 20
<211> LENGTH: 5
<212> TYPE: PRT
<213> ORGANISM: Unknown
<220> FEATURE:

```
<223> OTHER INFORMATION: Description of Unknown Organism:Artificial
<220> FEATURE:
<223> OTHER INFORMATION: The N-terminus is modified with a stearoyl
      moiety; the C-terminal residue is amidated.

<400> SEQUENCE: 20

Lys Lys Tyr Leu Asn
 1               5

<210> SEQ ID NO: 21
<211> LENGTH: 6
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated.

<400> SEQUENCE: 21

Lys Lys Tyr Leu Asn Ser
 1               5

<210> SEQ ID NO: 22
<211> LENGTH: 7
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated.

<400> SEQUENCE: 22

Lys Lys Tyr Leu Asn Ser Ile
 1               5

<210> SEQ ID NO: 23
<211> LENGTH: 8
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated.

<400> SEQUENCE: 23

Lys Lys Tyr Leu Asn Ser Ile Leu
 1               5

<210> SEQ ID NO: 24
<211> LENGTH: 11
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated;

<400> SEQUENCE: 24

Ala Val Lys Lys Tyr Leu Asn Ser Ile Leu Asn
 1               5                  10

<210> SEQ ID NO: 25
<211> LENGTH: 4
<212> TYPE: PRT
<213> ORGANISM: Unknown
```

```
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated.

<400> SEQUENCE: 25

Ser Ile Leu Asn
  1

<210> SEQ ID NO: 26
<211> LENGTH: 6
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a caproyl
      moiety; the C-terminal residue is amidated;
      residues 5 and 6 are aminocaproic acid or D-Leu.

<400> SEQUENCE: 26

Lys Lys Tyr Leu Xaa Xaa
  1               5

<210> SEQ ID NO: 27
<211> LENGTH: 5
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a lauroyl
      moiety;the C-terminal residue is amidated;
      residue 5 is aminocaproic acid or D-Leu.

<400> SEQUENCE: 27

Lys Lys Tyr Leu Xaa
  1               5

<210> SEQ ID NO: 28
<211> LENGTH: 5
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The C-terminal residue is amidated;
      residue 5 is aminocaproic acid or D-Leu.

<400> SEQUENCE: 28

Lys Lys Tyr Leu Xaa
  1               5

<210> SEQ ID NO: 29
<211> LENGTH: 6
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The C-terminal residue is amidated;
      residues 5 and 6 are aminocaproic acid or D-Leu.

<400> SEQUENCE: 29

Lys Lys Tyr Leu Xaa Xaa
  1               5

<210> SEQ ID NO: 30
```

```
<211> LENGTH: 5
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The C-terminal residue is amidated;
      residue 5 is aminolauric acid or D-Lys.

<400> SEQUENCE: 30

Lys Lys Tyr Leu Xaa
 1               5

<210> SEQ ID NO: 31
<211> LENGTH: 7
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The C-terminal residue is amidated;
      residues 5-7 are aminocaproic acid or D-Leu.

<400> SEQUENCE: 31

Lys Lys Tyr Leu Xaa Xaa Xaa
 1               5

<210> SEQ ID NO: 32
<211> LENGTH: 6
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a lauroyl
      moiety; The C-terminal residue is amidated;
      residue 6 is aminocaproic acid or D-Leu.

<400> SEQUENCE: 32

Asn Ser Ile Leu Asn Xaa
 1               5

<210> SEQ ID NO: 33
<211> LENGTH: 6
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The C-terminal residue is amidated;
      residue 6 is aminocaproic acid or D-Leu.

<400> SEQUENCE: 33

Asn Ser Ile Leu Asn Xaa
 1               5

<210> SEQ ID NO: 34
<211> LENGTH: 7
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The C-terminal residue is amidated;
      residues 6 and 7 are aminocaproic acid or D-Leu.

<400> SEQUENCE: 34

Asn Ser Ile Leu Asn Xaa Xaa
 1               5
```

```
<210> SEQ ID NO: 35
<211> LENGTH: 7
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a caproyl
      moiety; the C-terminal residue is amidated;
      residues 6 and 7 are aminocaproic acid or D-Leu.

<400> SEQUENCE: 35

Asn Ser Ile Leu Asn Xaa Xaa
  1               5

<210> SEQ ID NO: 36
<211> LENGTH: 8
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The C-terminal residue is amidated;
      residues 6-8 are aminocaproic acid or D-Leu.

<400> SEQUENCE: 36

Asn Ser Ile Leu Asn Xaa Xaa Xaa
  1               5

<210> SEQ ID NO: 37
<211> LENGTH: 6
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The C-terminal residue is amidated;
      residue 6 is aminolauric acid or D-Lys.

<400> SEQUENCE: 37

Asn Ser Ile Leu Asn Xaa
  1               5

<210> SEQ ID NO: 38
<211> LENGTH: 10
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The C-terminal residue is amidated;
      residue 5 is aminocaproic acid or D-Leu.

<400> SEQUENCE: 38

Lys Lys Tyr Leu Xaa Asn Ser Ile Leu Asn
  1               5                  10

<210> SEQ ID NO: 39
<211> LENGTH: 11
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The C-terminal residue is amidated;
      residues 5 and 6 are aminocaproic acid or D-Leu.

<400> SEQUENCE: 39

Lys Lys Tyr Leu Xaa Xaa Asn Ser Ile Leu Asn
```

```
                        1               5                  10
```

<210> SEQ ID NO: 40
<211> LENGTH: 12
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The C-terminal residue is amidated;
      residues 5-7 are aminocaproic acid or D-Leu.

<400> SEQUENCE: 40

```
Lys Lys Tyr Leu Xaa Xaa Xaa Asn Ser Ile Leu Asn
 1               5                  10
```

<210> SEQ ID NO: 41
<211> LENGTH: 10
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The C-terminal residue is amidated;
      residue 5 is aminolauric acid or D-Lys.

<400> SEQUENCE: 41

```
Lys Lys Tyr Leu Xaa Asn Ser Ile Leu Asn
 1               5                  10
```

<210> SEQ ID NO: 42
<211> LENGTH: 12
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated;
      residues 5-7 are Ala, D-Ala or p-amino Phe.

<400> SEQUENCE: 42

```
Lys Lys Tyr Leu Xaa Xaa Xaa Asn Ser Ile Leu Asn
 1               5                  10
```

<210> SEQ ID NO: 43
<211> LENGTH: 12
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated.

<400> SEQUENCE: 43

```
Lys Lys Leu Tyr Ala Ala Ala Asn Ser Ile Leu Asn
 1               5                  10
```

<210> SEQ ID NO: 44
<211> LENGTH: 10
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated.

<400> SEQUENCE: 44

Lys Lys Tyr Leu Pro Asn Ser Ile Leu Asn
 1               5                  10

<210> SEQ ID NO: 45
<211> LENGTH: 8
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated.

<400> SEQUENCE: 45

Lys Tyr Leu Asn Ser Ile Leu Asn
 1               5

<210> SEQ ID NO: 46
<211> LENGTH: 9
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated.

<400> SEQUENCE: 46

Lys Lys Tyr Leu Asn Ser Ile Leu Asn
 1               5

<210> SEQ ID NO: 47
<211> LENGTH: 9
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a lauroyl
      moiety; the C-terminal residue is amidated.

<400> SEQUENCE: 47

Lys Lys Tyr Leu Asn Ser Ile Leu Asn
 1               5

<210> SEQ ID NO: 48
<211> LENGTH: 4
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated.

<400> SEQUENCE: 48

Lys Tyr Leu Asn
 1

<210> SEQ ID NO: 49
<211> LENGTH: 5
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated;
      residue 5 is D-Ala or D-Tyr.

```
<400> SEQUENCE: 49

Lys Lys Tyr Leu Xaa
 1               5

<210> SEQ ID NO: 50
<211> LENGTH: 5
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated.

<400> SEQUENCE: 50

Lys Lys Tyr Leu Leu
 1               5

<210> SEQ ID NO: 51
<211> LENGTH: 4
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated;
      residue 2 is aminolauric acid or D-Lys.

<400> SEQUENCE: 51

Lys Xaa Tyr Leu
 1

<210> SEQ ID NO: 52
<211> LENGTH: 4
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated;
      residue 1 is aminolauric acid or D-Lys.

<400> SEQUENCE: 52

Xaa Lys Tyr Leu
 1

<210> SEQ ID NO: 53
<211> LENGTH: 4
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated;
      residues 1 and 2 are aminolauric acid or D-Lys.

<400> SEQUENCE: 53

Xaa Xaa Tyr Leu
 1

<210> SEQ ID NO: 54
<211> LENGTH: 4
<212> TYPE: PRT
<213> ORGANISM: Unknown
<220> FEATURE:
```

```
<223> OTHER INFORMATION: Description of Unknown Organism:Artificial
<220> FEATURE:
<223> OTHER INFORMATION: The N-terminus is modified with a stearoyl
      moiety; the C-terminal residue is amidated.

<400> SEQUENCE: 54

Lys Lys Phe Leu
 1

<210> SEQ ID NO: 55
<211> LENGTH: 4
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated;
      residue 4 is aminocaproic acid or D-Leu.

<400> SEQUENCE: 55

Lys Lys Tyr Xaa
 1

<210> SEQ ID NO: 56
<211> LENGTH: 4
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated.

<400> SEQUENCE: 56

Lys Lys Trp Leu
 1

<210> SEQ ID NO: 57
<211> LENGTH: 4
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated;
      residue 3 is Ala, D-Ala or p-amino Phe.

<400> SEQUENCE: 57

Lys Lys Xaa Leu
 1

<210> SEQ ID NO: 58
<211> LENGTH: 4
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated;
      residue 2 is Orn.

<400> SEQUENCE: 58

Lys Xaa Tyr Leu
 1

<210> SEQ ID NO: 59
```

```
<211> LENGTH: 4
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated;
      residue 1 is Orn.

<400> SEQUENCE: 59

Xaa Lys Tyr Leu
 1

<210> SEQ ID NO: 60
<211> LENGTH: 4
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated;
      residues 1 and 2 are Orn.

<400> SEQUENCE: 60

Xaa Xaa Tyr Leu
 1

<210> SEQ ID NO: 61
<211> LENGTH: 4
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a oleic acid
      moiety; the C-terminal residue is amidated.

<400> SEQUENCE: 61

Lys Lys Tyr Leu
 1

<210> SEQ ID NO: 62
<211> LENGTH: 4
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a propyl
      moiety; the C-terminal residue is amidated.

<400> SEQUENCE: 62

Lys Lys Tyr Leu
 1

<210> SEQ ID NO: 63
<211> LENGTH: 10
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated.

<400> SEQUENCE: 63

Lys Lys Tyr Leu Ala Ala Lys Lys Tyr Leu
 1               5                  10
```

<210> SEQ ID NO: 64
<211> LENGTH: 10
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated.

<400> SEQUENCE: 64

Lys Lys Tyr Leu Pro Pro Lys Lys Tyr Leu
 1               5                  10

<210> SEQ ID NO: 65
<211> LENGTH: 9
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated;
      residue 5 is aminocaproic acid.

<400> SEQUENCE: 65

Lys Lys Tyr Leu Xaa Lys Lys Tyr Leu
 1               5

<210> SEQ ID NO: 66
<211> LENGTH: 9
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated;
      residue 5 is aminolauric acid.

<400> SEQUENCE: 66

Lys Lys Tyr Leu Xaa Lys Lys Tyr Leu
 1               5

<210> SEQ ID NO: 67
<211> LENGTH: 5
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated.

<400> SEQUENCE: 67

Lys Lys Tyr Leu Leu
 1               5

<210> SEQ ID NO: 68
<211> LENGTH: 5
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a caproyl
      moiety; the C-terminal residue is amidated.

<400> SEQUENCE: 68

Asn Ser Ile Leu Asn
1               5

<210> SEQ ID NO: 69
<211> LENGTH: 5
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a lauroyl
      moiety; the C-terminal residue is amidated.

<400> SEQUENCE: 69

Asn Ser Ile Leu Asn
1               5

<210> SEQ ID NO: 70
<211> LENGTH: 6
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated.

<400> SEQUENCE: 70

Lys Lys Lys Tyr Leu Asp
1               5

<210> SEQ ID NO: 71
<211> LENGTH: 6
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated.

<400> SEQUENCE: 71

Cys Lys Lys Tyr Leu Cys
1               5

<210> SEQ ID NO: 72
<211> LENGTH: 6
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated.

<400> SEQUENCE: 72

Cys Lys Lys Tyr Leu Lys
1               5

<210> SEQ ID NO: 73
<211> LENGTH: 6
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated.

```
<400> SEQUENCE: 73

Leu Asn Ser Ile Leu Asn
 1               5

<210> SEQ ID NO: 74
<211> LENGTH: 6
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: The N-terminus is modified with a stearoyl
      moiety; the C-terminal residue is amidated.

<400> SEQUENCE: 74

Asn Ser Ile Tyr Leu Asn
 1               5

<210> SEQ ID NO: 75
<211> LENGTH: 6
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: Xaa at position 1 is a residue of a hydrophobic
      aliphatic amino acid

<400> SEQUENCE: 75

Xaa Asn Ser Ile Leu Asn
 1               5

<210> SEQ ID NO: 76
<211> LENGTH: 6
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: Xaa at position 1 is a residue of a hydrophobic
      aliphatic amino acid

<400> SEQUENCE: 76

Xaa Asn Ser Tyr Leu Asn
 1               5

<210> SEQ ID NO: 77
<211> LENGTH: 7
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: Xaa at position 6 is a residue of a hydrophobic
      aliphatic amino acid

<400> SEQUENCE: 77

Val Ala Lys Lys Tyr Xaa Asn
 1               5

<210> SEQ ID NO: 78
<211> LENGTH: 7
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: Xaa at position 6 is a residue of a hydrophobic
      aliphatic amino acid
```

-continued

```
<400> SEQUENCE: 78

Ala Val Lys Lys Tyr Xaa Asn
 1               5

<210> SEQ ID NO: 79
<211> LENGTH: 11
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: Any one or all of residues 1-7 may be present
      or absent;
      residue 1 is Val, Ala, or absent;
      residue 2 is Val, Ala, or absent;
      residue 3 is Lys, Val, or absent;
      residue 4 is Lys or absent;
      residue 5 is Tyr, Lys, or absent;
      residue 6 is a hydrophobic aliphatic amino acid residue,
      Tyr, Lys, or absent;
      residue 7 is Asn, a hydrophobic aliphatic amino acid
      residue, or absent;
      residue 9 is Ile or Tyr;
      the C-terminal residue is amidated or modified with a
      lipophilic moiety.

<400> SEQUENCE: 79

Xaa Xaa Xaa Xaa Xaa Xaa Xaa Ser Xaa Leu Asn
 1               5                  10

<210> SEQ ID NO: 80
<211> LENGTH: 11
<212> TYPE: PRT
<213> ORGANISM: Unknown
<220> FEATURE:
<223> OTHER INFORMATION: Description of Unknown Organism:Artificial
<220> FEATURE:
<223> OTHER INFORMATION: Any one or all of residues 1, 2 and 3 may be
      present or absent; residue 1 is Ala, Val, or
      absent; residue 2 is Ala, Val, or absent; residue
      3 is Ala, Val, Lys, D-Lys, Orn or absent; one of
      residues 1, 2, 3 or 4 is the N-terminal residue,
      and may be modified with a lipophilic moiety;
      residue 4 is Lys, D-Lys, or Orn;
      residue 5 is Tyr, D-Tyr, Phe, Trp, or p-amino Phe;
      residue 6 is a hydrophobic amino acid residue;
      any one or all of residues 7-11 may be present or
      absent; residue 7 is Asn, Ser, Ile, Tyr, Leu, Nle,
      D-Ala, or absent; residue 8 is Ser or absent;
      residue 9 is Ile, Tyr, or absent; residue 10 is Leu
      or absent; residue 11 is Asn or absent;
      the C-terminal residue is amidated or modified with a
      lipophilic moiety.

<400> SEQUENCE: 80

Xaa Xaa Xaa Xaa Xaa Xaa Xaa Xaa Xaa Xaa Xaa
 1               5                  10
```